(12) United States Patent
Cunningham et al.

(10) Patent No.: US 7,862,477 B2
(45) Date of Patent: Jan. 4, 2011

(54) METHOD TO EVALUATE A CLIENT BY A PHYSICAL THERAPIST

(76) Inventors: Shala Cunningham, 3288 Foxridge Dr., Jasper, IN (US) 47546; Erik Womeldorf, 3288 Foxridge Dr., Jasper, IN (US) 47546

( * ) Notice: Subject to any disclaimer, the term of this patent is extended or adjusted under 35 U.S.C. 154(b) by 788 days.

(21) Appl. No.: 11/888,266

(22) Filed: Jul. 30, 2007

(65) Prior Publication Data

US 2008/0027758 A1 Jan. 31, 2008

Related U.S. Application Data

(60) Provisional application No. 60/834,108, filed on Jul. 28, 2006.

(51) Int. Cl.
*A63B 71/00* (2006.01)
(52) U.S. Cl. ............... 482/8; 482/1; 482/901; 600/301; 705/2
(58) Field of Classification Search ............... 482/1–9, 482/900–902; 705/2, 3; 600/300, 301; 340/573.1
See application file for complete search history.

(56) References Cited

U.S. PATENT DOCUMENTS

| 6,292,783 | B1 | 9/2001 | Rohler et al. |
| 6,820,037 | B2 | 11/2004 | Simon |
| 7,451,096 | B2 * | 11/2008 | Rucker ........................... 705/3 |
| 7,502,498 | B2 * | 3/2009 | Wen et al. .................... 382/128 |
| 2007/0085690 | A1 * | 4/2007 | Tran ......................... 340/573.1 |

* cited by examiner

*Primary Examiner*—Glenn Richman
(74) *Attorney, Agent, or Firm*—Dale F. Regelman; Quarles & Brady LLP

(57) ABSTRACT

A method to evaluate a client by a physical therapist, which includes determining if a client is experiencing distress. If a client is experiencing pain, the method selects an evaluation algorithm responsive to the distress, wherein the selected evaluation algorithm comprises (N) evaluation factors. The method determines if any of the (N) evaluation factors is designated an Emergency Referral evaluation factor, and if any of the (N) evaluation factors is designated an Emergency Referral evaluation factor determines if the client's reported distress corresponds to a point rating of "5" for any of the Emergency Referral evaluation factors. If the client's reported distress corresponds to a point rating of "5" for any of the Emergency Referral evaluation factors, the method refers the patent for immediate emergency care.

24 Claims, 2 Drawing Sheets

US 7,862,477 B2

METHOD TO EVALUATE A CLIENT BY A PHYSICAL THERAPIST

CROSS REFERENCE TO RELATED APPLICATIONS

This Application claims priority from a U.S. Provisional Application having Ser. No. 60/834,108 filed Jul. 28, 2006.

FIELD OF THE INVENTION

Pain is universally understood as a sign of disease. It is the most common symptom that brings a client to a physician's attention. Pain is a perception versus a sensation that is based on physical state, experience and individual interpretation. As physical therapists are being placed in a position to be the screening professional for orthopedic clients, it is imperative that physical therapists be able to note the cardinal signs and symptoms of disease that would warrant a referral to a physician, specialist or immediate emergency care.

SUMMARY OF THE INVENTION

Applicants' method provides a screening process to be used by therapists to assist in determining the need for medical referral. This tool is designed to be used in addition to sound clinical judgment developed in the standard physical therapy entry level college education. As those skilled in the art will appreciate, identification of etiology by physical therapists is limited primarily to kinesiologic problems. Physical therapists must be able to determine when pain patterns are accompanied by signs and symptoms that indicate non-musculoskeletal involvement.

Applicants' method should be employed with each new client contact. More commonly than being the primary contact, the family physician is relying on the therapist to "evaluate and treat," rather than follow a predetermined diagnosis. Clients may also obtain a signed prescription for physical therapy from a physician based on previous history of a similar musculoskeletal problem without actually seeing that physician for an assessment.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Figure 1:
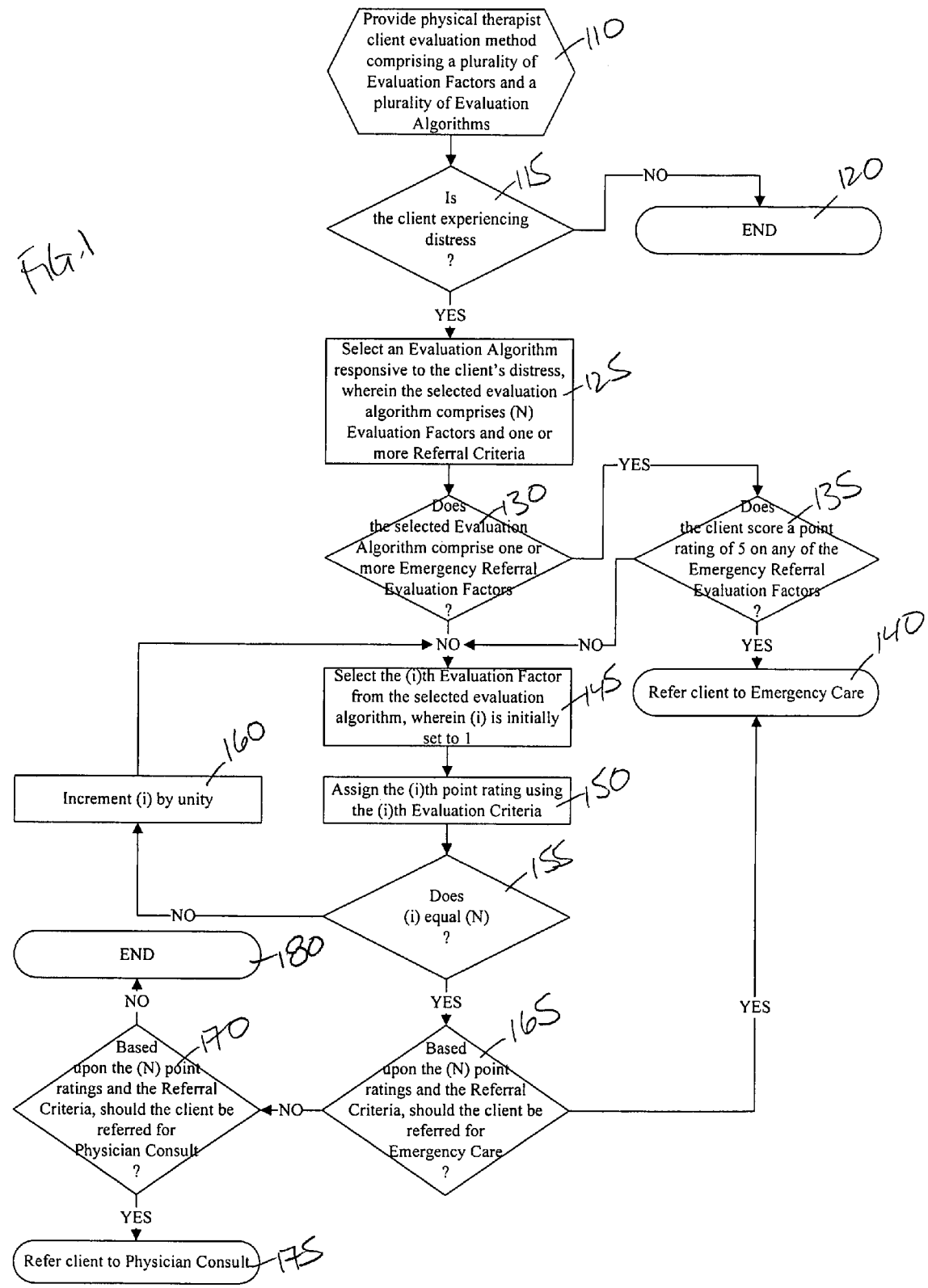
FIG. 1 is a flow chart summarizing the steps of Applicant's method.

Applicants' invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Applicants' method separates the continuum of possible responses to each of a plurality of Evaluation Factors. In certain embodiments, Applicants' method comprises 111 Evaluation Factors. In certain embodiments, Applicants' method specifies point ratings from 0 to 5 for each of the plurality of Evaluation Factors. Summing individual point ratings to calculate an aggregate rating provides a prediction that a non-musculoskeletal disease exists. The higher the aggregate rating, the more likely the client suffers from a non-musculoskeletal disease. In addition, Applicants' method indicates when a referral for Emergency Care may be necessary. By "Emergency Care," Applicants mean immediate referral and transportation to a medical facility, such as an Emergency Department, emergency Room, Trauma Center, and the like.

In certain embodiments, Applicants' method the comprises 111 Evaluation Factors recited in TABLE I. Certain Evaluation Factors recited in Table I that comprise an "ER" designation. Such an "ER" designation means that a point rating of 5 for any one of those ER Evaluation Factors indicates the client should be referred to Emergency Care for further medical evaluation.

TABLE I

| Evaluation Factors | |
|---|---|
| Anemia | |
| Angina | ER |
| Ankle and foot contact quality | |
| Ankle and foot daytime pain | |
| Ankle and foot nighttime pain | |
| Ankle and foot quality of pain | |
| Ankle and foot trauma | |
| Ankle and foot vascular changes | ER |
| Bleeding tendency | ER |
| Blood in urine | ER |
| Cervical daytime pain | |
| Cervical extent of pain referral | |
| Cervical nighttime pain | ER |
| Cervical pain precipitating factors | ER |
| Cervical pain relieving factors | |
| Cervical paresthesia | |
| Cervical quality of pain | |
| Cervical trauma | ER |
| Constipation | |
| Control of bowels | ER |
| Control of urine | ER |
| Cough | ER |
| Day sweats | |
| Diabetes mellitus | |
| Diplopia | ER |
| Elbow contact quality | |
| Elbow daytime pain | |
| Elbow nighttime pain | |
| Elbow quality of pain | |
| Elbow trauma | |
| Exercise impact on presenting symptom | ER |
| Extent of lower extremity weakness | ER |
| Extent of upper extremity weakness | ER |
| Fatigue | |

TABLE I-continued

| Evaluation Factors | |
|---|---|
| Fever | ER |
| Frequency of lower extremity change in sensation | |
| Frequency of lower extremity weakness | |
| Frequency of upper extremity change in sensation | |
| Frequency of upper extremity weakness | |
| Headache | ER |
| Hearing loss | |
| Heartburn | |
| Hip contact quality | |
| Hip daytime pain | ER |
| Hip nighttime pain | ER |
| Hip quality of pain | |
| Hip trauma | ER |
| Immune suppression | |
| Joint stiffness | |
| Joint swelling | |
| Knee contact quality | |
| Knee daytime pain | |
| Knee nighttime pain | |
| Knee quality of pain | |
| Knee trauma | |
| Lumbosacral daytime pain | |
| Lumbosacral extent of pain referral | |
| Lumbosacral nighttime pain | ER |
| Lumbosacral pain precipitating factors | |
| Lumbosacral pain relieving factors | |
| Lumbosacral paresthesia | |
| Lumbosacral quality of pain | |
| Lumbosacral trauma | ER |
| Medical compliance self assessment | |
| Nausea | |
| Night sweats | ER |
| Oxygen usage | |
| Palpitations | ER |
| Photophobia | ER |
| Relief of presenting symptom | ER |
| Respiratory chest wall or shoulder pain | ER |
| Rheumatoid Arthritis | |
| Short of breath | ER |
| Shoulder contact quality | |
| Shoulder daytime pain | |
| Shoulder nighttime pain | |
| Shoulder pain precipitating factors | |
| Shoulder pain relieving factors | |
| Shoulder quality of pain | |
| Shoulder trauma | |
| Skin morphology | |
| Sleep pattern | |
| Stool color | ER |
| Stool consistency | |
| Stool volume | |
| Sunlight effect on skin | |
| Swallow coordination | |
| Swallowing completeness | |
| Systemic Lupus Erythematosis | |
| Thoracic daytime pain | |
| Thoracic extent of pain referral | |
| Thoracic nighttime pain | ER |
| Thoracic pain precipitating factors | |
| Thoracic pain relieving factors | |
| Thoracic paresthesia | |
| Thoracic quality of pain | |
| Thoracic trauma | ER |
| Urinary frequency | ER |
| Vertigo | ER |
| Visual disturbance | |
| Visual loss | ER |
| Vomiting | ER |
| Weight loss | |
| Wrist and hand bony deformities | |
| Wrist and hand contact quality | |
| Wrist and hand daytime pain | |
| Wrist and hand nighttime pain | |

TABLE I-continued

| Evaluation Factors | |
|---|---|
| Wrist and hand non bony deformities | |
| Wrist and hand quality of pain | |
| Wrist and hand trauma | |
| Wrist and hand vascular changes | ER |

Applicants' method further comprises an Emergency Medical Algorithm recited herein below. In addition, Applicants' method further comprises a plurality of Evaluation Algorithms responsive to a wide variety of signs, symptoms, and/or complaints, associated with a presenting client. In certain embodiments, these complaint-specific Evaluation Algorithms comprise: an Ankle and Foot Algorithm, a Cervical Spine Algorithm, an Elbow Algorithm, a Hand and Wrist Algorithm, a Headache Algorithm, a Hip Algorithm, a Knee Algorithm, a Lumbar Spine Algorithm, a Pelvic And Sacrum Algorithm, a Shoulder Algorithm, a Thoracic Spine Algorithm, a Poor Gait Algorithm, and a Vertigo Algorithm. Each of the above-recited Evaluation Algorithms comprise a plurality of the above-recited 111 Evaluation Factors.

To assist a physical therapist to evaluate whether to refer a presenting client to Emergency Care or to a Physician Consult, Applicants' invention comprises a method utilizing Applicants' plurality of Evaluation Algorithms and Evaluation Factors. FIG. 1 summarizes the steps of Applicants' method. Referring now to FIG. 1, in step 110 the method provides a plurality of Evaluation Factors and a plurality of Evaluation Algorithms.

In certain embodiments the plurality of Evaluation Factors of step 110 are recited in Table. 1 herein. In certain embodiments the plurality of Evaluation Algorithms of step 110 comprise Applicants' Emergency Medical Algorithm, Ankle and Foot Algorithm, Cervical Spine Algorithm, Elbow Algorithm, Hand and Wrist Algorithm, Headache Algorithm, Hip Algorithm, Knee Algorithm, Lumbar Spine Algorithm, Pelvic And Sacrum Algorithm, Shoulder Algorithm, Thoracic Spine Algorithm, Poor Gait Algorithm, and Vertigo Algorithm.

In step 115, the physical therapist determines if a presenting client is experiencing distress. In certain embodiments, the distress of step 115 comprises one or more observable signs. In certain embodiments, the distress of step 115 comprises one or more quantifiable symptoms. In certain embodiments, the distress of step 115 comprises pain. In certain embodiments, the determination of step 115 is made by observing the presenting client. In certain embodiments, the determination of step 115 is made by physical examination of the presenting client. In certain embodiments, the determination of step 115 is made by asking the presenting client one or more questions.

If the physical therapist determines in step 115 that a presenting client is not experiencing distress, then the method transitions from step 115 to step 120 and ends. Alternatively, if the physical therapist determines in step 115 that the presenting client is experiencing distress, then the method transitions from step 115 to step 125 wherein the physical therapist selects an Evaluation Algorithm responsive to the presenting client's distress, wherein that Evaluation Algorithm comprises (N) Evaluation Factors. For example, if the physical therapist selects Applicants' Hand/Wrist Algorithm in step 125, that selected Evaluation Algorithm comprises 42 Evaluation Factors.

In step 130, the physical therapist determines if the selected Evaluation Algorithm comprises one or more Emergency Referral Evaluation Factors. If the selected Evaluation Algorithm does not comprises any Emergency Referral Evaluation Factors, then the method transitions from step 130 to step 145.

If the selected Evaluation Algorithm comprises one or more Emergency Referral Evaluation Factors, then the method transitions from step 130 to step 135 wherein the physical therapist evaluates whether the client scores a point rating of 5 on any of applicable Emergency Referral Evaluation Factors. If the physical therapist determines in step 135 that the client scores a point rating of 5 on any of applicable Emergency Referral Evaluation Factors, then the method transitions from step 135 to step 140 wherein the physical therapist refers the client for Emergency Care.

Alternatively, if the physical therapist determines in step 135 that the client does not score a point rating of 5 on any of applicable Emergency Referral Evaluation Factors, then the method transitions from step 135 to step 145 wherein the physical therapist selects the (i)th Evaluation Factor of the selected Evaluation Algorithm, wherein (i) is initially set to 1.

In step 150, the physical therapist assigns the (i)th point rating using the (i)th Evaluation Criteria recited in the (i)th Evaluation Factor. In step 155, the physical therapist determines if all the Evaluation Factors of the selected Evaluation Algorithm have been examined, i.e. if (i) equals (N). If the physical therapist determines that all the Evaluation Factors of the selected Evaluation Algorithm have not been examined, then the method transitions from step 155 to step 160 wherein (i) is incremented by unity, and the method transitions from step 160 to step 145 and continues as described herein.

Alternatively, if the physical therapist determines that all the Evaluation Factors of the selected Evaluation Algorithm have been examined, then the method transitions from step 155 to step 165 wherein the physical therapist uses (N) point ratings assigned in combination with the Referral Criteria recited in the selected Evaluation Algorithm of step 125 to determine if the client should be referred to Emergency Care.

If the physical therapist determines in step 165 that the client should be referred to Emergency Care, then the method transitions from step 165 to step 140 wherein the physical therapist refers the presenting client to Emergency Care. Alternatively, if the physical therapist determines in step 165 that the client should not be referred to Emergency Care, then the method transitions from stop 165 to step 170 wherein the physical therapist uses (N) point ratings assigned in combination with the Referral Criteria recited in the selected Evaluation Algorithm of step 125 to determine if the client should be referred to a Physician Consult. If the physical therapist determines in step 170 that the client should be referred to a Physician Consult, then the method transitions from step 170 to step 175 wherein the physical therapist refers the presenting client to a Physician Consult. Alternatively, if the physical therapist determines in step 170 that the client should not be referred to a Physician Consult, then the method transitions from stop 170 to step 180 and ends.

In certain embodiments, step 125 comprises selecting more than one Evaluation Algorithm responsive to the presenting client's distress. For example, if the physical therapist selects (M) Evaluation Algorithms in step 125, the method first utilizes the (j)th Evaluation Algorithm, wherein (j) is initially set to 1, and wherein as a general matter (j) is greater than or equal to 1 and less than or equal to (M), and wherein the physical therapist uses two or more of steps 130, 135, 140, 145, 150, 155, 160, 165, 170, 175, and/or 180 in implementing the (j)th Evaluation Algorithm. If the (j)th Evaluation Algorithm ends at step 140, then the method ends and the client is referred to Emergency Care. Alternatively, if the (j)th Evaluation Algorithm ends at step 175 or at step 180, then (j) is incremented by unity, and the method transitions back to step 125 wherein the (j)th Evaluation Algorithm is implemented as described herein. This iterative procedure is used until each of the (M) Evaluation Algorithms has been implemented, i.e. until (j) is greater than (M).

Figure 2:
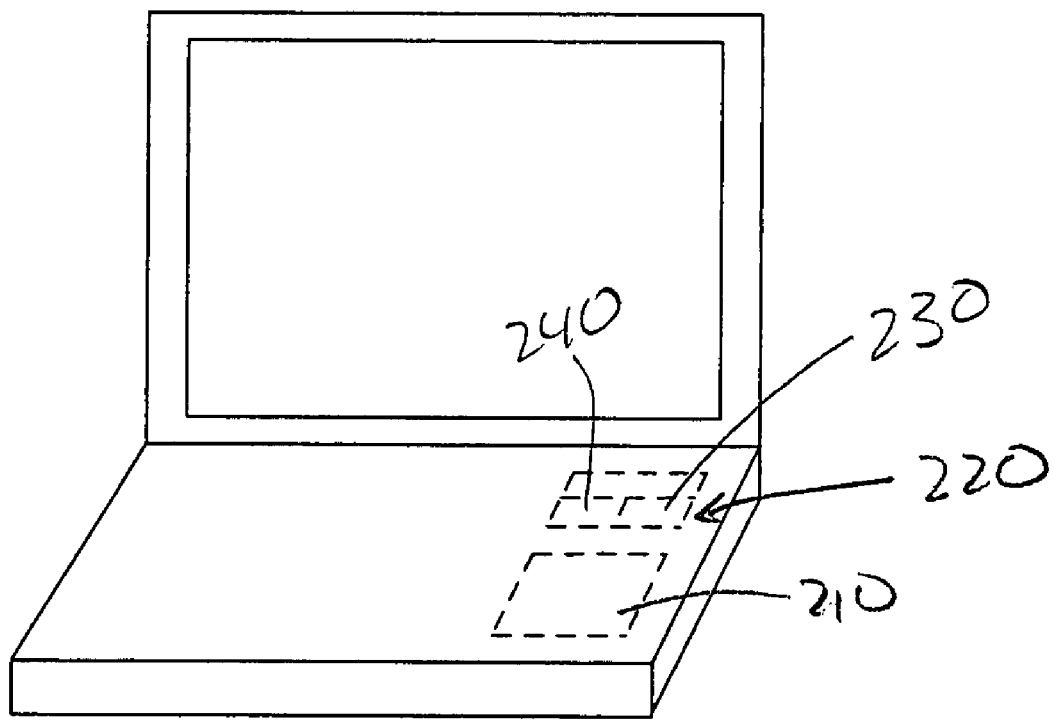
FIG. 2 is a perspective view of a computing device used to implement one or more of the steps of FIG. 1.

Referring now to FIG. 2, in certain embodiments, Applicants' invention includes instructions, such as instructions 230 encoded in memory, such as memory 220, residing in a computing device, such as computing device 200, wherein those instructions are executed by a processor, such as processor 210, to implement one or more of steps 115, 125, 130, 135, 140, 145, 150, 155, 165, 170, and/or 175, recited in FIG. 1.

In other embodiments, Applicants' invention includes a computer program product, such as computer program product 240, encoded in memory 220, wherein processor 210 utilizes computer program product 240 to implement one or more of steps 115, 125, 130, 135, 140, 145, 150, 155, 165, 170, and/or 175, recited in FIG. 1. In either case, the instructions and/or the computer program product may be encoded in an information storage medium comprising, for example, a magnetic information storage medium, an optical information storage medium, an electronic information storage medium, and the like. By "electronic storage media," Applicants mean, for example, a device such as a PROM, EPROM, EEPROM, Flash PROM, compactflash, smartmedia, and the like.

Applicants' Evaluation Algorithms, the Referral Criteria associated with each of those Evaluation Algorithm, the individual Evaluation Factors comprising those Evaluation Algorithms, and the Evaluation Criteria associated with each Evaluation Factor, are set forth seriatim hereinbelow.

Emergency Medical Algorithm

Therapists, in any clinical situation, must be able to recognize life threatening conditions that would require Emergency Care. Clients that appear to be stable in their current medical condition can have an unexpected life threatening situation arise, or an exacerbation of their current condition, that would warrant Emergency Care.

Applicants' method includes a Medical Emergency Determination algorithm. Advanced Cardiac Life Support (ACLS) and Advanced Trauma Life Support (ATLS) rely on the first few letters of the alphabet to guide the initial survey of unstable individuals. This is a useful guide for determining severity of the emergency when an individual is in apparent distress. It prioritizes the care for an individual with multiple, severe problems occurring at once. If unable to treat multiple problems simultaneously, ATLS recommends securing the airway as the highest priority. The second priority is breathing maintenance and the third priority is circulatory management.

A—Airway
B—Breathing
C—Circulation
D—Disability
E—Exposure/Environmental

Airway compromise can realistically occur in the office setting. A sore throat can infect the epiglottis and close the airway. Other compromises to the airway can lead to death before paramedics can arrive to assist with the emergency, for example choking. Endotracheal intubation may be necessary when oral secretions cannot be controlled, stridor is heard or chest wall retraction is noted with inspiration. As a general matter, airway maintenance is the highest priority. Transfer to an emergency department is appropriate when there is concern regarding maintenance of the airway.

If any of following Evaluation Factors are answered with a score of five (5), the presenting client may be experiencing a medical emergency. In accord with this embodiment of Applicants' method, if the client has a referring physician, then an attempt should be made to discuss this client immediately. When a referring physician is not available, the client should be referred to the emergency department.

| |
|---|
| Constitutional Fever |

0  if none
1  if felt warm but never took temp
2  if recorded a Temp: above normal but <99.5
3  if recorded a Temp: 99.5 but <101
4  if recorded a Temp: 101 but <103
5  if recorded a Temp: 103 or higher

| |
|---|
| Constitutional Night sweats |

0  if none
1  if once in last 10 nights
2  if > once in last 10 nights but <= every 3 nights
3  if > once every 3 nights but <= once a night
4  if every night but no change in bedclothes needed
5  if every night & changing bedclothes needed

| |
|---|
| Pulmonary Cough |

0  if none
1  if cough < once every 3 days
2  if cough >= once every 3 days but not daily & cough considered tolerable to client
3  if cough >= once every 3 days but not daily, & cough considered not tolerable to client
4  if daily cough but does not feel like it is non-stop
5  if feels like non-stop coughing

| |
|---|
| Pulmonary Short of breath |

0  if never
1  if short of breath once in last 10 days
2  if short of breath once >3 days ago but <10 days ago
3  if short of breath once <=3 days ago or daily, but not more than once a day
4  if short of breath more than once a day but <5 times a day
5  if short of breath 5 times a day or more

| |
|---|
| Pulmonary Respiratory chest wall or shoulder pain |

0  if none
1  if noted with cough or deep breath but 5 days or more between episodes
2  if noted with cough or deep breath every 5 days or less, but not daily
3  if noted with cough or deep breath, occurring daily, but tolerable to client
4  if noted with cough or deep breath, occurring daily, intolerable to client, not constant
5  if noting pain from cough or deep breath constantly throughout the day

| |
|---|
| Gastrointestinal Vomiting |

0  if none
1  if vomiting once every 5 days
2  if vomiting not daily but < every 5 days
3  if vomiting daily but <=3 times a day
4  if vomiting >3 times a day but not constantly vomiting
5  if constantly vomiting

| |
|---|
| Gastrointestinal Stool color |

0  if never had black nor bloody stools
1  if black or bloody stool once in last month
2  if black or bloody stools but occurring > once a month but < once a week
3  if black or bloody stools but occurring >= once a week but < every 2 days
4  if black or bloody stools but occurring every 2 days or more frequently but not 5 days in a row
5  if black or bloody stools for 5 days in a row or more

| |
|---|
| Gastrointestinal Control of bowels |

0  if complete control or longstanding continence problems proven benign by a workup
1  if new rectal leakage occurs but not more than once a month
2  if new rectal leakage occurs > once a month but <= once a week
3  if new rectal leakage occurs > once a week but not daily
4  if daily new rectal leakage but can wear same underwear throughout day
5  if daily new rectal leakage & change of underwear needed or protective padding used -continued

Genitourinary Blood in urine 0 if none
1 if noted but not more than once a month
2 if noted > once a month but <= once a week
3 if noted > once a week but not daily
4 if noted daily but not constantly
5 if noted with every void

Genitourinary Control of urine 0 if complete control or longstanding continence problems proven benign by a workup
1 if new episodes of loss of control but not more than once a month
2 if new episodes of loss of control > once a month but <= once a week
3 if new episodes of loss of control > once a week but not daily
4 if daily new episodes of loss of control but can wear same underwear throughout day
5 if daily new episodes of loss of control & change of underwear needed or protective padding used

Cardiovascular Palpitations 0 if none
1 if occurring but not more than once a month
2 if occurring but > once a month but <= once a week
3 if occurring > once a week but not daily
4 if occurring daily but not passing out
5 if ever passed out while having palpitations

Cardiovascular Angina 0 if none
1 if client told chest pain is not cardiac because of stress test or angiogram negative within last month
2 if followed in cardiology and no new nor worsening symptoms since last cardiology visit (stable angina)
3 if new or worsening chest pain intermittently at rest, none with activity
4 if new or worsening chest pain with activity relieved with rest
5 if currently experiencing new or worsening chest pain

Cardiovascular Relief of presenting symptom 0 if symptom is distal to elbow or below waist * Note: Choices 1 to 5 assume symptom more proximal
1 if symptom resolves in <1 minute without anything
2 currently taking a long acting nitroglycerin product (Isordil Imdur or Nitropatch)
3 if up to ½ of events spontaneously resolve & ½ of events require nitroglycerin or oxygen
4 if more than ½ of the events require nitroglycerin or oxygen but symptoms are not constant
5 if symptoms are constant unless nitroglycerin or oxygen is used or persist despite NTG or O2

Cardiovascular Exercise impact on presenting symptom 0 if symptom is distal to elbow or below waist Note * Choices 1 to 5 assume symptom more proximal
1 if symptom develops during rest after full exercise capacity
2 if symptom occurs @ maximal exercise capacity
3 if symptom occurs @ 50% or higher of maximal exercise capacity
4 if symptom occurs @ less than 50% of maximal exercise capacity but not immediately
5 if any exertional effort reproduces symptom nearly immediately

Neurologic Visual loss 0 if none Note * Choices 1-5 are either in 1 eye or both
1 for <10 seconds and occurred over a month ago
2 if had a reversible episode >10 seconds but occurred >10 days ago
3 if had a reversible episode >10 seconds but occurred >3 days ago but <=10 days ago
4 if had a reversible episode >10 seconds but occurred <=3 days ago
5 if new onset visual loss that persists

Neurologic Diplopia 0 if never * Note: Another way to describe diplopia is double vision
1 for <10 seconds and occurred over a month ago
2 if had a reversible episode >10 seconds but occurred >10 days ago
3 if had a reversible episode >10 seconds but occurred >3 days ago but <=10 days ago
4 if had a reversible episode >10 seconds but occurred <=3 days ago
5 if new onset double vision that persists -continued

Neurologic Photophobia 0 if none. Note * Photophobia means exposure to light (such as indoors to outdoors) causes pain
1 for <10 seconds and occurred over a month ago
2 if had an episode >10 seconds but occurred >10 days ago
3 if had an episode >10 seconds but occurred >3 days ago but <=10 days ago
4 if had an episode >10 seconds but occurred <=3 days ago
5 if new onset photophobia that persists

Neurologic Vertigo 0 if none
1 for <10 seconds and occurred over a month ago
2 if had an episode >10 seconds but occurred >10 days ago
3 if had an episode >10 seconds but occurred >3 days ago but <=10 days ago
4 if had an episode >10 seconds but occurred <=3 days ago
5 if new onset vertigo that persists

Neurologic Headache 0 if no new or worsening headache
1 if new or worsening headache <20 minutes and occurred over 2 weeks ago
2 if new or worsening headache lasting <20 minutes and occurred within 2 weeks
3 if new or worsening headache >=20 minutes but occurred >1 week ago
4 if new or worsening headache >=20 minutes but occurred within last week, currently headache free
5 if currently experiencing new or worsening headaches lasting >=20 minutes

Neurologic Extent of upper extremity weakness 0 if none * Note: Score 0 if due to previously evaluated stroke or injury and unchanged since that event
1 if seems weak but no loss of function
2 if noticing weakness (dropping things) but maintaining ADLs
3 if noticing weakness and impacting ADLs but can push self away
4 if able to move upper extremity but cannot push self away
5 if unable to move upper extremity

Neurologic Extent of lower extremity weakness 0 if none * Note: Score 0 if due to previously evaluated stroke or injury and unchanged since that event
1 if seems weak but no loss of function
2 if noticing weakness while walking (stopping or shorter distances) but can walk without falling
3 if noticing weakness will fall while walking or relying on wheelchair or other assisted mobility
4 if able to move legs but cannot walk nor go from seated to standing
5 if unable to move lower extremity

Lumbosacral Lumbosacral nighttime pain 0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

Lumbosacral Lumbosacral trauma 0 if no lumbosacral pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

Thoracic Thoracic nighttime pain 0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

Thoracic Thoracic trauma 0 if no thoracic pain * Note: Known incident means a recalled activity leading to the pain
1 gradual onset of pain without known incident -continued 2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain Cervical Cervical nighttime pain 0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation Cervical Cervical pain precipitating factors 0 if no cervical pain * Note: Specific cervical range of motion = flexion, extension or rotation
1 if only worse with specific cervical range of motion easily reproduced
2 if worse when sitting or standing without head support but not immediately
3 if worse when sitting or standing without head support, occurs immediately
4 if constant pain, no associated symptoms (nausea, photophobia, headache, fever)
5 if constant pain plus another symptom (nausea, photophobia, headache, fever)

Cervical Cervical trauma 0 if no cervical pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain Hip Hip daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics Hip Hip nighttime pain 0 if no hip pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics Hip Hip trauma 0 if no hip pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain Wrist and Hand Wrist and hand vascular changes 0 if none
1 if cold occasionally no pain no ulcers & functional
2 if ischemic pain, no ulcers & functional
3 if one ulcer
4 several ulcers or threatened digits
5 previous auto-amputation or black necrotic digits Ankle and Foot Ankle and foot vascular changes 0 if none
1 if cold occasionally no pain no ulcers & functional
2 if ischemic pain, no ulcers & functional -continued 3 if one ulcer
4 several ulcers or threatened digits
5 previous auto-amputation or black necrotic digits Hematological Bleeding tendency 0 if none * Note: Heparin and low-molecular weight heparin is by shot; warfarin = Coumadin
1 if taking aspirin or Plavix
2 if on heparin, low-molecular weight heparin or warfarin
3 if client carries a diagnosis as having potentially life threatening bleeding disease but no exacerbation
4 if new onset spontaneously bleeding, client can self-control
5 if new onset spontaneously bleeding which client is unable to self-control Differentiating between a client who should be referred to Emergency Care and one who should not can be difficult. Lab tests, EKGs, and imaging studies cannot be done in an outpatient physical therapy setting. Plus there is tremendous variability in the patient's perception and response to any symptom or pain. Clinical judgment is important. Applicants' method includes choosing to call 911 for anything that seems like an emergency.

Cervical Spine Algorithm

1. Constitutional Fever
   0 if none
   1 if felt warm but never took temp
   2 if recorded a Temp: above normal but <99.5
   3 if recorded a Temp: 99.5 but <101
   4 if recorded a Temp: 101 but <103
   5 if recorded a Temp: 103 or higher 2. Constitutional Weight Loss
   0 if none
   1 if occurred but expected weight loss associated with current diet
   2 if not dieting but losing between 0 to 2% body weight per week
   3 if dieting but losing more weight than expected
   4 if losing >2% but <=4% body weight per week irrespective of diet
   5 if losing >4% body weight per week irrespective of diet 3. Constitutional Night Sweats
   0 if none
   1 if once in last 10 nights
   2 if >once in last 10 nights but <=every 3 nights
   3 if >once every 3 nights but <=once a night
   4 if every night but no change in bedclothes needed
   5 if every night & changing bedclothes needed 4. Constitutional Fatigue
   0 if none
   1 occurs but well explained by lack of sleep or vigorous exercise
   2 spontaneously occurs but <=2 times a week
   3 if occurs 2 or more times a week but <daily
   4 if complains of fatigue daily, but not all day long
   5 if constant fatigue 5. Constitutional Medical Compliance Self Assessment
   0 if always taking meds and never missing follow up (F/U) appointments
   1 if takes meds & keeps F/U visits but does not feel they are necessary
   2 if compliant with 75% but <100% of meds or F/U visits
   3 if compliant with 25% but <75% of meds or F/U visits
   4 if compliant with <25% of meds or F/U visits but does not refuse either
   5 if refuses medications and medical F/U visits 6. Endocrine Diabetes Mellitus
   0 if not diabetic
   1 if not diabetic but a sibling or parent is
   2 controlled (fasting BS<150 mg/dl or last HA1C<7.5%) & on no medicines for glucose control
   3 controlled (fasting BS<150 mg/dl or last HA1C<7.5%) but on medication for glucose control
   4 if keeps F/U visits but fasting BS between 150 to 250 (mg/dl) often or last HA1C between 7.5 to 9.5(%)
   5 if fasting BS>250 mg/dl or not checking fingersticks or HA1C>9.5% or no DM F/U visits 7. Pulmonary Cough
   0 if none
   1 if cough <once every 3 days
   2 if cough >=once every 3 days but not daily & cough considered tolerable to client
   3 if cough >=once every 3 days but not daily, & cough considered not tolerable to client
   4 if daily cough but does not feel like it is non-stop
   5 if feels like non-stop coughing 8. Pulmonary Oxygen Usage
   0 if not using it and never been advised to use it
   1 if advised to use as outpatient, >2 years passed since told no longer needed
   2 if advised to use as outpatient but told OK to stop between >3 months ago to 2 years ago
   3 if advised to use as outpatient but told OK to stop between 3 months ago to present
   4 told to use constantly and compliant with usage
   5 if told to use constantly but non compliant with usage 9. Pulmonary Short of Breath
   0 if never
   1 if short of breath once in last 10 days
   2 if short of breath once >3 days ago but <10 days ago
   3 if short of breath once <=3 days ago or daily, but not more than once a day
   4 if short of breath more than once a day but <5 times a day
   5 if short of breath 5 times a day or more 10. Pulmonary Respiratory Chest Wall or Shoulder Pain
    0 if none
    1 if noted with cough or deep breath but 5 days or more between episodes
    2 if noted with cough or deep breath every 5 days or less, but not daily 3 if noted with cough or deep breath, occurring daily, but tolerable to client
4 if noted with cough or deep breath, occurring daily, intolerable to client, not constant
5 if noting pain from cough or deep breath constantly throughout the day 11. Cardiovascular Palpitations
0 if none
1 if occurring but not more than once a month
2 if occurring but >once a month but <=once a week
3 if occurring >once a week but not daily
4 if occurring daily but not passing out
5 if ever passed out while having palpitations 12. Cardiovascular Angina
0 if none
1 if client told chest pain is not cardiac because of stress test or angiogram negative within last month
2 if followed in cardiology and no new nor worsening symptoms since last cardiology visit (stable angina)
3 if new or worsening chest pain intermittently at rest, none with activity
4 if new or worsening chest pain with activity relieved with rest
5 if currently experiencing new or worsening chest pain 13. Cardiovascular Relief of Presenting Symptom
0 if symptom is distal to elbow or below waist *Choices 1 to 5 assume symptom more proximal
1 if symptom resolves in <1 minute without anything
2 currently taking a long acting nitroglycerin product (Isordil Imdur or Nitropatch)
3 if up to ½ of events spontaneously resolve & ½ of events require nitroglycerin or oxygen
4 if more than ½ of the events require nitroglycerin or oxygen but symptoms are not constant
5 if symptoms are constant unless nitroglycerin or oxygen is used or persist despite NTG or O2

14. Cardiovascular Exercise Impact on Presenting Symptom
0 if symptom is distal to elbow or below waist *Choices 1 to 5 assume symptom more proximal
1 if symptom develops during rest after full exercise capacity
2 if symptom occurs @ maximal exercise capacity
3 if symptom occurs @ 50% or higher of maximal exercise capacity
4 if symptom occurs @ less than 50% of maximal exercise capacity but not immediately
5 if any exertional effort reproduces symptom nearly immediately 15. Gastrointestinal Control of Bowels
0 if complete control or longstanding continence problems proven benign by a workup
1 if new rectal leakage occurs but not more than once a month
2 if new rectal leakage occurs >once a month but <=once a week
3 if new rectal leakage occurs >once a week but not daily
4 if daily new rectal leakage but can wear same underwear throughout day
5 if daily new rectal leakage & change of underwear needed or protective padding used 16. Genitourinary Control of Urine
0 if complete control or longstanding continence problems proven benign by a workup
1 if new episodes of loss of control but not more than once a month
2 if new episodes of loss of control >once a month but <=once a week
3 if new episodes of loss of control >once a week but not daily
4 if daily new episodes of loss of control but can wear same underwear throughout day
5 if daily new episodes of loss of control & change of underwear needed or protective padding used 17. Neurologic Visual Loss
0 if none *Choices 1-5 are either in 1 eye or both
1 for <10 seconds and occurred over a month ago
2 if had a reversible episode >10 seconds but occurred >10 days ago
3 if had a reversible episode >10 seconds but occurred >3 days ago but <=10 days ago
4 if had a reversible episode >10 seconds but occurred <=3 days ago
5 if new onset visual loss that persists 18. Neurologic Visual Disturbance
0 if none *Choices 1-5 are either in 1 eye or both. Disturbance means spots or floaters not visual loss
1 for <10 seconds and occurred over a month ago
2 if had a reversible episode >10 seconds but occurred >10 days ago
3 if had a reversible episode >10 seconds but occurred >3 days ago but <=10 days ago
4 if had a reversible episode >10 seconds but occurred <=3 days ago
5 if new onset visual disturbance that persists 19. Neurologic Photophobia
0 if none. *Photophobia means exposure to light (such as indoors to outdoors) causes pain
1 for <10 seconds and occurred over a month ago
2 if had an episode >10 seconds but occurred >10 days ago
3 if had an episode >10 seconds but occurred >3 days ago but <=10 days ago
4 if had an episode >10 seconds but occurred <=3 days ago
5 if new onset photophobia that persists 20. Neurologic Hearing Loss
0 if none
1 for <10 seconds and occurred over a month ago
2 if had an episode >10 seconds but occurred >10 days ago
3 if had an episode >10 seconds but occurred >3 days ago but <=10 days ago
4 if had an episode >10 seconds but occurred <=3 days ago
5 if new onset hearing loss that persists 21. Neurologic Vertigo
0 if none
1 for <10 seconds and occurred over a month ago
2 if had an episode >10 seconds but occurred >10 days ago
3 if had an episode >10 seconds but occurred >3 days ago but <=10 days ago
4 if had an episode >10 seconds but occurred <=3 days ago
5 if new onset vertigo that persists 22. Neurologic Headache
0 if no new or worsening headache
1 if new or worsening headache <20 minutes and occurred over 2 weeks ago
2 if new or worsening headache lasting <20 minutes and occurred within 2 weeks
3 if new or worsening headache >=20 minutes but occurred >1 week ago 4 if new or worsening headache >=20 minutes but occurred within last week, currently headache free
5 if currently experiencing new or worsening headaches lasting >=20 minutes 23. Neurologic Frequency of Upper Extremity Change in Sensation
    0 if none *Note: Score 0 if due to previously evaluated stroke or injury and unchanged since that event
    1 if sensation change <10 minutes over last month
    2 if sensation change >=10 minutes over last month but <15 minutes a week
    3 if sensation change >=15 minutes a week but not daily
    4 if sensation change daily but not constant
    5 if constant sensation change 24. Neurologic Frequency of Upper Extremity Weakness
    0 if none *Note: Score 0 if due to previously evaluated stroke or injury and unchanged since that event
    1 if weakness occurred <10 minutes over last month
    2 if weakness occurred >=10 minutes over last month but <15 minutes a week
    3 if weakness occurred >=15 minutes a week but not daily
    4 if weakness occurs daily but not constant
    5 if constant sensation of weakness 25. Neurologic Extent of Upper Extremity Weakness
    0 if none *Note: Score 0 if due to previously evaluated stroke or injury and unchanged since that event
    1 if seems weak but no loss of function
    2 if noticing weakness (dropping things) but maintaining ADLs
    3 if noticing weakness and impacting ADLs but can push self away
    4 if able to move upper extremity but cannot push self away
    5 if unable to move upper extremity 26. Neurologic Frequency of Lower Extremity Change in Sensation
    0 if none *Note: Score 0 if due to previously evaluated stroke or injury and unchanged since that event
    1 if sensation change <10 minutes over last month
    2 if sensation change >=10 minutes over last month but <15 minutes a week
    3 if sensation change >=15 minutes a week but not daily
    4 if sensation change daily but not constant
    5 if constant sensation change 27. Neurologic Frequency of Lower Extremity Weakness
    0 if none *Note: Score 0 if due to previously evaluated stroke or injury and unchanged since that event
    1 if weakness occurred <10 minutes over last month
    2 if weakness occurred >=10 minutes over last month but <15 minutes a week
    3 if weakness occurred >=15 minutes a week but not daily
    4 if weakness occurs daily but not constant
    5 if constant sensation of weakness 28. Neurologic Extent of Lower Extremity Weakness
    0 if none *Note: Score 0 if due to previously evaluated stroke or injury and unchanged since that event
    1 if seems weak but no loss of function
    2 if noticing weakness while walking (stopping or shorter distances) but can walk without falling
    3 if noticing weakness will fall while walking or relying on wheelchair or other assisted mobility
    4 if able to move legs but cannot walk nor go from seated to standing
    5 if unable to move lower extremity 29. Rheumatological Rheumatoid Arthritis
    0 if none of the criteria
    1 if client knows +RF blood test, but not positive in any other criteria
    2 if up to 3 items of the RA criteria but for <6 weeks
    3 if up to 3 items of the RA criteria but for >=6 weeks
    4 if meet criteria, but client was not aware
    5 known diagnosis of RA 30. Hematological Immune Suppression
    0 if none *Note: Systemic steroids include Prednisone, Solumedrol, Kenalog, Depomedrol
    1 currently not immunosuppressed, but will take systemic steroids for <=1 week <=2 times a year
    2 currently not immunosuppressed but receives systemic steroids >2 times a year
    3 currently on systemic steroids or other immunosuppressants, but no transplant history & HIV negative
    4 HIV positive or transplant history
    5 known very low white blood cell count (WBC count <2) due to medical therapy or illness 31. Cervical Cervical Daytime Pain
    0 if none *Note: Responses 1-3 assume no analgesic medications are used
    1 if pain noted but none for >1 week
    2 if pain occurred <=1 week ago but lasts <½ of the day
    3 if pain occurred <=1 week ago but lasts >=½ of the day will resolve without analgesics
    4 if constant pain but resolves with analgesics
    5 constant pain, uncontrolled with analgesics 32. Cervical Cervical Nighttime Pain
    0 if none *Note: Responses 1-3 assume no analgesic medications are used
    1 able to sleep entire night once a comfortable position is found
    2 pain awakens due to positional change, but able to fall back asleep
    3 awaken often without attributing to positional change, can fall back asleep
    4 if having pain but able to sleep with analgesic medications
    5 if problems sleeping due to pain and analgesics do not improve situation 33. Cervical Cervical Extent of Pain Referral
    0 if no cervical pain
    1 if cervical pain, never referred
    2 pain refers away from neck but <one instance a week
    3 pain refers away from neck >=once a week but not daily
    4 if pain refers away from neck daily but can resolve with positional change
    5 if pain refers away from neck daily and cannot resolve with positional change 34. Cervical Cervical Quality of Pain
    0 if none
    1 if dull & no analgesics needed
    2 if dull & analgesics are used for relief
    3 if sharp & no analgesics are used
    4 if sharp & analgesics are used for relief
    5 if uncontrolled with analgesics, either dull or sharp 35. Cervical Cervical Pain Relieving Factors
    0 if no cervical pain *Note: Examples of head support—resting head in hands, against reclining chair
    1 if stopping activity relieves pain immediately without need for head support 2 if stopping activity with head support relieves pain immediately
3 if stopping activity resolves pain not immediately but within 3 minutes with or without head support
4 if stopping activity resolves pain after 3 minutes with or without head support
5 if constant pain unable to relieve by stopping activity or head support 36. Cervical Cervical Pain Precipitating Factors
0 if no cervical pain *Note: Specific cervical range of motion=flexion, extension or rotation
1 if only worse with specific cervical range of motion easily reproduced
2 if worse when sitting or standing without head support but not immediately
3 if worse when sitting or standing without head support, occurs immediately
4 if constant pain, no associated symptoms (nausea, photophobia, headache, fever)
5 if constant pain plus another symptom (nausea, photophobia, headache, fever)

37. Cervical Cervical Trauma
0 if no cervical pain *Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain 38. Cervical Cervical Paresthesia
0 if no cervical paresthesia
1 if localized to area of pain
2 if paresthetic ipsilateral cervical spine but not in area of pain
3 if paresthetic in one dermatome
4 if paresthetic to two ipsilateral dermatomes
5 if contralateral upper extremity or bilateral upper extremity paresthesia 39. Thoracic Thoracic Daytime Pain
0 if none *Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics 40. Thoracic Thoracic Nighttime Pain
0 if none *Note: Responses 1-3 assume no analgesic medications are used 1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation 41. Thoracic Thoracic Extent of Pain Referral
0 if no thoracic pain
1 if thoracic pain, never referred
2 pain refers away from back but <one instance a week
3 pain refers away from back >=once a week but not daily
4 if pain refers away from back daily but can resolve with positional change
5 if pain refers away from back daily and cannot resolve with positional change 42. Thoracic Thoracic Quality of Pain
0 if none
1 if dull & no analgesics needed
2 if dull & analgesics are used for relief
3 if sharp & no analgesics are used
4 if sharp & analgesics are used for relief
5 if uncontrolled with analgesics, either dull or sharp 43. Thoracic Thoracic Pain Relieving Factors
0 if no thoracic pain
1 if stopping aggravating activity relieves pain immediately no positional change needed
2 if stopping activity and a positional change, other than laying down relieves pain immediately
3 if need to lie down to relieve pain and pain resolves within 3 minutes
4 if laying down takes >=3 minutes to relieve pain
5 unable to relieve pain with change in position 44. Thoracic Thoracic Pain Precipitating Factors
0 if no thoracic pain
1 if worse only after clearly overusing back
2 if worse after activities which used to be tolerable
3 if worse after standing or walking but not immediately
4 if worse simply upon standing or walking, or worse after laying down
5 constant uncomfortable pain 45. Thoracic Thoracic Trauma
0 if no thoracic pain *Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain 46. Thoracic Thoracic Paresthesia
0 if no thoracic paresthesia
1 if localized to area of pain
2 if paresthetic in only one dermatome
3 if paresthetic to two ipsilateral dermatomes
4 if paresthetic in three ipsilateral dermatomes
5 if contralateral dermatome or bilateral paresthesia 47. Shoulder Shoulder Daytime Pain
   0 if none *Note: Responses 1-3 assume no analgesic medications are used
   1 if pain noted but none for >1 week
   2 if pain occurred <=1 week ago but lasts <½ of the day
   3 if pain occurred <=1 week ago but lasts >=½ of the day will resolve without analgesics
   4 if constant pain but resolves with analgesics
   5 constant pain, uncontrolled with analgesics 48. Shoulder Shoulder Nighttime Pain
   0 if no shoulder pain
   1 able to sleep entire night once a comfortable position is found
   2 pain awakens due to positional change, but able to fall back asleep
   3 awaken often without attributing to positional change, can fall back asleep
   4 constant if not for analgesics, able to sleep with medications
   5 constant unrelenting, uncontrolled by analgesics 49. Shoulder Shoulder quality of pain
   0 if none
   1 if dull & no analgesics needed
   2 if dull & analgesics are used for relief
   3 if sharp & no analgesics are used
   4 if sharp & analgesics are used for relief
   5 if sharp, uncontrolled with analgesics 50. Shoulder Shoulder Pain Relieving Factors
   0 if no shoulder pain *Note: IUE ipsilateral upper extremity
   1 if pain occurs only with activities involving IUE & resolve immediately when activity is discontinued
   2 if pain occurs only with activities involving IUE & does not resolve immediately but <3 minutes when activity is discontinued
   3 if pain occurs only with activities involving IUE & takes >=3 minutes to resolve when activity is discontinued
   4 if pain occurs without activities involving IUE but not constant pain
   5 if constant pain 51. Shoulder Shoulder Pain Precipitating Factors
   0 if no shoulder pain
   1 if only having pain when reaching overhead
   2 if pain free at rest pain occurs with specific range of motion able to continue all activities
   3 if pain free at rest pain occurs with specific range of motion limiting activities
   4 if pain at rest but not constant
   5 constant pain 52. Shoulder Shoulder Trauma
   0 if no shoulder pain *Note: Known incident means a recalled activity leading to the pain
   1 gradual onset of pain without known incident
   2 if after known incident and client felt medical care was not necessary and no medical evaluation performed
   3 if after known incident and client sought medical care >24 hours after known incident
   4 if after known incident and client sought medical care <=24 hours after known incident
   5 if no trauma or precipitating event but sudden onset severe pain 53. Elbow Elbow Daytime Pain
   0 if none *Note: Responses 1-3 assume no analgesic medications are used
   1 if pain noted but none for >1 week
   2 if pain occurred <=1 week ago but lasts <½ of the day
   3 if pain occurred <=1 week ago but lasts >=½ of the day will resolve without analgesics
   4 if constant pain but resolves with analgesics
   5 constant pain, uncontrolled with analgesics 54. Elbow Elbow Nighttime Pain
   0 if no elbow pain
   1 able to sleep entire night once a comfortable position is found
   2 pain awakens due to positional change, but able to fall back asleep
   3 awaken often without attributing to positional change, can fall back asleep
   4 constant if not for analgesics, able to sleep with medications
   5 constant unrelenting, uncontrolled by analgesics 55. Elbow Elbow Quality of Pain
   0 if none
   1 if dull & no analgesics needed
   2 if dull & analgesics are used for relief
   3 if sharp & no analgesics are used
   4 if sharp & analgesics are used for relief
   5 if sharp, uncontrolled with analgesics Applicants' cervical spine algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

In certain embodiments of Applicants' method, if the individual scored a 5 on any of the following factors, consider transfer to emergency medical care:

| 1 | 3 | 7 | 9 | 10 | 11 | 12 | 13 | 14 | 15 | 16 | 17 | 19 | 21 | 22 | 25 | 28 | 32 | 36 | 37 | 40 | 45 |
|---|---|---|---|----|----|----|----|----|----|----|----|----|----|----|----|----|----|----|----|----|----|

In certain embodiments of Applicants' method, if the individual scores a 5 on 2 or more of the following Evaluation Factors, refer to a physician immediately or emergency room.

| | | | | | | | | | | | | | | | | | |
|---|---|---|---|---|---|---|---|---|---|---|---|---|---|---|---|---|---|
| 31 | 33 | 34 | 35 | 38 | 39 | 41 | 42 | 43 | 46 | 47 | 48 | 49 | 50 | 51 | 52 | 53 | 54 | 55 |

In certain embodiments of Applicants' method, if the individual scored a 3 or higher on any of the following Evaluation Factors, refer to a physician with consult within 48 hours.

| | | | | | | | | | | | | | | | |
|---|---|---|---|---|---|---|---|---|---|---|---|---|---|---|---|
| 1 | 3 | 9 | 10 | 11 | 12 | 13 | 14 | 15 | 16 | 17 | 18 | 19 | 22 | 25 | 28 | 50 |

In certain embodiments of Applicants' method, if the individual scores a 3 or higher on 3 or more of the Evaluation Factors, refer to a physician with consult within 48 hours.

| | | | | | | | | | | | | | | | | | | | | | |
|---|---|---|---|---|---|---|---|---|---|---|---|---|---|---|---|---|---|---|---|---|---|
| 2 | 4 | 7 | 20 | 21 | 23 | 24 | 26 | 27 | 31 | 32 | 35 | 36 | 38 | 39 | 40 | 43 | 44 | 47 | 48 | 51 | 53 | 54 |

Ankle/Foot Algorithm

1. Constitutional Fever 0 if none
1 if felt warm but never took temp
2 if recorded a Temp: above normal but <99.5
3 if recorded a Temp: 99.5 but <101
4 if recorded a Temp: 101 but <103
5 if recorded a Temp: 103 or higher 2. Constitutional Weight loss 0 if none
1 if occurred but expected weight loss associated with current diet
2 if not dieting but losing between 0 to 2% body weight per week
3 if dieting but losing more weight than expected
4 if losing >2% but <=4% body weight per week irrespective of diet
5 if losing >4% body weight per week irrespective of diet 3. Constitutional Night sweats 0 if none
1 if once in last 10 nights
2 if >once in last 10 nights but <= every 3 nights
3 if >once every 3 nights but <= once a night
4 if every night but no change in bedclothes needed
5 if every night & changing bedclothes needed 4. Constitutional Medical compliance self assessment 0 if always taking meds and never missing follow up (F/U) appointments
1 if takes meds & keeps F/U visits but does not feel they are necessary
2 if compliant with 75% but <100% of meds or F/U visits
3 if compliant with 25% but <75% of meds or F/U visits
4 if compliant with <25% of meds or F/U visits but does not refuse either
5 if refuses medications and medical F/U visits 5. Endocrine Diabetes mellitus 0 if not diabetic
1 if not diabetic but a sibling or parent is
2 controlled (fasting BS <150 mg/dl or last HA1C <7.5%) & on no medicines for glucose control
3 controlled (fasting BS <150 mg/dl or last HA1C <7.5%) but on medication for glucose control
4 if keeps F/U visits but fasting BS between 150 to 250 (mg/dl) often or last HA1C between 7.5 to 9.5 (%)
5 if fasting BS >250 mg/dl or not checking fingersticks or HA1C >9.5% or no DM F/U visits -continued Ankle/Foot Algorithm 6. Neurologic Frequency of lower extremity change in sensation 0 if none * Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily
4 if sensation change daily but not constant
5 if constant sensation change 7. Neurologic Frequency of lower extremity weakness 0 if none * Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant
5 if constant sensation of weakness 8. Neurologic Extent of lower extremity weakness 0 if none * Note: Score 0 if due to previously evaluated stroke or injury and unchanged since that event
1 if seems weak but no loss of function
2 if noticing weakness while walking (stopping or shorter distances) but can walk without falling
3 if noticing weakness will fall while walking or relying on wheelchair or other assisted mobility
4 if able to move legs but cannot walk nor go from seated to standing
5 if unable to move lower extremity 9. Rheumatological Skin morphology 0 if none * Note: Morphology change implies telangiectasia, subcutaneous nodule, malar rash or discoid rash
1 if only 1 instance of morphology change & known for >1 year
2 if only 1 instance of morphology change but started within last year
3 if up to 3 morphology changes that are known for >1 year or 2 new morphology changes within last year
4 if 4 morphology changes, known for >1 year or 3 new morphology changes within last year
5 if all 4 morphology changes that are new within last year 10. Rheumatological Joint swelling 0 if not having joint swelling
1 if only one joint swells not greater than once a week
2 if multiple joints swell not greater than once a week
3 if one or more joints swell > once a week but not daily
4 if one or more joints swell daily but not constantly
5 if constant daily swelling of one or more joints 11. Rheumatological Joint stiffness 0 if not having joint stiffness
1 if only one joint is stiff but not greater than once a week
2 if multiple joints become stiff not greater than once a week
3 if one or more joints become stiff > once a week but not daily
4 if one or more joints become stiff daily but not constantly
5 if constant daily stiffness of one or more joints 12. Rheumatological Rheumatoid Arthritis 0 if none of the criteria
1 if client knows +RF blood test, but not positive in any other criteria
2 if up to 3 items of the RA criteria but for <6 weeks
3 if up to 3 items of the RA criteria but for >=6 weeks
4 if meet criteria, but client was not aware
5 known diagnosis of RA 13. Ankle and Foot Ankle and foot daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics -continued

Ankle/Foot Algorithm

14. Ankle and Foot Ankle and foot nighttime pain 0 if no ankle nor foot pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

15. Ankle and Foot Ankle and foot quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics

16. Ankle and Foot Ankle and foot vascular changes 0 if none
1 if cold occasionally no pain no ulcers & functional
2 if ischemic pain, no ulcers & functional
3 if one ulcer
4 several ulcers or threatened digits
5 previous auto-amputation or black necrotic digits

17. Ankle and Foot Ankle and foot contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <$\frac{1}{2}$ of the day
4 if >=$\frac{1}{2}$ of the day swollen or erythematous, but not constant
5 constantly swollen or erythematous

18. Ankle and Foot Ankle and foot trauma 0 if no ankle or foot pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

19. Knee Knee daytime pain 0 if none * Note: Responses 1-3 assume no analgesic medications are used
1 if pain noted but none for >1 week
2 if pain occurred <=1 week ago but lasts <$\frac{1}{2}$ of the day
3 if pain occurred <=1 week ago but lasts >=$\frac{1}{2}$ of the day will resolve without analgesics
4 if constant pain but resolves with analgesics
5 constant pain, uncontrolled with analgesics

20. Knee Knee nighttime pain 0 if no knee pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

21. Knee Knee quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics

22. Knee Knee trauma 0 if no knee pain * Note: Known incident means a recalled activity leading to the pain
1 gradual onset of pain without known incident
2 if after known incident and client felt medical care was not necessary and no medical evaluation performed -continued Ankle/Foot Algorithm 3  if after known incident and client sought medical care >24 hours after known incident
4  if after known incident and client sought medical care <=24 hours after known incident
5  if no trauma or precipitating event but sudden onset severe pain 23. Knee Knee contact quality 0  if no swelling nor erythema
1  if swollen or erythematous <15 minutes once a month
2  if swollen or erythematous >=15 minutes once a month but <15 minutes once a week
3  if swollen or erythematous >=15 minutes once a week but <½ of the day
4  if >=½ of the day swollen or erythematous, but not constant
5  constantly swollen or erythematous 24. Hip Hip daytime pain 0  if none * Note: Responses 1-3 assume no analgesic medications are used
1  if pain noted but none for >1 week
2  if pain occurred <=1 week ago but lasts <½ of the day
3  if pain occurred <=1 week ago but lasts >=½ of the day will resolve without analgesics
4  if constant pain but resolves with analgesics
5  constant pain, uncontrolled with analgesics 25. Hip Hip nighttime pain 0  if no hip pain
1  able to sleep entire night once a comfortable position is found
2  pain awakens due to positional change, but able to fall back asleep
3  awaken often without attributing to positional change, can fall back asleep
4  constant if not for analgesics, able to sleep with medications
5  constant unrelenting, uncontrolled by analgesics 26. Hip Hip quality of pain 0  if none
1  if dull & no analgesics needed
2  if dull & analgesics are used for relief
3  if sharp & no analgesics are used
4  if sharp & analgesics are used for relief
5  if sharp, uncontrolled with analgesics 27. Hip Hip trauma 0  if no hip pain * Note: Known incident means a recalled activity leading to the pain
1  gradual onset of pain without known incident
2  if after known incident and client felt medical care was not necessary and no medical evaluation performed
3  if after known incident and client sought medical care >24 hours after known incident
4  if after known incident and client sought medical care <=24 hours after known incident
5  if no trauma or precipitating event but sudden onset severe pain 28. Hip Hip contact quality 0  if no swelling nor erythema
1  if swollen or erythematous <15 minutes once a month
2  if swollen or erythematous >=15 minutes once a month but <15 minutes once a week
3  if swollen or erythematous >=15 minutes once a week but <½ of the day
4  if >=½ of the day swollen or erythematous, but not constant
5  constantly swollen or erythematous 29. Lumbosacral Lumbosacral trauma 0  if no lumbosacral pain * Note: Known incident means a recalled activity leading to the pain
1  gradual onset of pain without known incident
2  if after known incident and client felt medical care was not necessary and no medical evaluation performed
3  if after known incident and client sought medical care >24 hours after known incident
4  if after known incident and client sought medical care <=24 hours after known incident
5  if no trauma or precipitating event but sudden onset severe pain 30. Lumbosacral Lumbosacral paresthesia 0  if no lumbosacral pareshthesia
1  if localized to area of pain
2  if paresthetic in only one dermatome -continued Ankle/Foot Algorithm 3 if paresthetic to two ipsilateral dermatomes
4 if paresthetic in three ipsilateral dermatomes
5 if contralateral lower extremity or bilateral lower extremity paresthesia Applicants' ankle/foot algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

If the individual scored a 5 on any of the following Evaluation Factors, consider transfer to emergency medical care:

| 1 | 3 | 8 | 16 | 24 | 25 | 27 | 29 |
|---|---|---|----|----|----|----|----|

In certain embodiments of Applicants' method, if the individual scores a 5 on 4 or more of the following Evaluation Factors, refer to a physician immediately or emergency room.

| 17 | 19 | 20 | 21 | 22 | 23 | 26 | 28 | 30 |
|----|----|----|----|----|----|----|----|----|

If the individual scores a 3 on any of the following Evaluation Factors, refer to a physician with in 48 hours.

| 1 | 3 | 8 | 10 | 11 | 13 | 14 | 15 | 16 | 17 | 18 | 24 |
|---|---|---|----|----|----|----|----|----|----|----|----|

If the individual scored a 3 or higher on 3 or more of the following Evaluation Factors, refer to a physician with consult within 48 hours.

| 2 | 6 | 7 | 12 | 19 | 20 | 23 | 25 | 26 | 28 | 30 |
|---|---|---|----|----|----|----|----|----|----|----|

Knee Algorithm

1. Constitutional Fever 0 if none
1 if felt warm but never took temp
2 if recorded a Temp: above normal but <99.5
3 if recorded a Temp: 99.5 but <101
4 if recorded a Temp: 101 but <103
5 if recorded a Temp: 103 or higher 2. Constitutional Weight loss 0 if none
1 if occurred but expected weight loss associated with current diet
2 if not dieting but losing between 0 to 2% body weight per week
3 if dieting but losing more weight than expected
4 if losing >2% but <= 4% body weight per week irrespective of diet
5 if losing >4% body weight per week irrespective of diet 3. Constitutional Night sweats 0 if none
1 if once in last 10 nights
2 if > once in last 10 nights but <= every 3 nights
3 if > once every 3 nights but <= once a night
4 if every night but no change in bedclothes needed
5 if every night & changing bedclothes needed 4. Neurologic Frequency of lower extremity change in sensation 0 if none * Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily -continued Knee Algorithm 4 if sensation change daily but not constant
5 if constant sensation change

5. Neurologic Frequency of lower extremity weakness 0 if none * Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant
5 if constant sensation of weakness

6. Neurologic Extent of lower extremity weakness 0 if none * Note: Score 0 if due to previously evaluated stroke or injury and unchanged since that event
1 if seems weak but no loss of function
2 if noticing weakness while walking (stopping or shorter distances) but can walk without falling
3 if noticing weakness will fall while walking or relying on wheelchair or other assisted mobility
4 if able to move legs but cannot walk nor go from seated to standing
5 if unable to move lower extremity

7. Lumbosacral Lumbosacral trauma 0 if no lumbosacral pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

8. Lumbosacral Lumbosacral paresthesia 0 if no lumbosacral pareshthesia
1 if localized to area of pain
2 if paresthetic in only one dermatome
3 if paresthetic to two ipsilateral dermatomes
4 if paresthetic in three ipsilateral dermatomes
5 if contralateral lower extremity or bilateral lower extremity paresthesia

9. Knee Knee daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

10. Knee Knee nighttime pain 0 if no knee pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

11. Knee Knee quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics

12. Knee Knee trauma 0 if no knee pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident -continued

Knee Algorithm 4 if after known incident and client sought medical care <=24 hours after known incident
5 if no trauma or precipitating event but sudden onset severe pain

13. Knee Knee contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous

14. Ankle and Foot Ankle and foot daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

15. Ankle and Foot Ankle and foot nighttime pain 0 if no ankle nor foot pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

16. Ankle and Foot Ankle and foot quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics

17. Ankle and Foot Ankle and foot vascular changes 0 if none
1 if cold occasionally no pain no ulcers & functional
2 if ischemic pain, no ulcers & functional
3 if one ulcer
4 several ulcers or threatened digits
5 previous auto-amputation or black necrotic digits

18. Ankle and Foot Ankle and foot contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous

19. Ankle and Foot Ankle and foot trauma 0 if no ankle or foot pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

20. Hip Hip daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics -continued

Knee Algorithm

21. Hip Hip nighttime pain 0 if no hip pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

22. Hip Hip quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics

23. Hip Hip trauma 0 if no hip pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

24. Hip Hip contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous Applicants' knee algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

If the individual scored a 5 on any of the following Evaluation Factors, consider transfer to emergency medical care:

| 1 | 3 | 6 | 7 | 17 | 20 | 21 | 23 |
|---|---|---|---|----|----|----|----|

In certain embodiments of Applicants' method, if the individual scores a 5 on 4 or more of the following Evaluation Factors, refer to a physician immediately or emergency room.

| 8 | 9 | 10 | 11 | 12 | 13 | 18 | 22 | 24 |
|---|---|----|----|----|----|----|----|----|

If the individual scores a 3 on any of the following Evaluation Factors, refer to a physician with in 48 hours.

| 1 | 3 | 6 | 14 | 15 | 16 | 17 | 18 | 19 | 20 | 21 |
|---|---|---|----|----|----|----|----|----|----|----|

If the individual scored a 3 or higher on 3 or more of the following Evaluation Factors, refer to a physician with consult within 48 hours.

| 2 | 4 | 5 | 8 | 9 | 10 | 13 | 22 | 24 |
|---|---|---|---|---|----|----|----|----|

| Elbow Algorithm |
| --- |
| 1. Constitutional Fever |

0 if none
1 if felt warm but never took temp
2 if recorded a Temp: above normal but <99.5
3 if recorded a Temp: 99.5 but <101
4 if recorded a Temp: 101 but <103
5 if recorded a Temp: 103 or higher

| 2. Constitutional Weight loss |
| --- |

0 if none
1 if occurred but expected weight loss associated with current diet
2 if not dieting but losing between 0 to 2% body weight per week
3 if dieting but losing more weight than expected
4 if losing >2% but <=4% body weight per week irrespective of diet
5 if losing >4% body weight per week irrespective of diet

| 3. Constitutional Night sweats |
| --- |

0 if none
1 if once in last 10 nights
2 if > once in last 10 nights but <= every 3 nights
3 if > once every 3 nights but <= once a night
4 if every night but no change in bedclothes needed
5 if every night & changing bedclothes needed

| 4. Constitutional Medical compliance self assessment |
| --- |

0 if always taking meds and never missing follow up (F/U) appointments
1 if takes meds & keeps F/U visits but does not feel they are necessary
2 if compliant with 75% but <100% of meds or F/U visits
3 if compliant with 25% but <75% of meds or F/U visits
4 if compliant with <25% of meds or F/U visits but does not refuse either
5 if refuses medications and medical F/U visits

| 5. Endocrine Diabetes mellitus |
| --- |

0 if not diabetic
1 if not diabetic but a sibling or parent is
2 controlled (fasting BS <150 mg/dl or last HA1C<7.5%) & on no medicines for glucose control
3 controlled (fasting BS <150 mg/dl or last HA1C<7.5%) but on medication for glucose control
4 if keeps F/U visits but fasting BS between 150 to 250 (mg/dl) often or last HA1C between 7.5 to 9.5 (%)
5 if fasting BS >250 mg/dl or not checking fingersticks or HA1C>9.5% or no DM F/U visits

| 6. Cardiovascular Angina |
| --- |

0 if none
1 if client told chest pain is not cardiac because of stress test or angiogram negative within last month
2 if followed in cardiology and no new nor worsening symptoms since last cardiology visit (stable angina)
3 if new or worsening chest pain intermittently at rest, none with activity
4 if new or worsening chest pain with activity relieved with rest
5 if currently experiencing new or worsening chest pain

| 7. Cardiovascular Relief of presenting symptom |
| --- |

0 if symptom is distal to elbow or below waist * Choices 1 to 5 assume symptom more proximal
1 if symptom resolves in <1 minute without anything
2 currently taking a long acting nitroglycerin product (Isordil Imdur or Nitropatch)
3 if up to ½ of events spontaneously resolve & ½ of events require nitroglycerin or oxygen
4 if more than ½ of the events require nitroglycerin or oxygen but symptoms are not constant
5 if symptoms are constant unless nitroglycerin or oxygen is used or persist despite NTG or O2

| 8. Cardiovascular Exercise impact on presenting symptom |
| --- |

0 if symptom is distal to elbow or below waist * Choices 1 to 5 assume symptom more proximal
1 if symptom develops during rest after full exercise capacity
2 if symptom occurs @ maximal exercise capacity
3 if symptom occurs @ 50% or higher of maximal exercise capacity
4 if symptom occurs @ less than 50% of maximal exercise capacity but not immediately
5 if any exertional effort reproduces symptom nearly immediately -continued

Elbow Algorithm

9. Neurologic Frequency of upper extremity change in sensation 0 if none * Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily
4 if sensation change daily but not constant
5 if constant sensation change

10. Neurologic Frequency of upper extremity weakness 0 if none * Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant
5 if constant sensation of weakness

11. Neurologic Extent of upper extremity weakness 0 if none * Note: Score 0 if due to previously evaluated stroke or injury and unchanged since that event
1 if seems weak but no loss of function
2 if noticing weakness (dropping things) but maintaining ADLs
3 if noticing weakness and impacting ADLs but can push self away
4 if able to move upper extremity but cannot push self away
5 if unable to move upper extremity

12. Rheumatological Skin morphology 0 if none * Note: Morphology change implies telengecrasia, subcutaneous nodule, malar rash or discoid rash
1 if only 1 instance of morphology change & known for >1 year
2 if only 1 instance of morphology change but started within last year
3 if up to 3 morphology changes that are known for >1 year or 2 new morphology changes within last year
4 if 4 morphology changes, known for >1 year or 3 new morphology changes within last year
5 if all 4 morphology changes that are new within last year

13. Elbow Elbow daytime pain 0 if none * Note: Responses 1-3 assume no analgesic medications are used
1 if pain noted but none for >1 week
2 if pain occurred <=1 week ago but lasts <$\frac{1}{2}$ of the day
3 if pain occurred <=1 week ago but lasts >=$\frac{1}{2}$ of the day will resolve without analgesics
4 if constant pain but resolves with analgesics
5 constant pain, uncontrolled with analgesics

14. Elbow Elbow nighttime pain 0 if no elbow pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

15. Elbow Elbow trauma 0 if no elbow pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

16. Elbow Elbow quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics -continued

| Elbow Algorithm |
|---|
| 17. Elbow Elbow contact quality |

0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous

| 18. Cervical Cervical daytime pain |
|---|

0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

| 19. Cervical Cervical nighttime pain |
|---|

0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

| 20. Cervical Cervical extent of pain referral |
|---|

0 if no cervical pain
1 if cervical pain, never referred
2 pain refers away from neck but < one instance a week
3 pain refers away from neck >= once a week but not daily
4 if pain refers away from neck daily but can resolve with positional change
5 if pain refers away from neck daily and cannot resolve with positional change

| 21. Cervical Cervical quality of pain |
|---|

0 if none
1 if dull & no analgesics needed
2 if dull & analgesics are used for relief
3 if sharp & no analgesics are used
4 if sharp & analgesics are used for relief
5 if uncontrolled with analgesics, either dull or sharp

| 22. Cervical Cervical pain relieving factors |
|---|

0 if no cervical pain * Note: Examples of head support —resting head in hands, against reclining chair
1 if stopping activity relieves pain immediately without need for head support
2 if stopping activity with head support relieves pain immediately
3 if stopping activity resolves pain not immediately but within 3 minutes with or without head support
4 if stopping activity resolves pain after 3 minutes with or without head support
5 if constant pain unable to relieve by stopping activity or head support

| 23. Cervical Cervical pain precipitating factors |
|---|

0 if no cervical pain * Note: Specific cervical range of motion = flexion, extension or rotation
1 if only worse with specific cervical range of motion easily reproduced
2 if worse when sitting or standing without head support but not immediately
3 if worse when sitting or standing without head support, occurs immediately
4 if constant pain, no associated symptoms (nausea, photophobia, headache, fever)
5 if constant pain plus another symptom (nausea, photophobia, headache, fever)

| 24. Cervical Cervical trauma |
|---|

0 if no cervical pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain -continued

Elbow Algorithm

25. Cervical Cervical paresthesia 0 if no cervical paresthesia
1 if localized to area of pain
2 if paresthetic ipsilateral cervical spine but not in area of pain
3 if paresthetic in one dermatome
4 if paresthetic to two ipsilateral dermatomes
5 if contralateral upper extremity or bilateral upper extremity paresthesia

26. Shoulder Shoulder daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

27. Shoulder Shoulder nighttime pain 0 if no shoulder pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

28. Shoulder Shoulder quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics

29. Shoulder Shoulder pain relieving factors 0 if no shoulder pain * Note: IUE ipsilateral upper extremity
1 if pain occurs only with activities involving IUE & resolve immediately when activity is discontinued
2 if pain occurs only with activities involving IUE & does not resolve immediately but <3 minutes when activity is discontinued
3 if pain occurs only with activities involving IUE & takes >=3 minutes to resolve when activity is discontinued
4 if pain occurs without activities involving IUE but not constant pain
5 if constant pain

30. Shoulder Shoulder pain precipitating factors 0 if no shoulder pain
1 if only having pain when reaching overhead
2 if pain free at rest pain occurs with specific range of motion able to continue all activities
3 if pain free at rest pain occurs with specific range of motion limiting activities
4 if pain at rest but not constant
5 constant pain

31. Shoulder Shoulder trauma 0 if no shoulder pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

32. Shoulder Shoulder contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous -continued

Elbow Algorithm

33. Wrist and Hand Wrist and hand daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

34. Wrist and Hand Wrist and hand nighttime pain 0 if no wrist nor hand pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

35. Wrist and Hand Wrist and hand quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics

36. Wrist and Hand Wrist and hand contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous

37. Wrist and Hand Wrist and hand vascular changes 0 if none
1 if cold occasionally no pain no ulcers & functional
2 if ischemic pain, no ulcers & functional
3 if one ulcer
4 several ulcers or threatened digits
5 previous auto-amputation or black necrotic digits

38. Wrist and Hand Wrist and hand trauma 0 if no wrist or hand pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

39. Wrist and Hand Wrist and hand non-bony deformities 0 if none
1 if expected post-op changes which should go away
2 if abnormal without a diagnosis
3 if sclerodactyly, clubbing or Raynaud's but essentially fully functional
4 if sclerodactyly, clubbing or Raynaud's but limited functionality
5 if sclerodactyly, clubbing or Raynaud's but no function remaining

40. Wrist and Hand Wrist and hand bony deformities 0 if none
1 if expected post-op changes which should go away
2 if abnormal without a diagnosis
3 if connective tissue disease changes but essentially fully functional
4 if connective tissue disease changes but limited functionality
5 if connective tissue disease changes but no function remaining Applicants' elbow algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes.

In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

If the individual scored a 5 on any of the following Evaluation Factors, consider transfer to emergency medical care:

| 1 | 3 | 6 | 7 | 8 | 11 | 19 | 23 | 24 | 37 |
|---|---|---|---|---|----|----|----|----|----|

In certain embodiments of Applicants' method, if the individual scores a 5 on 4 or more of the following Evaluation Factors, refer to a physician immediately or emergency room.

| 14 | 15 | 16 | 18 | 20 | 21 | 22 | 25 | 26 | 27 | 28 | 29 | 30 | 31 | 36 |
|----|----|----|----|----|----|----|----|----|----|----|----|----|----|----|

If the individual scores a 3 on any of the following Evaluation Factors, refer to a physician with in 48 hours.

| 1 | 3 | 6 | 7 | 8 | 11 | 17 | 29 | 32 | 33 | 34 | 35 | 36 | 37 | 38 |
|---|---|---|---|---|----|----|----|----|----|----|----|----|----|----|

If the individual scored a 3 or higher on 3 or more of the following Evaluation Factors, refer to a physician with consult within 48 hours.

| 2 | 9 | 10 | 13 | 18 | 19 | 22 | 23 | 25 | 27 | 30 | 40 |
|---|---|----|----|----|----|----|----|----|----|----|----|

| Hand/Wrist Algorithm |
|---|
| 1. Constitutional Fever |
| 0 if none<br>1 if felt warm but never took temp<br>2 if recorded a Temp: above normal but <99.5<br>3 if recorded a Temp: 99.5 but <101<br>4 if recorded a Temp: 101 but <103<br>5 if recorded a Temp: 103 or higher |
| 2. Constitutional Weight loss |
| 0 if none<br>1 if occurred but expected weight loss associated with current diet<br>2 if not dieting but losing between 0 to 2% body weight per week<br>3 if dieting but losing more weight than expected<br>4 if losing >2% but <=4% body weight per week irrespective of diet<br>5 if losing >4% body weight per week irrespective of diet |
| 3. Constitutional Night sweats |
| 0 if none<br>1 if once in last 10 nights<br>2 if > once in last 10 nights but <= every 3 nights<br>3 if > once every 3 nights but <= once a night<br>4 if every night but no change in bedclothes needed<br>5 if every night & changing bedclothes needed |
| 4. Rheumatological Joint swelling |
| 0 if not having joint swelling<br>1 if only one joint swells not greater than once a week<br>2 if multiple joints swell not greater than once a week<br>3 if one or more joints swell > once a week but not daily<br>4 if one or more joints swell daily but not constantly<br>5 if constant daily swelling of one or more joints |
| 5. Rheumatological Joint stiffness |
| 0 if not having joint stiffness<br>1 if only one joint is stiff but not greater than once a week<br>2 if multiple joints become stiff not greater than once a week<br>3 if one or more joints become stiff > once a week but not daily<br>4 if one or more joints become stiff daily but not constantly<br>5 if constant daily stiffness of one or more joints |
| 6. Rheumatological Systemic Lupus Erythematosis |
| 0 if none of the criteria<br>1 if client knows +ANA blood test, but not positive in any other criteria<br>2 if meets 1 or 2 items of the SLE criteria (including ANA status)<br>3 if meeting 3, 4, or 5 items of SLE criteria (including ANA status)<br>4 if meets SLE criteria, but client was not aware<br>5 known diagnosis of SLE |

-continued

| Hand/Wrist Algorithm |
|---|
| 7. Rheumatological Rheumatoid Arthritis |

0 if none of the criteria
1 if client knows +RF blood test, but not positive in any other criteria
2 if up to 3 items of the RA criteria but for <6 weeks
3 if up to 3 items of the RA criteria but for >=6 weeks
4 if meet criteria, but client was not aware
5 known diagnosis of RA

| 8. Rheumatological Skin morphology |
|---|

0 if none *Note: Morphology change implies telangiectasia, subcutaneous nodule, malar rash or discoid rash
1 if only 1 instance of morphology change & known for >1 year
2 if only 1 instance of morphology change but started within last year
3 if up to 3 morphology changes that are known for >1 year or 2 new morphology changes within last year
4 if 4 morphology changes, known for >1 year or 3 new morphology changes within last year
5 if all 4 morphology changes that are new within last year

| 9. Rheumatological Sunlight effect on skin |
|---|

0 if no sunlight intolerance
1 if lifelong history of burning but no change in tolerance over last 10 years
2 change in tolerance - new onset of burning with >30 minutes midday sun exposure, used to tan easily
3 change in tolerance - will burn in <=30 minutes but not if sunscreen is applied
4 change in tolerance - burn easily even with sunscreen, but not avoiding the sunlight
5 change in tolerance - avoiding sunlight due to easily burning

| 10. Wrist and Hand Wrist and hand daytime pain |
|---|

0 if none *Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

| 11. Wrist and Hand Wrist and hand nighttime pain |
|---|

0 if no wrist nor hand pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

| 12. Wrist and Hand Wrist and hand quality of pain |
|---|

0 if none
1 if dull & no analgesics needed
2 if dull & analgesics are used for relief
3 if sharp & no analgesics are used
4 if sharp & analgesics are used for relief
5 if sharp, uncontrolled with analgesics

| 13. Wrist and Hand Wrist and hand contact quality |
|---|

0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous

| 14. Wrist and Hand Wrist and hand vascular changes |
|---|

0 if none
1 if cold occasionally no pain no ulcers & functional
2 if ischemic pain, no ulcers & functional
3 if one ulcer
4 several ulcers or threatened digits
5 previous auto-amputation or black necrotic digits

| 15. Wrist and Hand Wrist and hand trauma |
|---|

0 if no wrist or hand pain *Note: Known incident means a recalled activity leading to the pain
1 gradual onset of pain without known incident -continued

| Hand/Wrist Algorithm |
|---|

2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

16. Wrist and Hand Wrist and hand non-bony deformities 0 if none
1 if expected post-op changes which should go away
2 if abnormal without a diagnosis
3 if sclerodactyly, clubbing or Raynaud's but essentially fully functional
4 if sclerodactyly, clubbing or Raynaud's but limited functionality
5 if sclerodactyly, clubbing or Raynaud's but no function remaining

17. Wrist and Hand Wrist and hand bony deformities 0 if none
1 if expected post-op changes which should go away
2 if abnormal without a diagnosis
3 if connective tissue disease changes but essentially fully functional
4 if connective tissue disease changes but limited functionality
5 if connective tissue disease changes but no function remaining

18. Elbow Elbow daytime pain 0 if none *Note: Responses 1-3 assume no analgesic medications are used
1 if pain noted but none for >1 week
2 if pain occurred <=1 week ago but lasts <$\frac{1}{2}$ of the day
3 if pain occurred <=1 week ago but lasts >=$\frac{1}{2}$ of the day will resolve without analgesics
4 if constant pain but resolves with analgesics
5 constant pain, uncontrolled with analgesics

19. Elbow Elbow nighttime pain 0 if no elbow pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

20. Elbow Elbow trauma 0 if no elbow pain *Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

21. Elbow Elbow quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics

22. Elbow Elbow contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <$\frac{1}{2}$ of the day
4 if >=$\frac{1}{2}$ of the day swollen or erythematous, but not constant
5 constantly swollen or erythematous

23. Cervical Cervical daytime pain 0 if none *Note: Responses 1-3 assume no analgesic medications are used
1 if pain noted but none for >1 week
2 if pain occurred <=1 week ago but lasts <$\frac{1}{2}$ of the day
3 if pain occurred <=1 week ago but lasts >=$\frac{1}{2}$ of the day will resolve without analgesics -continued Hand/Wrist Algorithm 4 if constant pain but resolves with analgesics
5 constant pain, uncontrolled with analgesics 24. Cervical Cervical nighttime pain 0 if none *Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation 25. Cervical Cervical extent of pain referral 0 if no cervical pain
1 if cervical pain, never referred
2 pain refers away from neck but < one instance a week
3 pain refers away from neck >= once a week but not daily
4 if pain refers away from neck daily but can resolve with positional change
5 if pain refers away from neck daily and cannot resolve with positional change 26. Cervical Cervical quality of pain 0 if none
1 if dull & no analgesics needed
2 if dull & analgesics are used for relief
3 if sharp & no analgesics are used
4 if sharp & analgesics are used for relief
5 if uncontrolled with analgesics, either dull or sharp 27. Cervical Cervical pain relieving factors 0 if no cervical pain *Note: Examples of head support - resting head in hands, against reclining chair
1 if stopping activity relieves pain immediately without need for head support
2 if stopping activity with head support relieves pain immediately
3 if stopping activity resolves pain not immediately but within 3 minutes with or without head support
4 if stopping activity resolves pain after 3 minutes with or without head support
5 if constant pain unable to relieve by stopping activity or head support 28. Cervical Cervical pain precipitating factors 0 if no cervical pain *Note: Specific cervical range of motion = flexion, extension or rotation
1 if only worse with specific cervical range of motion easily reproduced
2 if worse when sitting or standing without head support but not immediately
3 if worse when sitting or standing without head support, occurs immediately
4 if constant pain, no associated symptoms (nausea, photophobia, headache, fever)
5 if constant pain plus another symptom (nausea, photophobia, headache, fever)

29. Cervical Cervical trauma 0 if no cervical pain *Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain 30. Cervical Cervical paresthesia 0 if no cervical paresthesia
1 if localized to area of pain
2 if paresthetic ipsilateral cervical spine but not in area of pain
3 if paresthetic in one dermatome
4 if paresthetic to two ipsilateral dermatomes
5 if contralateral upper extremity or bilateral upper extremity paresthesia Applicants' hand/wrist algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

If the individual scored a 5 on any of the following Evaluation Factors, consider transfer to emergency medical care:

| 1 | 3 | 14 | 24 | 28 | 29 |
|---|---|----|----|----|----|

In certain embodiments of Applicants' method, if the individual scores a 5 on 4 or more of the following Evaluation Factors, refer to a physician immediately or emergency room.

| 13 | 19 | 20 | 21 | 23 | 25 | 26 | 27 |
|----|----|----|----|----|----|----|----|

If the individual scores a 3 on any of the following Evaluation Factors, refer to a physician with in 48 hours.

| 1 | 3 | 4 | 5 | 10 | 11 | 12 | 13 | 14 | 15 | 22 | 23 |
|---|---|---|---|----|----|----|----|----|----|----|----|

If the individual scored a 3 or higher on 3 or more of the following Evaluation Factors, refer to a physician with consult within 48 hours.

| 2 | 6 | 7 | 9 | 17 | 18 | 24 | 27 | 28 |
|---|---|---|---|----|----|----|----|----|

If number 14 is a 2 or higher with ulceration present on digits, refer to a physician immediately. If there is no pulse or diminished blood flow with ulcerations present, consider transfer to an emergency room.

| Headache Algorithm |
|---|
| 1. Constitutional Fever |

0 if none
1 if felt warm but never took temp
2 if recorded a Temp: above normal but <99.5
3 if recorded a Temp: 99.5 but <101
4 if recorded a Temp: 101 but <103
5 if recorded a Temp: 103 or higher 2. Constitutional Weight loss 0 if none
1 if occurred but expected weight loss associated with current diet
2 if not dieting but losing between 0 to 2% body weight per week
3 if dieting but losing more weight than expected
4 if losing >2% but <=4% body weight per week irrespective of diet
5 if losing >4% body weight per week irrespective of diet 3. Constitutional Night sweats 0 if none
1 if once in last 10 nights
2 if > once in last 10 nights but <= every 3 nights
3 if > once every 3 nights but <= once a night
4 if every night but no change in bedclothes needed
5 if every night & changing bedclothes needed 4. Constitutional Sleep pattern 0 if no problems sleeping nor inappropriately falling asleep (eating, driving, during conversation)
1 if feels sleepy only with lack of sleep, no naps, no inappropriately falling asleep
2 if must have nap up to 3 times a week no inappropriately falling asleep
3 if must have nap or will fall asleep inappropriately
4 fall asleep inappropriately but <3 times a week
5 inappropriately falling asleep >=3 times a week 5. Constitutional Fatigue 0 if none
1 occurs but well explained by lack of sleep or vigorous exercise
2 spontaneously occurs but <=2 times a week
3 if occurs 2 or more times a week but < daily
4 if complains of fatigue daily, but not all day long
5 if constant fatigue 6. Constitutional Medical compliance self assessment 0 if always taking meds and never missing follow up (F/U) appointments
1 if takes meds & keeps F/U visits but does not feel they are necessary
2 if compliant with 75% but <100% of meds or F/U visits
3 if compliant with 25% but <75% of meds or F/U visits -continued

Headache Algorithm 4 if compliant with <25% of meds or F/U visits but does not refuse either
5 if refuses medications and medical F/U visits

7. Endocrine Diabetes mellitus 0 if not diabetic
1 if not diabetic but a sibling or parent is
2 controlled (fasting BS <150 mg/dl or last HA1C<7.5%) & on no medicines for glucose control
3 controlled (fasting BS <150 mg/dl or last HA1C<7.5%) but on medication for glucose control
4 if keeps F/U visits but fasting BS between 150 to 250 (mg/dl) often or last HA1C between 7.5 to 9.5 (%)
5 if fasting BS >250 mg/dl or not checking fingersticks or HA1C>9.5% or no DM F/U visits

8. Pulmonary Oxygen usage 0 if not using it and never been advised to use it
1 if advised to use as outpatient, >2 years passed since told no longer needed
2 if advised to use as outpatient but told OK to stop between >3 months ago to 2 years ago
3 if advised to use as outpatient but told OK to stop between 3 months ago to present
4 told to use constantly and compliant with usage
5 if told to use constantly but non compliant with usage

9. Pulmonary Short of breath 0 if never
1 if short of breath once in last 10 days
2 if short of breath once >3 days ago but <10 days ago
3 if short of breath once <=3 days ago or daily, but not more than once a day
4 if short of breath more than once a day but <5 times a day
5 if short of breath 5 times a day or more

10. Gastrointestinal Nausea 0 if none
1 if nauseated once every 5 days
2 if nauseated not daily but < every 5 days
3 if nauseated daily but <=3 times a day
4 if nauseated >3 times a day but not constantly nauseated
5 if constantly nauseated

11. Gastrointestinal Vomiting 0 if none
1 if vomiting once every 5 days
2 if vomiting not daily but < every 5 days
3 if vomiting daily but <=3 times a day
4 if vomiting >3 times a day but not constantly vomiting
5 if constantly vomiting

12. Gastrointestinal Control of bowels 0 if complete control or longstanding continence problems proven benign by a workup
1 if new rectal leakage occurs but not more than once a month
2 if new rectal leakage occurs > once a month but <= once a week
3 if new rectal leakage occurs > once a week but not daily
4 if daily new rectal leakage but can wear same underwear throughout day
5 if daily new rectal leakage & change of underwear needed or protective padding used

13. Genitourinary Control of urine 0 if complete control or longstanding continence problems proven benign by a workup
1 if new episodes of loss of control but not more than once a month
2 if new episodes of loss of control > once a month but <= once a week
3 if new episodes of loss of control > once a week but not daily
4 if daily new episodes of loss of control but can wear same underwear throughout day
5 if daily new episodes of loss of control & change of underwear needed or protective padding used

14. Cardiovascular Angina 0 if none
1 if client told chest pain is not cardiac because of stress test or angiogram negative within last month
2 if followed in cardiology and no new nor worsening symptoms since last cardiology visit (stable angina)
3 if new or worsening chest pain intermittently at rest, none with activity -continued

| Headache Algorithm |
| --- |

4 if new or worsening chest pain with activity relieved with rest
5 if currently experiencing new or worsening chest pain

15. Cardiovascular Relief of presenting symptom 0 if symptom is distal to elbow or below waist *Note: Choices 1 to 5 assume symptom more proximal
1 if symptom resolves in <1 minute without anything
2 currently taking a long acting nitroglycerin product (Isordil Imdur or Nitropatch)
3 if up to ½ of events spontaneously resolve & ½ of events require nitroglycerin or oxygen
4 if more than ½ of the events require nitroglycerin or oxygen but symptoms are not constant
5 if symptoms are constant unless nitroglycerin or oxygen is used or persist despite NTG or O2

16. Neurologic Visual loss 0 if none *Note: Choices 1-5 are either in 1 eye or both
1 for <10 seconds and occurred over a month ago
2 if had a reversible episode >10 seconds but occurred >10 days ago
3 if had a reversible episode >10 seconds but occurred >3 days ago but <=10 days ago
4 if had a reversible episode >10 seconds but occurred <=3 days ago
5 if new onset visual loss that persists

17. Neurologic Visual disturbance 0 if none *Note: Choices 1-5 are either in 1 eye or both. Disturbance means spots or floaters not visual loss
1 for <10 seconds and occurred over a month ago
2 if had a reversible episode >10 seconds but occurred >10 days ago
3 if had a reversible episode >10 seconds but occurred >3 days ago but <=10 days ago
4 if had a reversible episode >10 seconds but occurred <=3 days ago
5 if new onset visual disturbance that persists

18. Neurologic Diplopia 0 if never *Note: Another way to describe diplopia is double vision
1 for <10 seconds and occurred over a month ago
2 if had a reversible episode >10 seconds but occurred >10 days ago
3 if had a reversible episode >10 seconds but occurred >3 days ago but <=10 days ago
4 if had a reversible episode >10 seconds but occurred <=3 days ago
5 if new onset double vision that persists

19. Neurologic Photophobia 0 if none *Note: Photophobia means exposure to light (such as indoors to outdoors) causes pain
1 for <10 seconds and occurred over a month ago
2 if had an episode >10 seconds but occurred >10 days ago
3 if had an episode >10 seconds but occurred >3 days ago but <=10 days ago
4 if had an episode >10 seconds but occurred <=3 days ago
5 if new onset photophobia that persists

20. Neurologic Hearing loss 0 if none
1 for <10 seconds and occurred over a month ago
2 if had an episode >10 seconds but occurred >10 days ago
3 if had an episode >10 seconds but occurred >3 days ago but <=10 days ago
4 if had an episode >10 seconds but occurred <=3 days ago
5 if new onset hearing loss that persists

21. Neurologic Swallow coordination 0 if none
1 if had 1 difficulty swallowing episode and occurred over a month ago
2 if had 1 difficulty swallowing episode but occurred >10 days ago and <=1 month ago
3 if had 1 difficulty swallowing episode but occurred >3 days ago but <=10 days ago
4 if had 1 difficulty swallowing episode but occurred <=3 days ago but not constant
5 if constantly having difficulty swallowing episodes

22. Neurologic Vertigo 0 if none
1 for <10 seconds and occurred over a month ago
2 if had an episode >10 seconds but occurred >10 days ago
3 if had an episode >10 seconds but occurred >3 days ago but <=10 days ago -continued Headache Algorithm 4 if had an episode >10 seconds but occurred <=3 days ago
5 if new onset vertigo that persists

23. Neurologic Headache 0 if no new or worsening headache
1 if new or worsening headache <20 minutes and occurred over 2 weeks ago
2 if new or worsening headache lasting <20 minutes and occurred within 2 weeks
3 if new or worsening headache >=20 minutes but occurred >1 week ago
4 if new or worsening headache >=20 minutes but occurred within last week, currently headache free
5 if currently experiencing new or worsening headaches lasting >=20 minutes

24. Neurologic Frequency of upper extremity change in sensation 0 if none *Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily
4 if sensation change daily but not constant
5 if constant sensation change

25. Neurologic Frequency of upper extremity weakness 0 if none *Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant
5 if constant sensation of weakness

26. Neurologic Extent of upper extremity weakness 0 if none *Note: Score 0 if due to previously evaluated stroke or injury and unchanged since that event
1 if seems weak but no loss of function
2 if noticing weakness (dropping things) but maintaining ADLs
3 if noticing weakness and impacting ADLs but can push self away
4 if able to move upper extremity but cannot push self away
5 if unable to move upper extremity

27. Neurologic Frequency of lower extremity change in sensation 0 if none *Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily
4 if sensation change daily but not constant
5 if constant sensation change

28. Neurologic Frequency of lower extremity weakness 0 if none *Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant
5 if constant sensation of weakness

29. Neurologic Extent of lower extremity weakness 0 if none *Note: Score 0 if due to previously evaluated stroke or injury and unchanged since that event
unchanged since that event
1 if seems weak but no loss of function
2 if noticing weakness while walking (stopping or shorter distances) but can walk without falling
3 if noticing weakness will fall while walking or relying on wheelchair or other assisted mobility
4 if able to move legs but cannot walk nor go from seated to standing
5 if unable to move lower extremity

30. Cervical Cervical daytime pain 0 if none *Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics -continued

| Headache Algorithm |
|---|

31. Cervical Cervical nighttime pain

0 if none *Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

32. Cervical Cervical extent of pain referral

0 if no cervical pain
1 if cervical pain, never referred
2 pain refers away from neck but < one instance a week
3 pain refers away from neck >= once a week but not daily
4 if pain refers away from neck daily but can resolve with positional change
5 if pain refers away from neck daily and cannot resolve with positional change

33. Cervical Cervical quality of pain

0 if none
1 if dull & no analgesics needed
2 if dull & analgesics are used for relief
3 if sharp & no analgesics are used
4 if sharp & analgesics are used for relief
5 if uncontrolled with analgesics, either dull or sharp

34. Cervical Cervical pain relieving factors

0 if no cervical pain *Note: Examples of head support - resting head in hands, against reclining chair
1 if stopping aggravating activity relieves pain immediately without need for head support
2 if stopping activity with head support relieves pain immediately
3 if stopping activity resolves pain not immediately but within 3 minutes with or without head support
4 if stopping activity resolves pain after 3 minutes with or without head support
5 if constant pain unable to relieve by stopping activity or head support

35. Cervical Cervical pain precipitating factors

0 if no cervical pain *Note: Specific cervical range of motion = flexion, extension or rotation
1 if only worse with specific cervical range of motion easily reproduced
2 if worse when sitting or standing without head support but not immediately
3 if worse when sitting or standing without head support, occurs immediately
4 if constant pain, no associated symptoms (nausea, photophobia, headache, fever)
5 if constant pain plus another symptom (nausea, photophobia, headache, fever)

36. Cervical Cervical trauma

0 if no cervical pain *Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

37. Cervical Cervical paresthesia

0 if no cervical paresthesia
1 if localized to area of pain
2 if paresthetic ipsilateral cervical spine but not in area of pain
3 if paresthetic in one dermatome
4 if paresthetic to two ipsilateral dermatomes
5 if contralateral upper extremity or bilateral upper extremity paresthesia

38. Rheumatological Systemic Lupus Erythematosis

0 if none of the criteria
1 if client knows +ANA blood test, but not positive in any other criteria
2 if meets 1 or 2 items of the SLE criteria (including ANA status)
3 if meeting 3, 4, or 5 items of SLE criteria (including ANA status)
4 if meets SLE criteria, but client was not aware
5 known diagnosis of SLE

39. Rheumatological Rheumatoid Arthritis

0 if none of the criteria
1 if client knows +RF blood test, but not positive in any other criteria

| -continued |
|---|
| Headache Algorithm |

2 if up to 3 items of the RA criteria but for <6 weeks
3 if up to 3 items of the RA criteria but for >=6 weeks
4 if meet criteria, but client was not aware
5 known diagnosis of RA

40. Hematological Anemia 0 if not anemic
1 if known mild anemic disorder never requiring treatment
2 been anemic in past, completely resolved with known temporary explanation
3 been anemic in past, resolved but client was given no explanation for being anemic
4 if currently on medications for anemia, controlled with the meds
5 if regular blood transfusions necessary for survival

41. Hematological Immune suppression 0 if none *Note: Systemic steroids include Prednisone, Solumedrol, Kenalog, Depomedrol
1 currently not immunosuppressed, but will take systemic steroids for <=1 week <=2 times a year
2 currently not immunosuppressed but receives systemic steroids >2 times a year
3 currently on systemic steroids or other immunosuppressants, but no transplant history & HIV negative
4 HIV positive or transplant history
5 known very low white blood cell count (WBC count <2) due to medical therapy or illness

42. Hematological Bleeding tendency 0 if none *Note: Heparin and low-molecular weight heparin is by shot; warfarin = Coumadin
1 if taking aspirin or Plavix
2 if on heparin, low-molecular weight heparin or warfarin
3 if client carries a diagnosis as having potentially life threatening bleeding disease but no exacerbation
4 if new onset spontaneously bleeding, client can self-control
5 if new onset spontaneously bleeding which client is unable to self-control Applicants' headache algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

If the individual scored a 5 on any of the following Evaluation Factors, consider referral to emergency medical care:

| | | | | | | | | | | | | | | | | | | | |
|---|---|---|---|---|---|---|---|---|---|---|---|---|---|---|---|---|---|---|---|
| 1 | 3 | 9 | 11 | 12 | 13 | 14 | 15 | 16 | 18 | 19 | 22 | 23 | 26 | 29 | 31 | 35 | 36 | 42 | |

In certain embodiments of Applicants' method, if the individual scores a 5 on 2 or more of the following Evaluation Factors, refer to a physician immediately or to emergency care.

| | | | | | |
|---|---|---|---|---|---|
| 21 | 30 | 32 | 33 | 34 | 37 |

If the individual scores a 3 on any of the following Evaluation Factors, refer to a physician with in 48 hours.

| | | | | | | | | | | | | | |
|---|---|---|---|---|---|---|---|---|---|---|---|---|---|
| 1 | 3 | 4 | 9 | 10 | 14 | 15 | 16 | 17 | 18 | 19 | 21 | 26 | 29 | 40 |

If the individual scored a 3 or higher on 3 or more of the following Evaluation Factors, refer to a physician with consult within 48 hours.

| | | | | | | | | | | | | | | | | | |
|---|---|---|---|---|---|---|---|---|---|---|---|---|---|---|---|---|---|
| 2 | 5 | 11 | 12 | 13 | 20 | 22 | 23 | 24 | 25 | 27 | 28 | 30 | 31 | 34 | 35 | 37 | 42 |

Vertigo Algorithm

1. Constitutional Fever 0 if none
1 if felt warm but never took temp
2 if recorded a Temp: above normal but <99.5
3 if recorded a Temp: 99.5 but <101
4 if recorded a Temp: 101 but <103
5 if recorded a Temp: 103 or higher

2. Constitutional Weight loss 0 if none
1 if occurred but expected weight loss associated with current diet
2 if not dieting but losing between 0 to 2% body weight per week
3 if dieting but losing more weight than expected
4 if losing >2% but <=4% body weight per week irrespective of diet
5 if losing >4% body weight per week irrespective of diet

3. Constitutional Night sweats 0 if none
1 if once in last 10 nights
2 if > once in last 10 nights but <= every 3 nights
3 if > once every 3 nights but <= once a night
4 if every night but no change in bedclothes needed
5 if every night & changing bedclothes needed

4. Constitutional Sleep pattern 0 if no problems sleeping nor inappropriately falling asleep (eating, driving, during conversation)
1 if feels sleepy only with lack of sleep, no naps, no inappropriately falling asleep
2 if must have nap up to 3 times a week no inappropriately falling asleep
3 if must have nap or will fall asleep inappropriately
4 fall asleep inappropriately but <3 times a week
5 inappropriately falling asleep >=3 times a week

5. Constitutional Fatigue 0 if none
1 occurs but well explained by lack of sleep or vigorous exercise
2 spontaneously occurs but <=2 times a week
3 if occurs 2 or more times a week but < daily
4 if complains of fatigue daily, but not all day long
5 if constant fatigue

6. Constitutional Medical compliance self assessment 0 if always taking meds and never missing follow up (F/U) appointments
1 if takes meds & keeps F/U visits but does not feel they are necessary
2 if compliant with 75% but <100% of meds or F/U visits
3 if compliant with 25% but <75% of meds or F/U visits
4 if compliant with <25% of meds or F/U visits but does not refuse either
5 if refuses medications and medical F/U visits

7. Endocrine Diabetes mellitus 0 if not diabetic
1 if not diabetic but a sibling or parent is
2 controlled (fasting BS <150 mg/dl or last HA1C<7.5%) & on no medicines for glucose control
3 controlled (fasting BS <150 mg/dl or last HA1C<7.5%) but on medication for glucose control
4 if keeps F/U visits but fasting BS between 150 to 250 (mg/dl) often or last HA1C between 7.5 to 9.5 (%)
5 if fasting BS >250 mg/dl or not checking fingersticks or HA1C>9.5% or no DM F/U visits

8. Pulmonary Oxygen usage 0 if not using it and never been advised to use it
1 if advised to use as outpatient, >2 years passed since told no longer needed
2 if advised to use as outpatient but told OK to stop between >3 months ago to 2 years ago
3 if advised to use as outpatient but told OK to stop between 3 months ago to present -continued Vertigo Algorithm 4 told to use constantly and compliant with usage
5 if told to use constantly but non compliant with usage 9. Pulmonary Short of breath 0 if never
1 if short of breath once in last 10 days
2 if short of breath once >3 days ago but <10 days ago
3 if short of breath once <=3 days ago or daily, but not more than once a day
4 if short of breath more than once a day but <5 times a day
5 if short of breath 5 times a day or more 10. Gastrointestinal Nausea 0 if none
1 if nauseated once every 5 days
2 if nauseated not daily but < every 5 days
3 if nauseated daily but <=3 times a day
4 if nauseated >3 times a day but not constantly nauseated
5 if constantly nauseated 11. Gastrointestinal Vomiting 0 if none
1 if vomiting once every 5 days
2 if vomiting not daily but < every 5 days
3 if vomiting daily but <=3 times a day
4 if vomiting >3 times a day but not constantly vomiting
5 if constantly vomiting 12. Gastrointestinal Control of bowels 0 if complete control or longstanding continence problems proven benign by a workup
1 if new rectal leakage occurs but not more than once a month
2 if new rectal leakage occurs > once a month but <= once a week
3 if new rectal leakage occurs > once a week but not daily
4 if daily new rectal leakage but can wear same underwear throughout day
5 if daily new rectal leakage & change of underwear needed or protective padding Used 13. Genitourinary Control of urine 0 if complete control or longstanding continence problems proven benign by a workup
1 if new episodes of loss of control but not more than once a month
2 if new episodes of loss of control > once a month but <= once a week
3 if new episodes of loss of control > once a week but not daily
4 if daily new episodes of loss of control but can wear same underwear throughout day
5 if daily new episodes of loss of control & change of underwear needed or protective padding used 14. Cardiovascular Palpitations 0 if none
1 if occurring but not more than once a month
2 if occurring but > once a month but <= once a week
3 if occurring > once a week but not daily
4 if occurring daily but not passing out
5 if ever passed out while having palpitations 15. Cardiovascular Angina 0 if none
1 if client told chest pain is not cardiac because of stress test or angiogram negative within last month
2 if followed in cardiology and no new nor worsening symptoms since last cardiology visit (stable angina)
3 if new or worsening chest pain intermittently at rest, none with activity
4 if new or worsening chest pain with activity relieved with rest
5 if currently experiencing new or worsening chest pain 16. Cardiovascular Relief of presenting symptom 0 if symptom is distal to elbow or below waist * Note: Choices 1 to 5 assume symptom more proximal
1 if symptom resolves in <1 minute without anything
2 currently taking a long acting nitroglycerin product (Isordil Imdur or Nitropatch)
3 if up to ½ of events spontaneously resolve & ½ of events require nitroglycerin or oxygen -continued

Vertigo Algorithm 4 if more than ½ of the events require nitroglycerin or oxygen but symptoms are not constant
5 if symptoms are constant unless nitroglycerin or oxygen is used or persist despite NTG or O2

17. Cardiovascular Exercise impact on presenting symptom 0 if symptom is distal to elbow or below waist * Note. Choices 1 to 5 assume symptom more proximal
1 if symptom develops during rest after full exercise capacity
2 if symptom occurs @ maximal exercise capacity
3 if symptom occurs @ 50% or higher of maximal exercise capacity
4 if symptom occurs @ less than 50% of maximal exercise capacity but not immediately
5 if any exertional effort reproduces symptom nearly immediately

18. Neurologic Visual loss 0 if none * Note. Choices 1-5 are either in 1 eye or both
1 for <10 seconds and occurred over a month ago
2 if had a reversible episode >10 seconds but occurred >10 days ago
3 if had a reversible episode >10 seconds but occurred >3 days ago but <=10 days ago
4 if had a reversible episode >10 seconds but occurred <=3 days ago
5 if new onset visual loss that persists

19. Neurologic Visual disturbance 0 if none * Note: Choices 1-5 are either in 1 eye or both. Disturbance means spots or floaters not visual loss
1 for <10 seconds and occurred over a month ago
2 if had a reversible episode >10 seconds but occurred >10 days ago
3 if had a reversible episode >10 seconds but occurred >3 days ago but <=10 days ago
4 if had a reversible episode >10 seconds but occurred <=3 days ago
5 if new onset visual disturbance that persists

20. Neurologic Diplopia 0 if never * Note: Another way to describe diplopia is double vision
1 for <10 seconds and occurred over a month ago
2 if had a reversible episode >10 seconds but occurred >10 days ago
3 if had a reversible episode >10 seconds but occurred >3 days ago but <=10 days ago
4 if had a reversible episode >10 seconds but occurred <=3 days ago
5 if new onset double vision that persists

21. Neurologic Photophobia 0 if none * Note. Photophobia means exposure to light (such as indoors to outdoors) causes pain
1 for <10 seconds and occurred over a month ago
2 if had an episode >10 seconds but occurred >10 days ago
3 if had an episode >10 seconds but occurred >3 days ago but <=10 days ago
4 if had an episode >10 seconds but occurred <=3 days ago
5 if new onset photophobia that persists

22. Neurologic Hearing loss 0 if none
1 for <10 seconds and occurred over a month ago
2 if had an episode >10 seconds but occurred >10 days ago
3 if had an episode >10 seconds but occurred >3 days ago but <=10 days ago
4 if had an episode >10 seconds but occurred <=3 days ago
5 if new onset hearing loss that persists

23. Neurologic Swallow coordination 0 if none
1 if had 1 difficulty swallowing episode and occurred over a month ago
2 if had 1 difficulty swallowing episode but occurred >10 days ago and <=1 month ago
3 if had 1 difficulty swallowing episode but occurred >3 days ago but <=10 days ago
4 if had 1 difficulty swallowing episode but occurred <=3 days ago but not constant
5 if constantly having difficulty swallowing episodes

24. Neurologic Vertigo 0 if none
1 for <10 seconds and occurred over a month ago
2 if had an episode >10 seconds but occurred >10 days ago -continued

Vertigo Algorithm 3 if had an episode >10 seconds but occurred >3 days ago but <=10 days ago
4 if had an episode >10 seconds but occurred <=3 days ago
5 if new onset vertigo that persists

25. Neurologic Headache 0 if no new or worsening headache
1 if new or worsening headache <20 minutes and occurred over 2 weeks ago
2 if new or worsening headache lasting <20 minutes and occurred within 2 weeks
3 if new or worsening headache >=20 minutes but occurred >1 week ago
4 if new or worsening headache >=20 minutes but occurred within last week, currently headache free
5 if currently experiencing new or worsening headaches lasting >=20 minutes

26. Neurologic Frequency of upper extremity change in sensation 0 if none * Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily
4 if sensation change daily but not constant
5 if constant sensation change

27. Neurologic Frequency of upper extremity weakness 0 if none * Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant
5 if constant sensation of weakness

28. Neurologic Extent of upper extremity weakness 0 if none * Note: Score 0 if due to previously evaluated stroke or injury and unchanged since that event
1 if seems weak but no loss of function
2 if noticing weakness (dropping things) but maintaining ADLs
3 if noticing weakness and impacting ADLs but can push self away
4 if able to move upper extremity but cannot push self away
5 if unable to move upper extremity

29. Neurologic Frequency of lower extremity change in sensation 0 if none * Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily
4 if sensation change daily but not constant
5 if constant sensation change

30. Neurologic Frequency of lower extremity weakness 0 if none * Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant
5 if constant sensation of weakness

31. Neurologic Extent of lower extremity weakness 0 if none * Note: Score 0 if due to previously evaluated stroke or injury and unchanged since that event
1 if seems weak but no loss of function
2 if noticing weakness while walking (stopping or shorter distances) but can walk without falling
3 if noticing weakness will fall while walking or relying on wheelchair or other assisted mobility
4 if able to move legs but cannot walk nor go from seated to standing
5 if unable to move lower extremity

32. Cervical Cervical daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics -continued

Vertigo Algorithm

33. Cervical Cervical nighttime pain 0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

34. Cervical Cervical extent of pain referral 0 if no cervical pain
1 if cervical pain, never referred
2 pain refers away from neck but < one instance a week
3 pain refers away from neck >= once a week but not daily
4 if pain refers away from neck daily but can resolve with positional change
5 if pain refers away from neck daily and cannot resolve with positional change

35. Cervical Cervical quality of pain 0 if none
1 if dull & no analgesics needed
2 if dull & analgesics are used for relief
3 if sharp & no analgesics are used
4 if sharp & analgesics are used for relief
5 if uncontrolled with analgesics, either dull or sharp

36. Cervical Cervical pain relieving factors 0 if no cervical pain * Note: Examples of head support - resting head in hands, against reclining chair
1 if stopping aggravating activity relieves pain immediately without need for head support
2 if stopping activity with head support relieves pain immediately
3 if stopping activity resolves pain not immediately but within 3 minutes with or without head support
4 if stopping activity resolves pain after 3 minutes with or without head support
5 if constant pain unable to relieve by stopping activity or head support

37. Cervical Cervical pain precipitating factors 0 if no cervical pain * Note: Specific cervical range of motion = flexion, extension or rotation
1 if only worse with specific cervical range of motion easily reproduced
2 if worse when sitting or standing without head support but not immediately
3 if worse when sitting or standing without head support, occurs immediately
4 if constant pain, no associated symptoms (nausea, photophobia, headache, fever)
5 if constant pain plus another symptom (nausea, photophobia, headache, fever)

38. Cervical Cervical trauma 0 if no cervical pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

39. Cervical Cervical paresthesia 0 if no cervical paresthesia
1 if localized to area of pain
2 if paresthetic ipsilateral cervical spine but not in area of pain
3 if paresthetic in one dermatome
4 if paresthetic to two ipsilateral dermatomes
5 if contralateral upper extremity or bilateral upper extremity paresthesia

40. Shoulder Shoulder pain relieving factors 0 if no shoulder pain * Note: IUE ipsilateral upper extremity
1 if pain occurs only with activities involving IUE & resolve immediately when activity is discontinued
2 if pain occurs only with activities involving IUE & does not resolve immediately but <3 minutes when activity is discontinued
3 if pain occurs only with activities involving IUE & takes >=3 minutes to resolve when activity is discontinued
4 if pain occurs without activities involving IUE but not constant pain
5 if constant pain

-continued

Vertigo Algorithm

41. Shoulder Shoulder pain precipitating factors 0 if no shoulder pain
1 if only having pain when reaching overhead
2 if pain free at rest pain occurs with specific range of motion able to continue all activities
3 if pain free at rest pain occurs with specific range of motion limiting activities
4 if pain at rest but not constant
5 constant pain

42. Hematological Anemia 0 if not anemic
1 if known mild anemic disorder never requiring treatment
2 been anemic in past, completely resolved with known temporary explanation
3 been anemic in past, resolved but client was given no explanation for being anemic
4 if currently on medications for anemia, controlled with the meds
5 if regular blood transfusions necessary for survival

43. Hematological Immune suppression 0 if none * Note: Systemic steroids include Prednisone, Solumedrol, Kenalog, Depomedrol
1 currently not immunosuppressed, but will take systemic steroids for <=1 week <=2 times a year
2 currently not immunosuppressed but receives systemic steroids >2 times a year
3 currently on systemic steroids or other immunosuppressants, but no transplant history & HIV negative
4 HIV positive or transplant history
5 known very low white blood cell count (WBC count <2) due to medical therapy or illness

44. Hematological Bleeding tendency 0 if none * Note: Heparin and low-molecular weight heparin is by shot; warfarin = Coumadin
1 if taking aspirin or Plavix
2 if on heparin, low-molecular weight heparin or warfarin
3 if client carries a diagnosis as having potentially life threatening bleeding disease but no exacerbation
4 if new onset spontaneously bleeding, client can self-control
5 if new onset spontaneously bleeding which client is unable to self-control Applicants' vertigo algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

In certain embodiments of Applicants' method, if the individual scored a 5 on any of the following factors, consider transfer to emergency medical care:

| 1 | 3 | 9 | 11 | 12 | 13 | 14 | 15 | 16 | 17 | 18 | 20 | 21 | 24 | 25 | 28 | 31 | 33 | 37 | 38 | 44 |

In certain embodiments of Applicants' method, if the individual scores a 5 on 2 or more of the following Evaluation Factors, refer to a physician immediately or emergency room.

| 23 | 32 | 34 | 35 | 36 | 39 |
|----|----|----|----|----|----|

In certain embodiments of Applicants' method, if the individual scored a 3 or higher on any of the following Evaluation Factors, refer to a physician with consult within 48 hours.

| 1 | 3 | 4 | 9 | 10 | 11 | 14 | 15 | 16 | 17 | 18 | 19 | 20 | 21 | 23 | 28 | 31 | 40 | 41 |
|---|---|---|---|----|----|----|----|----|----|----|----|----|----|----|----|----|----|----|

In certain embodiments of Applicants' method, if the individual scores a 3 or higher on 3 or more of the Evaluation Factors, refer to a physician with consult within 48 hours.

| 2 | 5 | 12 | 13 | 22 | 24 | 25 | 26 | 27 | 29 | 30 | 32 | 33 | 36 | 37 | 39 | 44 |
|---|---|----|----|----|----|----|----|----|----|----|----|----|----|----|----|----|

| Hip Algorithm |
|---|
| 1. Constitutional Fever |

0 if none
1 if felt warm but never took temp
2 if recorded a Temp: above normal but <99.5
3 if recorded a Temp: 99.5 but <101
4 if recorded a Temp: 101 but <103
5 if recorded a Temp: 103 or higher

| 2. Constitutional Weight loss |
|---|

0 if none
1 if occurred but expected weight loss associated with current diet
2 if not dieting but losing between 0 to 2% body weight per week
3 if dieting but losing more weight than expected
4 if losing >2% but <=4% body weight per week irrespective of diet
5 if losing >4% body weight per week irrespective of diet

| 3. Constitutional Night sweats |
|---|

0 if none
1 if once in last 10 nights
2 if > once in last 10 nights but <= every 3 nights
3 if > once every 3 nights but <= once a night
4 if every night but no change in bedclothes needed
5 if every night & changing bedclothes needed

| 4. Neurologic Frequency of lower extremity change in sensation |
|---|

0 if none * Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily
4 if sensation change daily but not constant
5 if constant sensation change

| 5. Neurologic Frequency of lower extremity weakness |
|---|

0 if none * Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant -continued

| Hip Algorithm |
| --- |

5 if constant sensation of weakness

6. Neurologic Extent of lower extremity weakness

0 if none * Note: Score 0 if due to previously evaluated stroke or injury and unchanged since that event
1 if seems weak but no loss of function
2 if noticing weakness while walking (stopping or shorter distances) but can walk without falling
3 if noticing weakness will fall while walking or relying on wheelchair or other assisted mobility
4 if able to move legs but cannot walk nor go from seated to standing
5 if unable to move lower extremity

7. Hip Hip daytime pain

0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

8. Hip Hip nighttime pain

0 if no hip pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

9. Hip Hip quality of pain

0 if none
1 if dull & no analgesics needed
2 if dull & analgesics are used for relief
3 if sharp & no analgesics are used
4 if sharp & analgesics are used for relief
5 if sharp, uncontrolled with analgesics

10. Hip Hip trauma

0 if no hip pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

11. Hip Hip contact quality

0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous

12. Lumbosacral Lumbosacral daytime pain

0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

13. Lumbosacral Lumbosacral nighttime pain

0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

| Hip Algorithm |
| --- |
| 14. Lumbosacral Lumbosacral extent of pain referral |

0 if no lumbosacral pain
1 if lumbosacral pain, never referred
2 pain refers away from back but < one instance a week
3 pain refers away from back >= once a week but not daily
4 if pain refers away from back daily but can resolve with positional change
5 if pain refers away from back daily and cannot resolve with positional change

| 15. Lumbosacral Lumbosacral quality of pain |
| --- |

0 if none
1 if dull & no analgesics needed
2 if dull & analgesics are used for relief
3 if sharp & no analgesics are used
4 if sharp & analgesics are used for relief
5 if uncontrolled with analgesics, either dull or sharp

| 16. Lumbosacral Lumbosacral pain relieving factors |
| --- |

0 if no lumbosacral pain
1 if stopping aggravating activity relieves pain
2 must sit to relieve the pain
3 only laying down relieves pain
4 must sit & forward flex to relieve pain
5 unable to relieve pain with change in position

| 17. Lumbosacral Lumbosacral pain precipitating factors |
| --- |

0 if no lumbosacral pain
1 if worse only after clearly overusing back
2 if worse after activities which used to be tolerable
3 if worse after standing or walking but not immediately
4 if worse simply upon standing or walking, or worse after laying down
5 constant uncomfortable pain

| 18. Lumbosacral Lumbosacral trauma |
| --- |

0 if no lumbosacral pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

| 19. Lumbosacral Lumbosacral paresthesia |
| --- |

0 if no lumbosacral pareshthesia
1 if localized to area of pain
2 if paresthetic in only one dermatome
3 if paresthetic to two ipsilateral dermatomes
4 if paresthetic in three ipsilateral dermatomes
5 if contralateral lower extremity or bilateral lower extremity paresthesia

| 20. Knee Knee daytime pain |
| --- |

0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

| 21. Knee Knee nighttime pain |
| --- |

0 if no knee pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

| 22. Knee Knee quality of pain |
| --- |

0 if none
1 if dull & no analgesics needed
2 if dull & analgesics are used for relief
3 if sharp & no analgesics are used
4 if sharp & analgesics are used for relief
5 if sharp, uncontrolled with analgesics

| Hip Algorithm |
|---|
| 23. Knee Knee trauma |
| 0 if no knee pain * Note: Known incident means a recalled activity leading to the pain<br>1 gradual onset of pain without known incident<br>2 if after known incident and client felt medical care was not necessary and no medical evaluation performed<br>3 if after known incident and client sought medical care >24 hours after known incident<br>4 if after known incident and client sought medical care <=24 hours after known incident<br>5 if no trauma or precipitating event but sudden onset severe pain |
| 24. Knee Knee contact quality |
| 0 if no swelling nor erythema<br>1 if swollen or erythematous <15 minutes once a month<br>2 if swollen or erythematous >=15 minutes once a month but <15 minutes once a week<br>3 if swollen or erythematous >=15 minutes once a week but <½ of the day<br>4 if >=½ of the day swollen or erythematous, but not constant<br>5 constantly swollen or erythematous |

Applicant's hip algorithm further comprises the following referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

If the individual scored a 5 on any of the following Evaluation Factors, consider transfer to emergency medical care:

| 1 | 3 | 6 | 7 | 8 | 10 | 13 | 18 |
|---|---|---|---|---|---|---|---|

In certain embodiments of Applicants' method, if the individual scores a 5 on 4 or more of the following Evaluation Factors, refer to a physician immediately or emergency room.

| 9 | 11 | 12 | 14 | 15 | 16 | 17 | 19 | 20 | 21 | 22 | 23 | 24 |
|---|---|---|---|---|---|---|---|---|---|---|---|---|

If the individual scores a 3 on any of the following Evaluation Factors, refer to a physician with in 48 hours.

| 1 | 3 | 6 | 7 |
|---|---|---|---|

If the individual scored a 3 or higher on 3 or more of the following Evaluation Factors, refer to a physician with consult within 48 hours.

| 2 | 4 | 5 | 9 | 11 | 12 | 13 | 16 | 17 | 19 | 20 | 21 | 24 |
|---|---|---|---|---|---|---|---|---|---|---|---|---|

| Lumbar Spine Algorithm |
|---|
| 1. Constitutional Fever |
| 0 if none<br>1 if felt warm but never took temp<br>2 if recorded a Temp: above normal but <99.5<br>3 if recorded a Temp: 99.5 but <101<br>4 if recorded a Temp: 101 but <103<br>5 if recorded a Temp: 103 or higher |
| 2. Constitutional Weight loss |
| 0 if none<br>1 if occurred but expected weight loss associated with current diet<br>2 if not dieting but losing between 0 to 2% body weight per week<br>3 if dieting but losing more weight than expected |

-continued

Lumbar Spine Algorithm 4 if losing >2% but <=4% body weight per week irrespective of diet
5 if losing >4% body weight per week irrespective of diet

3. Constitutional Night sweats 0 if none
1 if once in last 10 nights
2 if > once in last 10 nights but <= every 3 nights
3 if > once every 3 nights but <= once a night
4 if every night but no change in bedclothes needed
5 if every night & changing bedclothes needed

4. Constitutional Fatigue 0 if none
1 occurs but well explained by lack of sleep or vigorous exercise
2 spontaneously occurs but <=2 times a week
3 if occurs 2 or more times a week but < daily
4 if complains of fatigue daily, but not all day long
5 if constant fatigue

5. Constitutional Medical compliance self assessment 0 if always taking meds and never missing follow up (F/U) appointments
1 if takes meds & keeps F/U visits but does not feel they are necessary
2 if compliant with 75% but <100% of meds or F/U visits
3 if compliant with 25% but <75% of meds or F/U visits
4 if compliant with <25% of meds or F/U visits but does not refuse either
5 if refuses medications and medical F/U visits

6. Endocrine Diabetes mellitus 0 if not diabetic
1 if not diabetic but a sibling or parent is
2 controlled (fasting BS <150 mg/dl or last HA1C<7.5%) & on no medicines for glucose control
3 controlled (fasting BS <150 mg/dl or last HA1C<7.5%) but on medication for glucose control
4 if keeps F/U visits but fasting BS between 150 to 250 (mg/dl) often or last HA1C between 7.5 to 9.5 (%)
5 if fasting BS >250 mg/dl or not checking fingersticks or HA1C>9.5% or no DM F/U visits

7. Gastrointestinal Vomiting 0 if none
1 if vomiting once every 5 days
2 if vomiting not daily but < every 5 days
3 if vomiting daily but <=3 times a day
4 if vomiting >3 times a day but not constantly vomiting
5 if constantly vomiting

8. Gastrointestinal Heartburn 0 if none * Note: NSAIDs stands for Non Steroidal Anti Inflammatory Drugs (Ibuprofen, aspirin-like meds)
1 if having heartburn <15 minutes a week & not on NSAIDs & not on meds for heartburn
2 if heartburn occurs >=15 minutes/week but < daily & not on NSAIDs & not on meds for heartburn
3 if not on meds for heartburn plus it started after using NSAIDs or if not on NSAIDs, daily but not constant
4 if taking meds to treat heartburn which may be controlled or refractory but not constant heartburn
5 if constant heartburn with or without meds

9. Gastrointestinal Stool color 0 if never had black nor bloody stools
1 if black or bloody stool once in last month
2 if black or bloody stools but occurring > once a month but < once a week
3 if black or bloody stools but occurring >= once a week but < every 2 days
4 if black or bloody stools but occurring every 2 days or more frequently but not 5 days in a row
5 if black or bloody stools for 5 days in a row or more

10. Gastrointestinal Stool volume 0 if no change from baseline or actually decreased
1 if client feels > baseline but <50% increase
2 if client feels 50% to <100% more than baseline
3 if client feels 100% to <200% more than baseline
4 if client feels 200% or higher but fully continent
5 if so excessive afraid of continence or if had incontinence -continued Lumbar Spine Algorithm 11. Gastrointestinal Stool consistency 0 if unchanged stools or well formed
1 if one loose stool but occurred over 7 days ago
2 if one loose stool >2 days ago but <7 days ago
3 if just one loose stool <=2 days ago
4 if daily loose stool but <=3 loose stools per day
5 if >3 loose stools per day 12. Gastrointestinal Control of bowels 0 if complete control or longstanding continence problems proven benign by a workup
1 if new rectal leakage occurs but not more than once a month
2 if new rectal leakage occurs > once a month but <= once a week
3 if new rectal leakage occurs > once a week but not daily
4 if daily new rectal leakage but can wear same underwear throughout day
5 if daily new rectal leakage & change of underwear needed or protective padding used 13. Gastrointestinal Constipation 0 if none or unchanged bowel habits
1 if felt constipated but not more than once a month
2 if felt constipated > once a month but <= once a week
3 if felt constipated > once a week but not daily
4 if feeling constipated daily but not taking meds for a bowel movement
5 if feeling constipated daily & needs meds for a bowel movement 14. Genitourinary Blood in urine 0 if none
1 if noted but not more than once a month
2 if noted > once a month but <= once a week
3 if noted > once a week but not daily
4 if noted daily but not constantly
5 if noted with every void 15. Genitourinary Control of urine 0 if complete control or longstanding continence problems proven benign by a workup
1 if new episodes of loss of control but not more than once a month
2 if new episodes of loss of control > once a month but <= once a week
3 if new episodes of loss of control > once a week but not daily
4 if daily new episodes of loss of control but can wear same underwear throughout day
5 if daily new episodes of loss of control & change of underwear needed or protective padding used 16. Genitourinary Urinary frequency 0 if no change from baseline
1 if increased frequency occurred but not more than once a month
2 if increased frequency occurs > once a month but <= once a week
3 if increased frequency occurs > once a week but not daily
4 if increased frequency occurs daily but not constantly
5 if increased frequency occurs constantly throughout the day 17. Neurologic Frequency of lower extremity change in sensation 0 if none * Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily
4 if sensation change daily but not constant
5 if constant sensation change 18. Neurologic Frequency of lower extremity weakness 0 if none * Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant
5 if constant sensation of weakness 19. Neurologic Extent of lower extremity weakness 0 if none * Note: Score 0 if due to previously evaluated stroke or injury and unchanged since that event
1 if seems weak but no loss of function -continued

Lumbar Spine Algorithm 2 if noticing weakness while walking (stopping or shorter distances) but can walk without falling
3 if noticing weakness will fall while walking or relying on wheelchair or other assisted mobility
4 if able to move legs but cannot walk nor go from seated to standing
5 if unable to move lower extremity

20. Rheumatological Skin morphology 0 if none * Note: Morphology change implies telangiectasia, subcutaneous nodule, malar rash or discoid rash
1 if only 1 instance of morphology change & known for >1 year
2 if only 1 instance of morphology change but started within last year
3 if up to 3 morphology changes that are known for >1 year or 2 new morphology changes within last year
4 if 4 morphology changes, known for >1 year or 3 new morphology changes within last year
5 if all 4 morphology changes that are new within last year

21. Hematological Immune suppression 0 if none * Note: Systemic steroids include Prednisone, Solumedrol, Kenalog, Depomedrol
1 currently not immunosuppressed, but will take systemic steroids for <=1 week <=2 times a year
2 currently not immunosuppressed but receives systemic steroids >2 times a year
3 currently on systemic steroids or other immunosuppressants, but no transplant history & HIV negative
4 HIV positive or transplant history
5 known very low white blood cell count (WBC count <2) due to medical therapy or illness

22. Lumbosacral Lumbosacral daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

23. Lumbosacral Lumbosacral nighttime pain 0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

24. Lumbosacral Lumbosacral extent of pain referral 0 if no lumbosacral pain
1 if lumbosacral pain, never referred
2 pain refers away from back but < one instance a week
3 pain refers away from back >= once a week but not daily
4 if pain refers away from back daily but can resolve with positional change
5 if pain refers away from back daily and cannot resolve with positional change

25. Lumbosacral Lumbosacral quality of pain 0 if none
1 if dull & no analgesics needed
2 if dull & analgesics are used for relief
3 if sharp & no analgesics are used
4 if sharp & analgesics are used for relief
5 if uncontrolled with analgesics, either dull or sharp

26. Lumbosacral Lumbosacral pain relieving factors 0 if no lumbosacral pain
1 if stopping aggravating activity relieves pain
2 must sit to relieve the pain
3 only laying down relieves pain
4 must sit & forward flex to relieve pain
5 unable to relieve pain with change in position

27. Lumbosacral Lumbosacral pain precipitating factors 0 if no lumbosacral pain
1 if worse only after clearly overusing back
2 if worse after activities which used to be tolerable
3 if worse after standing or walking but not immediately -continued Lumbar Spine Algorithm 4 if worse simply upon standing or walking, or worse after laying down
5 constant uncomfortable pain

28. Lumbosacral Lumbosacral trauma 0 if no lumbosacral pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

29. Lumbosacral Lumbosacral paresthesia 0 if no lumbosacral pareshthesia
1 if localized to area of pain
2 if paresthetic in only one dermatome
3 if paresthetic to two ipsilateral dermatomes
4 if paresthetic in three ipsilateral dermatomes
5 if contralateral lower extremity or bilateral lower extremity paresthesia

30. Thoracic Thoracic daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

31. Thoracic Thoracic nighttime pain 0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

32. Thoracic Thoracic extent of pain referral 0 if no thoracic pain
1 if thoracic pain, never referred
2 pain refers away from back but < one instance a week
3 pain refers away from back >= once a week but not daily
4 if pain refers away from back daily but can resolve with positional change
5 if pain refers away from back daily and cannot resolve with positional change

33. Thoracic Thoracic quality of pain 0 if none
1 if dull & no analgesics needed
2 if dull & analgesics are used for relief
3 if sharp & no analgesics are used
4 if sharp & analgesics are used for relief
5 if uncontrolled with analgesics, either dull or sharp

34. Thoracic Thoracic pain relieving factors 0 if no thoracic pain
1 if stopping aggravating activity relieves pain immediately no positional change needed
2 if stopping activity and a positional change, other than laying down relieves pain immediately
3 if need to lie down to relieve pain and pain resolves within 3 minutes
4 if laying down takes >=3 minutes to relieve pain
5 unable to relieve pain with change in position

35. Thoracic Thoracic pain precipitating factors 0 if no thoracic pain
1 if worse only after clearly overusing back
2 if worse after activities which used to be tolerable
3 if worse after standing or walking but not immediately
4 if worse simply upon standing or walking, or worse after laying down
5 constant uncomfortable pain

36. Thoracic Thoracic trauma 0 if no thoracic pain * Note: Known incident means a recalled activity leading to the pain -continued Lumbar Spine Algorithm 1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain 37. Thoracic Thoracic paresthesia 0 if no thoracic paresthesia
1 if localized to area of pain
2 if paresthetic in only one dermatome
3 if paresthetic to two ipsilateral dermatomes
4 if paresthetic in three ipsilateral dermatomes
5 if contralateral dermatome or bilateral paresthesia 38. Hip Hip daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics 39. Hip Hip nighttime pain 0 if no hip pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics 40. Hip Hip quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics 41. Hip Hip trauma 0 if no hip pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain 42. Hip Hip contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous Applicants' lumbar spine algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

In certain embodiments of Applicants' method, if the individual scored a 5 on any of the following factors, consider transfer to emergency medical care:

| | | | | | | | | | | | | | | |
|---|---|---|---|---|---|---|---|---|---|---|---|---|---|---|
| 1 | 3 | 7 | 9 | 12 | 14 | 15 | 16 | 19 | 23 | 28 | 31 | 36 | 38 | 39 | 41 |

In certain embodiments of Applicants' method, if the individual scores a 5 on 3 or more of the following Evaluation Factors, refer to a physician immediately or emergency room.

| | | | | | | | | | | | | | |
|---|---|---|---|---|---|---|---|---|---|---|---|---|---|
| 8 | 10 | 22 | 24 | 25 | 26 | 27 | 29 | 30 | 32 | 33 | 34 | 37 | 40 | 42 |

In certain embodiments of Applicants' method, if the individual scored a 3 or higher on any of the following Evaluation Factors, refer to a physician with consult within 48 hours.

| | | | | | | |
|---|---|---|---|---|---|---|
| 1 | 3 | 9 | 11 | 13 | 19 | 38 |

In certain embodiments of Applicants' method, if the individual scores a 3 or higher on 3 or more of the Evaluation Factors, refer to a physician with consult within 48 hours.

| | | | | | | | | | | | | | | | | | | | | |
|---|---|---|---|---|---|---|---|---|---|---|---|---|---|---|---|---|---|---|---|---|
| 2 | 4 | 7 | 8 | 10 | 12 | 14 | 15 | 16 | 17 | 18 | 22 | 23 | 26 | 27 | 29 | 30 | 31 | 34 | 35 | 39 | 40 | 42 |

| Pelvic/Sacrum Algorithm |
|---|
| 1. Constitutional Fever |
| 0 if none<br>1 if felt warm but never took temp<br>2 if recorded a Temp: above normal but <99.5<br>3 if recorded a Temp: 99.5 but <101<br>4 if recorded a Temp: 101 but <103<br>5 if recorded a Temp: 103 or higher |
| 2. Constitutional Weight loss |
| 0 if none<br>1 if occurred but expected weight loss associated with current diet<br>2 if not dieting but losing between 0 to 2% body weight per week<br>3 if dieting but losing more weight than expected<br>4 if losing >2% but <=4% body weight per week irrespective of diet<br>5 if losing >4% body weight per week irrespective of diet |
| 3. Constitutional Night sweats |
| 0 if none<br>1 if once in last 10 nights<br>2 if > once in last 10 nights but <= every 3 nights<br>3 if > once every 3 nights but <= once a night<br>4 if every night but no change in bedclothes needed<br>5 if every night & changing bedclothes needed |
| 4. Constitutional Fatigue |
| 0 if none<br>1 occurs but well explained by lack of sleep or vigorous exercise<br>2 spontaneously occurs but <=2 times a week<br>3 if occurs 2 or more times a week but < daily<br>4 if complains of fatigue daily, but not all day long<br>5 if constant fatigue |
| 5. Constitutional Medical compliance self assessment |
| 0 if always taking meds and never missing follow up (F/U) appointments<br>1 if takes meds & keeps F/U visits but does not feel they are necessary<br>2 if compliant with 75% but <100% of meds or F/U visits<br>3 if compliant with 25% but <75% of meds or F/U visits<br>4 if compliant with <25% of meds or F/U visits but does not refuse either<br>5 if refuses medications and medical F/U visits |
| 6. Gastrointestinal Stool color |
| 0 if never had black nor bloody stools<br>1 if black or bloody stool once in last month<br>2 if black or bloody stools but occurring > once a month but < once a week<br>3 if black or bloody stools but occurring >= once a week but < every 2 days<br>4 if black or bloody stools but occurring every 2 days or more frequently but not 5 days in a row<br>5 if black or bloody stools for 5 days in a row or more |

-continued

| Pelvic/Sacrum Algorithm |
|---|
| 7. Gastrointestinal Stool volume |

0 if no change from baseline or actually decreased
1 if client feels > baseline but <50% increase
2 if client feels 50% to <100% more than baseline
3 if client feels 100% to <200% more than baseline
4 if client feels 200% or higher but fully continent
5 if so excessive afraid of continence or if had incontinence

| 8. Gastrointestinal Stool consistency |
|---|

0 if unchanged stools or well formed
1 if one loose stool but occurred over 7 days ago
2 if one loose stool >2 days ago but <7 days ago
3 if just one loose stool <=2 days ago
4 if daily loose stool but <=3 loose stools per day
5 if >3 loose stools per day

| 9. Gastrointestinal Control of bowels |
|---|

0 if complete control or longstanding continence problems proven benign by a workup
1 if new rectal leakage occurs but not more than once a month
2 if new rectal leakage occurs > once a month but <= once a week
3 if new rectal leakage occurs > once a week but not daily
4 if daily new rectal leakage but can wear same underwear throughout day
5 if daily new rectal leakage & change of underwear needed or protective padding used

| 10. Gastrointestinal Constipation |
|---|

0 if none or unchanged bowel habits
1 if felt constipated but not more than once a month
2 if felt constipated > once a month but <= once a week
3 if felt constipated > once a week but not daily
4 if feeling constipated daily but not taking meds for a bowel movement
5 if feeling constipated daily & needs meds for a bowel movement

| 11. Genitourinary Blood in urine |
|---|

0 if none
1 if noted but not more than once a month
2 if noted > once a month but <= once a week
3 if noted > once a week but not daily
4 if noted daily but not constantly
5 if noted with every void

| 12. Genitourinary Control of urine |
|---|

0 if complete control or longstanding continence problems proven benign by a workup
1 if new episodes of loss of control but not more than once a month
2 if new episodes of loss of control > once a month but <= once a week
3 if new episodes of loss of control > once a week but not daily
4 if daily new episodes of loss of control but can wear same underwear throughout day
5 if daily new episodes of loss of control & change of underwear needed or protective padding used

| 13. Neurologic Frequency of lower extremity change in sensation |
|---|

0 if none * Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily
4 if sensation change daily but not constant
5 if constant sensation change

| 14. Neurologic Frequency of lower extremity weakness |
|---|

0 if none * Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant
5 if constant sensation of weakness

| 15. Neurologic Extent of lower extremity weakness |
|---|

0 if none * Note: Score 0 if due to previously evaluated stroke or injury and unchanged since that event
1 if seems weak but no loss of function -continued

| Pelvic/Sacrum Algorithm |
|---|

2 if noticing weakness while walking (stopping or shorter distances) but can walk without falling
3 if noticing weakness will fall while walking or relying on wheelchair or other assisted mobility
4 if able to move legs but cannot walk nor go from seated to standing
5 if unable to move lower extremity

16. Rheumatological Skin morphology 0 if none * Note: Morphology change implies telangiectasia, subcutaneous nodule, malar rash or discoid rash
1 if only 1 instance of morphology change & known for >1 year
2 if only 1 instance of morphology change but started within last year
3 if up to 3 morphology changes that are known for >1 year or 2 new morphology changes within last year
4 if 4 morphology changes, known for >1 year or 3 new morphology changes within last year
5 if all 4 morphology changes that are new within last year

17. Lumbosacral Lumbosacral daytime pain 0 if none * Note: Responses 1-3 assume no analgesic medications are used
1 if pain noted but none for >1 week
2 if pain occurred <=1 week ago but lasts <$\frac{1}{2}$ of the day
3 if pain occurred <=1 week ago but lasts >=$\frac{1}{2}$ of the day will resolve without analgesics
4 if constant pain but resolves with analgesics
5 constant pain, uncontrolled with analgesics

18. Lumbosacral Lumbosacral nighttime pain 0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

19. Lumbosacral Lumbosacral extent of pain referral 0 if no lumbosacral pain
1 if lumbosacral pain, never referred
2 pain refers away from back but < one instance a week
3 pain refers away from back >= once a week but not daily
4 if pain refers away from back daily but can resolve with positional change
5 if pain refers away from back daily and cannot resolve with positional change

20. Lumbosacral Lumbosacral quality of pain 0 if none
1 if dull & no analgesics needed
2 if dull & analgesics are used for relief
3 if sharp & no analgesics are used
4 if sharp & analgesics are used for relief
5 if uncontrolled with analgesics, either dull or sharp

21. Lumbosacral Lumbosacral pain relieving factors 0 if no lumbosacral pain
1 if stopping aggravating activity relieves pain
2 must sit to relieve the pain
3 only laying down relieves pain
4 must sit & forward flex to relieve pain
5 unable to relieve pain with change in position

22. Lumbosacral Lumbosacral pain precipitating factors 0 if no lumbosacral pain
1 if worse only after clearly overusing back
2 if worse after activities which used to be tolerable
3 if worse after standing or walking but not immediately
4 if worse simply upon standing or walking, or worse after laying down
5 constant uncomfortable pain

23. Lumbosacral Lumbosacral trauma 0 if no lumbosacral pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident -continued

Pelvic/Sacrum Algorithm 4 if after known incident and client sought medical care <=24 hours after known incident
5 if no trauma or precipitating event but sudden onset severe pain

24. Lumbosacral Lumbosacral paresthesia 0 if no lumbosacral pareshthesia
1 if localized to area of pain
2 if paresthetic in only one dermatome
3 if paresthetic to two ipsilateral dermatomes
4 if paresthetic in three ipsilateral dermatomes
5 if contralateral lower extremity or bilateral lower extremity paresthesia

25. Hip Hip daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

26. Hip Hip nighttime pain 0 if no hip pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

27. Hip Hip quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics

28. Hip Hip trauma 0 if no hip pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

29. Hip Hip contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous

30. Knee Knee daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=1/2 of the day will resolve without analgesics
4 if constant pain but resolves with analgesics
5 constant pain, uncontrolled with analgesics

31. Knee Knee nighttime pain 0 if no knee pain
1 able to sleep entire night once a comfortable position is found
2 pain awakens due to positional change, but able to fall back asleep

| -continued |
|---|
| Pelvic/Sacrum Algorithm |

3 awaken often without attributing to positional change, can fall back asleep
4 constant if not for analgesics, able to sleep with medications
5 constant unrelenting, uncontrolled by analgesics 32. Knee Knee quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics 33. Knee Knee trauma 0 if no knee pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain 34. Knee Knee contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous Applicants' pelvic/sacrum algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

In certain embodiments of Applicants' method, if the individual scored a 5 on any of the following factors, consider transfer to emergency medical care:

| 1 | 3 | 6 | 9 | 11 | 12 | 15 | 18 | 23 | 25 | 26 | 28 |

In certain embodiments of Applicants' method, if the individual scores a 5 on 4 or more of the following Evaluation Factors, refer to a physician immediately or emergency room.

| 7 | 17 | 19 | 20 | 21 | 22 | 24 | 27 | 29 | 30 | 31 | 32 | 37 | 34 |

In certain embodiments of Applicants' method, if the individual scored a 3 or higher on any of the following Evaluation Factors, refer to a physician with consult within 48 hours.

| 1 | 3 | 6 | 8 | 10 | 15 | 25 |

In certain embodiments of Applicants' method, if the individual scores a 3 or higher on 3 or more of the Evaluation Factors, refer to a physician with consult within 48 hours.

| 2 | 4 | 7 | 9 | 11 | 12 | 13 | 14 | 17 | 18 | 21 | 22 | 24 | 26 | 27 | 29 | 30 | 31 | 34 |

| Shoulder Algorithm |
| --- |
| 1. Constitutional Fever |

0 if none
1 if felt warm but never took temp
2 if recorded a Temp: above normal but <99.5
3 if recorded a Temp: 99.5 but <101
4 if recorded a Temp: 101 but <103
5 if recorded a Temp: 103 or higher

| 2. Constitutional Weight loss |
| --- |

0 if none
1 if occurred but expected weight loss associated with current diet
2 if not dieting but losing between 0 to 2% body weight per week
3 if dieting but losing more weight than expected
4 if losing >2% but <=4% body weight per week irrespective of diet
5 if losing >4% body weight per week irrespective of diet

| 3. Constitutional Night sweats |
| --- |

0 if none
1 if once in last 10 nights
2 if > once in last 10 nights but <= every 3 nights
3 if > once every 3 nights but <= once a night
4 if every night but no change in bedclothes needed
5 if every night & changing bedclothes needed

| 4. Constitutional Fatigue |
| --- |

0 if none
1 occurs but well explained by lack of sleep or vigorous exercise
2 spontaneously occurs but <=2 times a week
3 if occurs 2 or more times a week but < daily
4 if complains of fatigue daily, but not all day long
5 if constant fatigue

| 5. Constitutional Medical compliance self assessment |
| --- |

0 if always taking meds and never missing follow up (F/U) appointments
1 if takes meds & keeps F/U visits but does not feel they are necessary
2 if compliant with 75% but <100% of meds or F/U visits
3 if compliant with 25% but <75% of meds or F/U visits
4 if compliant with <25% of meds or F/U visits but does not refuse either
5 if refuses medications and medical F/U visits

| 6. Endocrine Diabetes mellitus |
| --- |

0 if not diabetic
1 if not diabetic but a sibling or parent is
2 controlled (fasting BS <150 mg/dl or last HA1C<7.5%) & on no medicines for glucose control
3 controlled (fasting BS <150 mg/dl or last HA1C<7.5%) but on medication for glucose control
4 if keeps F/U visits but fasting BS between 150 to 250 (mg/dl) often or last HA1C between 7.5 to 9.5 (%)
5 if fasting BS >250 mg/dl or not checking fingersticks or HA1C>9.5% or no DM F/U visits

| 7. Pulmonary Cough |
| --- |

0 if none
1 if cough < once every 3 days
2 if cough >= once every 3 days but not daily & cough considered tolerable to client
3 if cough >= once every 3 days but not daily, & cough considered not tolerable to client
4 if daily cough but does not feel like it is non-stop
5 if feels like non-stop coughing

| 8. Pulmonary Oxygen usage |
| --- |

0 if not using it and never been advised to use it
1 if advised to use as outpatient, >2 years passed since told no longer needed
2 if advised to use as outpatient but told OK to stop between >3 months ago to 2 years ago
3 if advised to use as outpatient but told OK to stop between 3 months ago to present
4 told to use constantly and compliant with usage
5 if told to use constantly but non compliant with usage

| 9. Pulmonary Short of breath |
| --- |

0 if never
1 if short of breath once in last 10 days
2 if short of breath once >3 days ago but <10 days ago -continued

| Shoulder Algorithm |
| --- |

3 if short of breath once <=3 days ago or daily, but not more than once a day
4 if short of breath more than once a day but <5 times a day
5 if short of breath 5 times a day or more

10. Pulmonary Respiratory chest wall or shoulder pain 0 if none
1 if noted with cough or deep breath but 5 days or more between episodes
2 if noted with cough or deep breath every 5 days or less, but not daily
3 if noted with cough or deep breath, occurring daily, but tolerable to client
4 if noted with cough or deep breath, occurring daily, intolerable to client, not constant
5 if noting pain from cough or deep breath constantly throughout the day

11. Cardiovascular Palpitations 0 if none
1 if occurring but not more than once a month
2 if occurring but > once a month but <= once a week
3 if occurring > once a week but not daily
4 if occurring daily but not passing out
5 if ever passed out while having palpitations

12. Cardiovascular Angina 0 if none
1 if client told chest pain is not cardiac because of stress test or angiogram negative within last month
2 if followed in cardiology and no new nor worsening symptoms since last cardiology visit (stable angina)
3 if new or worsening chest pain intermittently at rest, none with activity
4 if new or worsening chest pain with activity relieved with rest
5 if currently experiencing new or worsening chest pain

13. Cardiovascular Relief of presenting symptom 0 if symptom is distal to elbow or below waist * Choices 1 to 5 assume symptom more proximal
1 if symptom resolves in <1 minute without anything
2 currently taking a long acting nitroglycerin product (Isordil Imdur or Nitropatch)
3 if up to ½ of events spontaneously resolve & ½ of events require nitroglycerin or oxygen
4 if more than ½ of the events require nitroglycerin or oxygen but symptoms are not constant
5 if symptoms are constant unless nitroglycerin or oxygen is used or persist despite NTG or O2

14. Cardiovascular Exercise impact on presenting symptom 0 if symptom is distal to elbow or below waist * Choices 1 to 5 assume symptom more proximal
1 if symptom develops during rest after full exercise capacity
2 if symptom occurs @ maximal exercise capacity
3 if symptom occurs @ 50% or higher of maximal exercise capacity
4 if symptom occurs @ less than 50% of maximal exercise capacity but not immediately
5 if any exertional effort reproduces symptom nearly immediately

15. Gastrointestinal Heartburn 0 if none * Note: NSAIDs stands for Non Steroidal Anti Inflammatory Drugs (Ibuprofen, aspirin-like meds)
1 if having heartburn <15 minutes a week & not on NSAIDs & not on meds for heartburn
2 if heartburn occurs >=15 minutes/week but < daily & not on NSAIDs & not on meds for heartburn
3 if not on meds for heartburn plus it started after using NSAIDs or if not on NSAIDs, daily but not constant
4 if taking meds to treat heartburn which may be controlled or refractory but not constant heartburn
5 if constant heartburn with or without meds

16. Neurologic Frequency of upper extremity change in sensation 0 if none * Note: Score 0 if due to previously evaluated stroke or injury and unchanged since that event
1 if sensation change <10 minutes over last month
2 if sensation change >=10 minutes over last month but <15 minutes a week
3 if sensation change >=15 minutes a week but not daily
4 if sensation change daily but not constant
5 if constant sensation change -continued

| Shoulder Algorithm |
|---|

17. Neurologic Frequency of upper extremity weakness 0 if none * Note: Score 0 if due to previously evaluated stroke or injury and unchanged since that event
1 if weakness occurred <10 minutes over last month
2 if weakness occurred >=10 minutes over last month but <15 minutes a week
3 if weakness occurred >=15 minutes a week but not daily
4 if weakness occurs daily but not constant
5 if constant sensation of weakness

18. Neurologic Extent of upper extremity weakness 0 if none * Note: Score 0 if due to previously evaluated stroke or injury and unchanged since that event
1 if seems weak but no loss of function
2 if noticing weakness (dropping things) but maintaining ADLs
3 if noticing weakness and impacting ADLs but can push self away
4 if able to move upper extremity but cannot push self away
5 if unable to move upper extremity

19. Rheumatological Skin morphology 0 if none * Note: Morphology change implies telengecrasia, subcutaneous nodule, malar rash or discoid rash
1 if only 1 instance of morphology change & known for >1 year
2 if only 1 instance of morphology change but started within last year
3 if up to 3 morphology changes that are known for >1 year or 2 new morphology changes within last year
4 if 4 morphology changes, known for >1 year or 3 new morphology changes within last year
5 if all 4 morphology changes that are new within last year

20. Shoulder Shoulder daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

21. Shoulder Shoulder nighttime pain 0 if no shoulder pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

22. Shoulder Shoulder quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics

23. Shoulder Shoulder pain relieving factors 0 if no shoulder pain * Note: IUE ipsilateral upper extremity
1 if pain occurs only with activities involving IUE & resolve immediately when activity is discontinued
2 if pain occurs only with activities involving IUE & does not resolve immediately but <3 minutes when activity is discontinued
3 if pain occurs only with activities involving IUE & takes >=3 minutes to resolve when activity is discontinued
4 if pain occurs without activities involving IUE but not constant pain
5 if constant pain

24. Shoulder Shoulder pain precipitating factors 0 if no shoulder pain
1 if only having pain when reaching overhead
2 if pain free at rest pain occurs with specific range of motion able to continue all activities
3 if pain free at rest pain occurs with specific range of motion limiting activities
4 if pain at rest but not constant
5 constant pain -continued

Shoulder Algorithm

25. Shoulder Shoulder trauma 0 if no shoulder pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

26. Shoulder Shoulder contact quality 0 if no swelling nor erythema
1 if swollen or erythematous <15 minutes once a month
2 if swollen or erythematous >=15 minutes once a month but <15 minutes once a week
3 if swollen or erythematous >=15 minutes once a week but <½ of the day
4 if >=½ of the day swollen or erythematous, but not constant
5 constantly swollen or erythematous

27. Cervical Cervical daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

28. Cervical Cervical nighttime pain 0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

29. Cervical Cervical extent of pain referral 0 if no cervical pain
1 if cervical pain, never referred
2 pain refers away from neck but < one instance a week
3 pain refers away from neck >= once a week but not daily
4 if pain refers away from neck daily but can resolve with positional change
5 if pain refers away from neck daily and cannot resolve with positional change

30. Cervical Cervical quality of pain 0 if none
1 if dull & no analgesics needed
2 if dull & analgesics are used for relief
3 if sharp & no analgesics are used
4 if sharp & analgesics are used for relief
5 if uncontrolled with analgesics, either dull or sharp

31. Cervical Cervical pain relieving factors 0 if no cervical pain * Note: Examples of head support - resting head in hands, against reclining chair
1 if stopping activity relieves pain immediately without need for head support
2 if stopping activity with head support relieves pain immediately
3 if stopping activity resolves pain not immediately but within 3 minutes with or without head support
4 if stopping activity resolves pain after 3 minutes with or without head support
5 if constant pain unable to relieve by stopping activity or head support

32. Cervical Cervical pain precipitating factors 0 if no cervical pain * Note: Specific cervical range of motion = flexion, extension or rotation
1 if only worse with specific cervical range of motion easily reproduced
2 if worse when sitting or standing without head support but not immediately
3 if worse when sitting or standing without head support, occurs immediately
4 if constant pain, no associated symptoms (nausea, photophobia, headache, fever)
5 if constant pain plus another symptom (nausea, photophobia, headache, fever)

-continued

| Shoulder Algorithm |
|---|

33. Cervical Cervical trauma 0 if no cervical pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

34. Cervical Cervical paresthesia 0 if no cervical paresthesia
1 if localized to area of pain
2 if paresthetic ipsilateral cervical spine but not in area of pain
3 if paresthetic in one dermatome
4 if paresthetic to two ipsilateral dermatomes
5 if contralateral upper extremity or bilateral upper extremity paresthesia

35. Thoracic Thoracic daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

36. Thoracic Thoracic nighttime pain 0 if none * Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation

37. Thoracic Thoracic extent of pain referral 0 if no thoracic pain
1 if thoracic pain, never referred
2 pain refers away from back but < one instance a week
3 pain refers away from back >= once a week but not daily
4 if pain refers away from back daily but can resolve with positional change
5 if pain refers away from back daily and cannot resolve with positional change

38. Thoracic Thoracic quality of pain 0 if none
1 if dull & no analgesics needed
2 if dull & analgesics are used for relief
3 if sharp & no analgesics are used
4 if sharp & analgesics are used for relief
5 if uncontrolled with analgesics, either dull or sharp

39. Thoracic Thoracic pain relieving factors 0 if no thoracic pain
1 if stopping aggravating activity relieves pain immediately no positional change needed
2 if stopping activity and a positional change, other than laying down relieves pain immediately
3 if need to lie down to relieve pain and pain resolves within 3 minutes
4 if laying down takes >=3 minutes to relieve pain
5 unable to relieve pain with change in position

40. Thoracic Thoracic pain precipitating factors 0 if no thoracic pain
1 if worse only after clearly overusing back
2 if worse after activities which used to be tolerable
3 if worse after standing or walking but not immediately
4 if worse simply upon standing or walking, or worse after laying down
5 constant uncomfortable pain -continued Shoulder Algorithm

41. Thoracic Thoracic trauma 0 if no thoracic pain * Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain

42. Thoracic Thoracic paresthesia 0 if no thoracic paresthesia
1 if localized to area of pain
2 if paresthetic in only one dermatome
3 if paresthetic to two ipsilateral dermatomes
4 if paresthetic in three ipsilateral dermatomes
5 if contralateral dermatome or bilateral paresthesia

43. Elbow Elbow daytime pain 0 if none * Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics

44. Elbow Elbow nighttime pain 0 if no elbow pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics

45. Elbow Elbow quality of pain 0 if none
1 if dull & no analgesics needed
2 if dull & analgesics are used for relief
3 if sharp & no analgesics are used
4 if sharp & analgesics are used for relief
5 if sharp, uncontrolled with analgesics Applicants' shoulder algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care. e an expected result of pathology that is being treated according to the standard of care.

Referral Criteria

If the individual scored a 5 on any of the following Evaluation Factors, consider transfer to emergency medical care:

| 1 | 3 | 7 | 9 | 10 | 11 | 12 | 13 | 14 | 18 | 28 | 32 | 33 | 36 | 41 |

In certain embodiments of Applicants' method, if the individual scores a 5 on 4 or more of the following Evaluation Factors, refer to a physician immediately or emergency room.

| 15 | 20 | 21 | 22 | 23 | 24 | 25 | 27 | 29 | 30 | 31 | 34 | 35 | 37 | 38 | 39 | 42 | 44 |

If the individual scores a 3 on any of the following Evaluation Factors, refer to a physician with in 48 hours.

| 1 | 3 | 9 | 10 | 11 | 12 | 13 | 14 | 18 | 23 | 26 |

If the individual scored a 3 or higher on 3 or more of the following Evaluation Factors, refer to a physician with consult within 48 hours.

| 2 | 4 | 7 | 15 | 16 | 17 | 21 | 24 | 27 | 28 | 31 | 32 | 34 | 35 | 36 | 39 | 40 | 43 |

Thoracic Spine Algorithm

1. Constitutional Fever
   0 if none
   1 if felt warm but never took temp
   2 if recorded a Temp: above normal but <99.5
   3 if recorded a Temp: 99.5 but <101
   4 if recorded a Temp: 101 but <103
   5 if recorded a Temp: 103 or higher
2. Constitutional Weight loss
   0 if none
   1 if occurred but expected weight loss associated with current diet
   2 if not dieting but losing between 0 to 2% body weight per week
   3 if dieting but losing more weight than expected
   4 if losing >2% but <=4% body weight per week irrespective of diet
   5 if losing >4% body weight per week irrespective of diet
3. Constitutional Night Sweats
   0 if none
   1 if once in last 10 nights
   2 if >once in last 10 nights but <=every 3 nights
   3 if >once every 3 nights but <=once a night
   4 every night but no change in bedclothes needed
   5 if every night & changing bedclothes needed
4. Constitutional Fatigue
   0 if none
   1 occurs but well explained by lack of sleep or vigorous exercise
   2 spontaneously occurs but <=2 times a week
   3 if occurs 2 or more times a week but <daily
   4 if complains of fatigue daily, but not all day long
   5 if constant fatigue
5. Constitutional Medical Compliance Self Assessment
   0 if always taking meds and never missing follow up (F/U) appointments
   1 if takes meds & keeps F/U visits but does not feel they are necessary
   2 if compliant with 75% but <100% of meds or F/U visits
   3 if compliant with 25% but <75% of meds or F/U visits
   4 if compliant with <25% of meds or F/U visits but does not refuse either
   5 if refuses medications and medical F/U visits
6. Endocrine Diabetes Mellitus
   0 if not diabetic
   1 if not diabetic but a sibling or parent is
   2 controlled (fasting BS<150 mg/dl or last HA1C<7.5%) & on no medicines for glucose control
   3 controlled (fasting BS<150 mg/dl or last HA1C<7.5%) but on medication for glucose control
   4 if keeps F/U visits but fasting BS between 150 to 250 (mg/dl) often or last HA1C between 7.5 to 9.5(%)
   5 if fasting BS>250 mg/dl or not checking fingersticks or HA1C>9.5% or no DM F/U visits
7. Pulmonary Cough
   0 if none
   1 if cough <once every 3 days
   2 if cough >=once every 3 days but not daily & cough considered tolerable to client
   3 if cough >=once every 3 days but not daily, & cough considered not tolerable to client
   4 if daily cough but does not feel like it is non-stop
   5 if feels like non-stop coughing
8. Pulmonary Oxygen Usage
   0 if not using it and never been advised to use it
   1 if advised to use as outpatient, >2 years passed since told no longer needed
   2 if advised to use as outpatient but told OK to stop between >3 months ago to 2 years ago
   3 if advised to use as outpatient but told OK to stop between 3 months ago to present
   4 told to use constantly and compliant with usage
   5 if told to use constantly but non compliant with usage
9. Pulmonary Short of Breath
   0 if never
   1 if short of breath once in last 10 days
   2 if short of breath once >3 days ago but <10 days ago
   3 if short of breath once <=3 days ago or daily, but not more than once a day
   4 if short of breath more than once a day but <5 times a day
   5 if short of breath 5 times a day or more
10. Pulmonary Respiratory Chest Wall or Shoulder Pain
    0 if none
    1 if noted with cough or deep breath but 5 days or more between episodes
    2 if noted with cough or deep breath every 5 days or less, but not daily
    3 if noted with cough or deep breath, occurring daily, but tolerable to client 4 if noted with cough or deep breath, occurring daily, intolerable to client, not constant
5 if noting pain from cough or deep breath constantly throughout the day 11. Gastrointestinal Nausea
0 if none
1 if nauseated once every 5 days
2 if nauseated not daily but <every 5 days
3 if nauseated daily but <=3 times a day
4 if nauseated >3 times a day but not constantly nauseated
5 if constantly nauseated 12. Gastrointestinal Vomiting
0 if none
1 if vomiting once every 5 days
2 if vomiting not daily but <every 5 days
3 if vomiting daily but <=3 times a day
4 if vomiting >3 times a day but not constantly vomiting
5 if constantly vomiting 13. Gastrointestinal Heartburn
0 if none *Note: NSAIDs stands for Non Steroidal Anti Inflammatory Drugs (Ibuprofen, aspirin-like meds)
1 if having heartburn <15 minutes a week & not on NSAIDs & not on meds for heartburn
2 if heartburn occurs >=15 minutes/week but <daily & not on NSAIDs & not on meds for heartburn
3 if not on meds for heartburn plus it started after using NSAIDs or if not on NSAIDs, daily but not constant
4 if taking meds to treat heartburn which may be controlled or refractory but not constant heartburn
5 if constant heartburn with or without meds 14. Gastrointestinal Stool Color
0 if never had black nor bloody stools
1 if black or bloody stool once in last month
2 if black or bloody stools but occurring >once a month but <once a week
3 if black or bloody stools but occurring >=once a week but <every 2 days
4 if black or bloody stools but occurring every 2 days or more frequently but not 5 days in a row
5 if black or bloody stools for 5 days in a row or more 15. Gastrointestinal Swallowing Completeness
0 if food never gets stuck
1 if food gets stuck but not more than once a month
2 if food gets stuck >once a month but <=once week
3 if food gets stuck >once a week but not daily
4 if food gets stuck more than once a day but still able to eat
5 if food gets stuck so often that client is unable to eat 16. Gastrointestinal Stool Volume
0 if no change from baseline or actually decreased
1 if client feels >baseline but <50% increase
2 if client feels 50% to <100% more than baseline
3 if client feels 100% to <200% more than baseline
4 if client feels 200% or higher but fully continent
5 if so excessive afraid of continence or if had incontinence 17. Gastrointestinal Stool Consistency
0 if unchanged stools or well formed
1 if one loose stool but occurred over 7 days ago
2 if one loose stool >2 days ago but <7 days ago
3 if just one loose stool <=2 days ago
4 if daily loose stool but <=3 loose stools per day
5 if >3 loose stools per day 18. Gastrointestinal Control of Bowels
0 if complete control or longstanding continence problems proven benign by a workup
1 if new rectal leakage occurs but not more than once a month
2 if new rectal leakage occurs >once a month but <=once a week
3 if new rectal leakage occurs >once a week but not daily
4 if daily new rectal leakage but can wear same underwear throughout day
5 if daily new rectal leakage & change of underwear needed or protective padding Used 19. Gastrointestinal Constipation
0 if none or unchanged bowel habits
1 if felt constipated but not more than once a month
2 if felt constipated >once a month but <=once a week
3 if felt constipated >once a week but not daily
4 if feeling constipated daily but not taking meds for a bowel movement
5 if feeling constipated daily & needs meds for a bowel movement 20. Genitourinary Blood in Urine
0 if none
1 if noted but not more than once a month
2 if noted >once a month but <=once a week
3 if noted >once a week but not daily
4 if noted daily but not constantly
5 if noted with every void 21. Genitourinary Control of Urine
0 if complete control or longstanding continence problems proven benign by a workup
1 if new episodes of loss of control but not more than once a month
2 if new episodes of loss of control >once a month but <=once a week
3 if new episodes of loss of control >once a week but not daily
4 if daily new episodes of loss of control but can wear same underwear throughout day
5 if daily new episodes of loss of control & change of underwear needed or protective padding used 22. Genitourinary Urinary Frequency
0 if no change from baseline
1 if increased frequency occurred but not more than once a month
2 if increased frequency occurs >once a month but <=once a week
3 if increased frequency occurs >once a week but not daily
4 if increased frequency occurs daily but not constantly
5 if increased frequency occurs constantly throughout the day 23. Cardiovascular Palpitations
0 if none
1 if occurring but not more than once a month
2 if occurring but >once a month but <=once a week
3 if occurring >once a week but not daily
4 if occurring daily but not passing out
5 if ever passed out while having palpitations 24. Cardiovascular Angina
0 if none
1 if client told chest pain is not cardiac because of stress test or angiogram negative within last month
2 if followed in cardiology and no new nor worsening symptoms since last cardiology visit (stable angina)

3 if new or worsening chest pain intermittently at rest, none with activity
4 if new or worsening chest pain with activity relieved with rest
5 if currently experiencing new or worsening chest pain 25. Cardiovascular Relief of Presenting Symptom
    0 if symptom is distal to elbow or below waist *Note: Choices 1 to 5 assume symptom more proximal
    1 if symptom resolves in <1 minute without anything
    2 currently taking a long acting nitroglycerin product (Isordil Imdur or Nitropatch)
    3 if up to ½ of events spontaneously resolve & ½ of events require nitroglycerin or oxygen
    4 if more than ½ of the events require nitroglycerin or oxygen but symptoms are not constant
    5 if symptoms are constant unless nitroglycerin or oxygen is used or persist despite NTG or O2

26. Cardiovascular Exercise Impact on Presenting Symptom
    0 if symptom is distal to elbow or below waist *Note: Choices 1 to 5 assume symptom more proximal
    1 if symptom develops during rest after full exercise capacity
    2 if symptom occurs @ maximal exercise capacity
    3 if symptom occurs @ 50% or higher of maximal exercise capacity
    4 if symptom occurs @ less than 50% of maximal exercise capacity but not immediately
    5 if any exertional effort reproduces symptom nearly immediately 27. Neurologic Frequency of Upper Extremity Change in Sensation
    0 if none *Note: Score 0 if due to previously evaluated stroke or injury and unchanged since that event
    1 if sensation change <10 minutes over last month
    2 if sensation change >=10 minutes over last month but <15 minutes a week
    3 if sensation change >=15 minutes a week but not daily
    4 if sensation change daily but not constant
    5 if constant sensation change 28. Neurologic Frequency of Upper Extremity Weakness
    0 if none *Note: Score 0 if due to previously evaluated stroke or injury and unchanged since that event
    1 if weakness occurred <10 minutes over last month
    2 if weakness occurred >=10 minutes over last month but <15 minutes a week
    3 if weakness occurred >=15 minutes a week but not daily
    4 if weakness occurs daily but not constant
    5 if constant sensation of weakness 29. Neurologic Extent of Upper Extremity Weakness
    0 if none *Note: Score 0 if due to previously evaluated stroke or injury and unchanged since that event
    1 if seems weak but no loss of function
    2 if noticing weakness (dropping things) but maintaining ADLs
    3 if noticing weakness and impacting ADLs but can push self away
    4 if able to move upper extremity but cannot push self away
    5 if unable to move upper extremity 30. Neurologic Frequency of Lower Extremity Change in Sensation
    0 if none *Note: Score 0 if due to previously evaluated stroke or injury and unchanged since that event
    1 if sensation change <10 minutes over last month
    2 if sensation change >=10 minutes over last month but <15 minutes a week
    3 if sensation change >=15 minutes a week but not daily
    4 if sensation change daily but not constant
    5 if constant sensation change 31. Neurologic Frequency of Lower Extremity Weakness
    0 if none *Note: Score 0 if due to previously evaluated stroke or injury and unchanged since that event
    1 if weakness occurred <10 minutes over last month
    2 if weakness occurred >=10 minutes over last month but <15 minutes a week
    3 if weakness occurred >=15 minutes a week but not daily
    4 if weakness occurs daily but not constant
    5 if constant sensation of weakness 32. Neurologic Extent of Lower Extremity Weakness
    0 if none *Note: Score 0 if due to previously evaluated stroke or injury and unchanged since that event
    1 if seems weak but no loss of function
    2 if noticing weakness while walking (stopping or shorter distances) but can walk without falling
    3 if noticing weakness will fall while walking or relying on wheelchair or other assisted mobility
    4 if able to move legs but cannot walk nor go from seated to standing
    5 if unable to move lower extremity 33. Rheumatological Skin Morphology
    0 if none *Note: Morphology change implies telangiectasia, subcutaneous nodule, malar rash or discoid rash
    1 if only 1 instance of morphology change & known for >1 year
    2 if only 1 instance of morphology change but started within last year
    3 if up to 3 morphology changes that are known for >1 year or 2 new morphology changes within last year
    4 if 4 morphology changes, known for >1 year or 3 new morphology changes within last year
    5 if all 4 morphology changes that are new within last year 34. Hematological Immune Suppression
    0 if none *Note: Systemic steroids include Prednisone, Solumedrol, Kenalog, Depomedrol
    1 currently not immunosuppressed, but will take systemic steroids for <=1 week <=2 times a year
    2 currently not immunosuppressed but receives systemic steroids >2 times a year
    3 currently on systemic steroids or other immunosuppressants, but no transplant history & HIV negative
    4 HIV positive or transplant history
    5 known very low white blood cell count (WBC count <2) due to medical therapy or illness 35. Thoracic Thoracic Daytime Pain
    0 if none *Note: Responses 1-3 assume no analgesic medications are used
    1 if pain noted but none for >1 week
    2 if pain occurred <=1 week ago but lasts <½ of the day
    3 if pain occurred <=1 week ago but lasts >=½ of the day will resolve without analgesics
    4 if constant pain but resolves with analgesics
    5 constant pain, uncontrolled with analgesics 36. Thoracic Thoracic Nighttime Pain
    0 if none *Note: Responses 1-3 assume no analgesic medications are used
    1 able to sleep entire night once a comfortable position is found 2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation 37. Thoracic Thoracic Extent of Pain Referral
    0 if no thoracic pain
    1 if thoracic pain, never referred
    2 pain refers away from back but <one instance a week
    3 pain refers away from back >=once a week but not daily
    4 if pain refers away from back daily but can resolve with positional change
    5 if pain refers away from back daily and cannot resolve with positional change 38. Thoracic Thoracic Quality of Pain
    0 if none
    1 if dull & no analgesics needed
    2 if dull & analgesics are used for relief
    3 if sharp & no analgesics are used
    4 if sharp & analgesics are used for relief
    5 if uncontrolled with analgesics, either dull or sharp 39. Thoracic Thoracic Pain Relieving Factors
    0 if no thoracic pain
    1 if stopping aggravating activity relieves pain immediately no positional change needed
    2 if stopping activity and a positional change, other than laying down relieves pain immediately
    3 if need to lie down to relieve pain and pain resolves within 3 minutes
    4 if laying down takes >=3 minutes to relieve pain
    5 unable to relieve pain with change in position 40. Thoracic Thoracic Pain Precipitating Factors
    0 if no thoracic pain
    1 if worse only after clearly overusing back
    2 if worse after activities which used to be tolerable
    3 if worse after standing or walking but not immediately
    4 if worse simply upon standing or walking, or worse after laying down
    5 constant uncomfortable pain 41. Thoracic Thoracic Trauma
    0 if no thoracic pain *Note: Known incident means a recalled activity leading to the pain
    1 gradual onset of pain without known incident
    2 if after known incident and client felt medical care was not necessary and no medical evaluation performed
    3 if after known incident and client sought medical care >24 hours after known incident
    4 if after known incident and client sought medical care <=24 hours after known incident
    5 if no trauma or precipitating event but sudden onset severe pain 42. Thoracic Thoracic Paresthesia
    0 if no thoracic paresthesia
    1 if localized to area of pain
    2 if paresthetic in only one dermatome
    3 if paresthetic to two ipsilateral dermatomes
    4 if paresthetic in three ipsilateral dermatomes
    5 if contralateral dermatome or bilateral paresthesia 43. Lumbosacral Lumbosacral Daytime Pain
    0 if none *Note: Responses 1-3 assume no analgesic medications are used
    1 if pain noted but none for >1 week
    2 if pain occurred <=1 week ago but lasts <½ of the day
    3 if pain occurred <=1 week ago but lasts >=½ of the day will resolve without analgesics
    4 if constant pain but resolves with analgesics
    5 constant pain, uncontrolled with analgesics 44. Lumbosacral Lumbosacral Nighttime Pain
    0 if none *Note: Responses 1-3 assume no analgesic medications are used
    1 able to sleep entire night once a comfortable position is found
    2 pain awakens due to positional change, but able to fall back asleep
    3 awaken often without attributing to positional change, can fall back asleep
    4 if having pain but able to sleep with analgesic medications
    5 if problems sleeping due to pain and analgesics do not improve situation 45. Lumbosacral Lumbosacral Extent of Pain Referral
    0 if no lumbosacral pain
    1 if lumbosacral pain, never referred
    2 pain refers away from back but <one instance a week
    3 pain refers away from back >=once a week but not daily
    4 if pain refers away from back daily but can resolve with positional change
    5 if pain refers away from back daily and cannot resolve with positional change 46. Lumbosacral Lumbosacral Quality of Pain
    0 if none
    1 if dull & no analgesics needed
    2 if dull & analgesics are used for relief
    3 if sharp & no analgesics are used
    4 if sharp & analgesics are used for relief
    5 if uncontrolled with analgesics, either dull or sharp 47. Lumbosacral Lumbosacral Pain Relieving Factors
    0 if no lumbosacral pain
    1 if stopping aggravating activity relieves pain
    2 must sit to relieve the pain
    3 only laying down relieves pain
    4 must sit & forward flex to relieve pain
    5 unable to relieve pain with change in position 48. Lumbosacral Lumbosacral Pain Precipitating Factors
    0 if no lumbosacral pain
    1 if worse only after clearly overusing back
    2 if worse after activities which used to be tolerable
    3 if worse after standing or walking but not immediately
    4 if worse simply upon standing or walking, or worse after laying down
    5 constant uncomfortable pain 49. Lumbosacral Lumbosacral Trauma
    0 if no lumbosacral pain *Note: Known incident means a recalled activity leading to the pain
    1 gradual onset of pain without known incident
    2 if after known incident and client felt medical care was not necessary and no medical evaluation performed
    3 if after known incident and client sought medical care >24 hours after known incident 4 if after known incident and client sought medical care <=24 hours after known incident
5 if no trauma or precipitating event but sudden onset severe pain 50. Lumbosacral Lumbosacral Paresthesia
0 if no lumbosacral pareshthesia
1 if localized to area of pain
2 if paresthetic in only one dermatome
3 if paresthetic to two ipsilateral dermatomes
4 if paresthetic in three ipsilateral dermatomes
5 if contralateral lower extremity or bilateral lower extremity paresthesia 51. Cervical Cervical Daytime Pain
0 if none *Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics 52. Cervical Cervical Nighttime Pain
0 if none *Note: Responses 1-3 assume no analgesic medications are used
1 able to sleep entire night once a comfortable position is found
2 pain awakens due to positional change, but able to fall back asleep
3 awaken often without attributing to positional change, can fall back asleep
4 if having pain but able to sleep with analgesic medications
5 if problems sleeping due to pain and analgesics do not improve situation 53. Cervical Cervical Extent of Pain Referral
0 if no cervical pain
1 if cervical pain, never referred
2 pain refers away from neck but <one instance a week
3 pain refers away from neck >=once a week but not daily
4 if pain refers away from neck daily but can resolve with positional change
5 if pain refers away from neck daily and cannot resolve with positional change 54. Cervical Cervical Quality of Pain
0 if none
1 if dull & no analgesics needed
2 if dull & analgesics are used for relief
3 if sharp & no analgesics are used 4 if sharp & analgesics are used for relief
5 if uncontrolled with analgesics, either dull or sharp 55. Cervical Cervical Pain Relieving Factors
0 if no cervical pain *Note: Examples of head support—resting head in hands, against reclining chair
1 if stopping aggravating activity relieves pain immediately without need for head support
2 if stopping activity with head support relieves pain immediately
3 if stopping activity resolves pain not immediately but within 3 minutes with or without head support
4 if stopping activity resolves pain after 3 minutes with or without head support
5 if constant pain unable to relieve by stopping activity or head support 56. Cervical Cervical Pain Precipitating Factors
0 if no cervical pain *Note: Specific cervical range of motion=flexion, extension or rotation or combination of these
1 if only worse with specific cervical range of motion easily reproduced
2 if worse when sitting or standing without head support but not immediately
3 if worse when sitting or standing without head support, occurs immediately
4 if constant pain, no associated symptoms (nausea, photophobia, headache, fever)
5 if constant pain plus another symptom (nausea, photophobia, headache, fever)

57. Cervical Cervical Trauma
0 if no cervical pain *Note: Known incident means a recalled activity leading to the pain
1 gradual onset of pain without known incident
2 if after known incident and client felt medical care was not necessary and no medical evaluation performed
3 if after known incident and client sought medical care >24 hours after known incident
4 if after known incident and client sought medical care <=24 hours after known incident
5 if no trauma or precipitating event but sudden onset severe pain 58. Cervical Cervical Paresthesia
0 if no cervical paresthesia
1 if localized to area of pain
2 if paresthetic ipsilateral cervical spine but not in area of pain
3 if paresthetic in one dermatome
4 if paresthetic to two ipsilateral dermatomes
5 if contralateral upper extremity or bilateral upper extremity paresthesia 59. Shoulder Shoulder Daytime Pain
0 if none *Note: Responses 1-3 assume no analgesic medications are used
1 if pain noted but none for >1 week
2 if pain occurred <=1 week ago but lasts <½ of the day
3 if pain occurred <=1 week ago but lasts >=½ of the day will resolve without analgesics
4 if constant pain but resolves with analgesics
5 constant pain, uncontrolled with analgesics 60. Shoulder Shoulder Nighttime Pain
0 if no shoulder pain
1 able to sleep entire night once a comfortable position is found
2 pain awakens due to positional change, but able to fall back asleep
3 awaken often without attributing to positional change, can fall back asleep
4 constant if not for analgesics, able to sleep with medications
5 constant unrelenting, uncontrolled by analgesics 61. Shoulder Shoulder Quality of Pain
0 if none
1 if dull & no analgesics needed
2 if dull & analgesics are used for relief
3 if sharp & no analgesics are used
4 if sharp & analgesics are used for relief
5 if sharp, uncontrolled with analgesics Applicants' thoracic spine algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care. e an expected result of pathology that is being treated according to the standard of care.

Referral Criteria

In certain embodiments of Applicants' method, if the individual scored a 5 on any of the following factors, consider transfer to emergency medical care:

| 1 | 3 | 7 | 9 | 10 | 12 | 14 | 18 | 20 | 21 | 22 | 23 | 24 | 25 | 26 | 29 | 32 | 36 | 41 | 44 | 49 | 52 | 56 | 57 |
|---|---|---|---|----|----|----|----|----|----|----|----|----|----|----|----|----|----|----|----|----|----|----|----|

In certain embodiments of Applicants' method, if the individual scores a 5 on 3 or more of the following Evaluation Factors, refer to a physician immediately or emergency room.

| 13 | 15 | 16 | 35 | 37 | 38 | 39 | 42 | 43 | 45 | 46 | 47 | 48 | 50 | 51 | 53 | 54 | 55 | 58 | 59 | 60 | 61 | 62 |
|----|----|----|----|----|----|----|----|----|----|----|----|----|----|----|----|----|----|----|----|----|----|----|

In certain embodiments of Applicants' method, if the individual scored a 3 or higher on any of the following Evaluation Factors, refer to a physician with consult within 48 hours.

| 1 | 3 | 9 | 10 | 11 | 14 | 15 | 17 | 19 | 23 | 24 | 25 | 26 | 29 | 32 |
|---|---|---|----|----|----|----|----|----|----|----|----|----|----|----|

In certain embodiments of Applicants' method, if the individual scores a 3 or higher on 3 or more of the Evaluation Factors, refer to a physician with consult within 48 hours.

| 2 | 4 | 7 | 12 | 13 | 16 | 18 | 20 | 21 | 22 | 27 | 28 | 30 | 31 | 35 | 36 | 39 | 40 | 43 | 44 | 47 | 48 | 50 | 51 | 52 | 55 | 56 | 58 | 59 | 60 |
|---|---|---|----|----|----|----|----|----|----|----|----|----|----|----|----|----|----|----|----|----|----|----|----|----|----|----|----|----|----|

Poor Gait Algorithm

1. Constitutional Fever
   0 if none
   1 if felt warm but never took temp
   2 if recorded a Temp: above normal but <99.5
   3 if recorded a Temp: 99.5 but <101
   4 if recorded a Temp: 101 but <103
   5 if recorded a Temp: 103 or higher 2. Constitutional Weight Loss
   0 if none
   1 if occurred but expected weight loss associated with current diet
   2 if not dieting but losing between 0 to 2% body weight per week
   3 if dieting but losing more weight than expected
   4 if losing >2% but <=4% body weight per week irrespective of diet
   5 if losing >4% body weight per week irrespective of diet 3. Constitutional Night Sweats
   0 if none
   1 if once in last 10 nights
   2 if >once in last 10 nights but <=every 3 nights
   3 if >once every 3 nights but <=once a night
   4 if every night but no change in bedclothes needed
   5 if every night & changing bedclothes needed 4. Constitutional Sleep Pattern
   0 if no problems sleeping nor inappropriately falling asleep (eating, driving, during conversation)
   1 if feels sleepy only with lack of sleep, no naps, no inappropriately falling asleep
   2 if must have nap up to 3 times a week no inappropriately falling asleep
   3 if must have nap or will fall asleep inappropriately
   4 fall asleep inappropriately but <3 times a week
   5 inappropriately falling asleep >=3 times a week 5. Constitutional Fatigue
   0 if none
   1 occurs but well explained by lack of sleep or vigorous exercise
   2 spontaneously occurs but <=2 times a week
   3 if occurs 2 or more times a week but <daily
   4 if complains of fatigue daily, but not all day long
   5 if constant fatigue 6. Constitutional Medical Compliance Self Assessment
   0 if always taking meds and never missing follow up (F/U) appointments
   1 if takes meds & keeps F/U visits but does not feel they are necessary
   2 if compliant with 75% but <100% of meds or F/U visits
   3 if compliant with 25% but <75% of meds or F/U visits 4 if compliant with <25% of meds or F/U visits but does not refuse either
5 if refuses medications and medical F/U visits 7. Pulmonary Oxygen Usage
   0 if not using it and never been advised to use it
   1 if advised to use as outpatient, >2 years passed since told no longer needed
   2 if advised to use as outpatient but told OK to stop between >3 months ago to 2 years ago
   3 if advised to use as outpatient but told OK to stop between 3 months ago to present
   4 told to use constantly and compliant with usage
   5 if told to use constantly but non compliant with usage 8. Gastrointestinal Control of Bowels
   0 if complete control or longstanding continence problems proven benign by a workup
   1 if new rectal leakage occurs but not more than once a month
   2 if new rectal leakage occurs >once a month but <=once a week
   3 if new rectal leakage occurs >once a week but not daily
   4 if daily new rectal leakage but can wear same underwear throughout day
   5 if daily new rectal leakage & change of underwear needed or protective padding Used 9. Genitourinary Control of Urine
   0 if complete control or longstanding continence problems proven benign by a workup
   1 if new episodes of loss of control but not more than once a month
   2 if new episodes of loss of control >once a month but <=once a week
   3 if new episodes of loss of control >once a week but not daily
   4 if daily new episodes of loss of control but can wear same underwear throughout day
   5 if daily new episodes of loss of control & change of underwear needed or protective padding used 10. Cardiovascular Palpitations
    0 if none
    1 if occurring but not more than once a month
    2 if occurring but >once a month but <=once a week
    3 if occurring >once a week but not daily
    4 if occurring daily but not passing out
    5 if ever passed out while having palpitations 11. Cardiovascular Angina
    0 if none
    1 if client told chest pain is not cardiac because of stress test or angiogram negative within last month
    2 if followed in cardiology and no new nor worsening symptoms since last cardiology visit (stable angina)
    3 if new or worsening chest pain intermittently at rest, none with activity
    4 if new or worsening chest pain with activity relieved with rest
    5 if currently experiencing new or worsening chest pain 12. Cardiovascular Relief of Presenting Symptom
    0 if symptom is distal to elbow or below waist *Note: Choices 1 to 5 assume symptom more proximal
    1 if symptom resolves in <1 minute without anything
    2 currently taking a long acting nitroglycerin product (Isordil Imdur or Nitropatch)
    3 if up to ½ of events spontaneously resolve & ½ of events require nitroglycerin or oxygen
    4 if more than ½ of the events require nitroglycerin or oxygen but symptoms are not constant
    5 if symptoms are constant unless nitroglycerin or oxygen is used or persist despite NTG or O2

13. Cardiovascular Exercise Impact on Presenting Symptom
    0 if symptom is distal to elbow or below waist *Note: Choices 1 to 5 assume symptom more proximal
    1 if symptom develops during rest after full exercise capacity
    2 if symptom occurs @ maximal exercise capacity
    3 if symptom occurs @ 50% or higher of maximal exercise capacity
    4 if symptom occurs @ less than 50% of maximal exercise capacity but not immediately
    5 if any exertional effort reproduces symptom nearly immediately 14. Neurologic Visual Loss
    0 if none *Note: Choices 1-5 are either in 1 eye or both
    1 for <10 seconds and occurred over a month ago
    2 if had a reversible episode >10 seconds but occurred >10 days ago
    3 if had a reversible episode >10 seconds but occurred >3 days ago but <=10 days ago
    4 if had a reversible episode >10 seconds but occurred <=3 days ago
    5 if new onset visual loss that persists 15. Neurologic Visual Disturbance
    0 if none *Note: Choices 1-5 are either in 1 eye or both. Disturbance means spots or floaters not visual loss
    1 for <10 seconds and occurred over a month ago
    2 if had a reversible episode >10 seconds but occurred >10 days ago
    3 if had a reversible episode >10 seconds but occurred >3 days ago but <=10 days ago
    4 if had a reversible episode >10 seconds but occurred <=3 days ago
    5 if new onset visual disturbance that persists 16. Neurologic Diplopia
    0 if never *Note: Another way to describe diplopia is double vision
    1 for <10 seconds and occurred over a month ago
    2 if had a reversible episode >10 seconds but occurred >10 days ago
    3 if had a reversible episode >10 seconds but occurred >3 days ago but <=10 days ago
    4 if had a reversible episode >10 seconds but occurred <=3 days ago
    5 if new onset double vision that persists 17. Neurologic Photophobia
    0 if none *Note: Photophobia means exposure to light (such as indoors to outdoors) causes pain
    1 for <10 seconds and occurred over a month ago
    2 if had an episode >10 seconds but occurred >10 days ago
    3 if had an episode >10 seconds but occurred >3 days ago but <=10 days ago
    4 if had an episode >10 seconds but occurred <=3 days ago
    5 if new onset photophobia that persists 18. Neurologic Hearing Loss
    0 if none
    1 for <10 seconds and occurred over a month ago
    2 if had an episode >10 seconds but occurred >10 days ago
    3 if had an episode >10 seconds but occurred >3 days ago but <=10 days ago 4 if had an episode >10 seconds but occurred <=3 days ago
5 if new onset hearing loss that persists 19. Neurologic Swallow Coordination
    0 if none
    1 if had 1 difficulty swallowing episode and occurred over a month ago
    2 if had 1 difficulty swallowing episode but occurred >10 days ago and <=1 month ago
    3 if had 1 difficulty swallowing episode but occurred >3 days ago but <=10 days ago
    4 if had 1 difficulty swallowing episode but occurred <=3 days ago but not constant
    5 if constantly having difficulty swallowing episodes 20. Neurologic Vertigo
    0 if none
    1 for <10 seconds and occurred over a month ago
    2 if had an episode >10 seconds but occurred >10 days ago
    3 if had an episode >10 seconds but occurred >3 days ago but <=10 days ago
    4 if had an episode >10 seconds but occurred <=3 days ago
    5 if new onset vertigo that persists 21. Neurologic Headache
    0 if no new or worsening headache
    1 if new or worsening headache <20 minutes and occurred over 2 weeks ago
    2 if new or worsening headache lasting <20 minutes and occurred within 2 weeks
    3 if new or worsening headache >=20 minutes but occurred >1 week ago
    4 if new or worsening headache >=20 minutes but occurred within last week, currently headache free
    5 if currently experiencing new or worsening headaches lasting >=20 minutes 22. Neurologic Frequency of Upper Extremity Change in Sensation
    0 if none *Note: Score 0 if due to previously evaluated stroke or injury and unchanged since that event
    1 if sensation change <10 minutes over last month
    2 if sensation change >=10 minutes over last month but <15 minutes a week
    3 if sensation change >=15 minutes a week but not daily
    4 if sensation change daily but not constant
    5 if constant sensation change 23. Neurologic Frequency of Upper Extremity Weakness
    0 if none *Note: Score 0 if due to previously evaluated stroke or injury and unchanged since that event
    1 if weakness occurred <10 minutes over last month
    2 if weakness occurred >=10 minutes over last month but <15 minutes a week
    3 if weakness occurred >=15 minutes a week but not daily
    4 if weakness occurs daily but not constant
    5 if constant sensation of weakness 24. Neurologic Extent of Upper Extremity Weakness
    0 if none *Note: Score 0 if due to previously evaluated stroke or injury and unchanged since that event
    1 if seems weak but no loss of function
    2 if noticing weakness (dropping things) but maintaining ADLs
    3 if noticing weakness and impacting ADLs but can push self away
    4 if able to move upper extremity but cannot push self away
    5 if unable to move upper extremity 25. Neurologic Frequency of Lower Extremity Change in Sensation
    0 if none *Note: Score 0 if due to previously evaluated stroke or injury and unchanged since that event
    1 if sensation change <10 minutes over last month
    2 if sensation change >=10 minutes over last month but <15 minutes a week
    3 if sensation change >=15 minutes a week but not daily
    4 if sensation change daily but not constant
    5 if constant sensation change 26. Neurologic Frequency of Lower Extremity Weakness
    0 if none *Note: Score 0 if due to previously evaluated stroke or injury and unchanged since that event
    1 if weakness occurred <10 minutes over last month
    2 if weakness occurred >=10 minutes over last month but <15 minutes a week
    3 if weakness occurred >=15 minutes a week but not daily
    4 if weakness occurs daily but not constant
    5 if constant sensation of weakness 27. Neurologic Extent of Lower Extremity Weakness
    0 if none *Note: Score 0 if due to previously evaluated stroke or injury and unchanged since that event
    1 if seems weak but no loss of function
    2 if noticing weakness while walking (stopping or shorter distances) but can walk without falling
    3 if noticing weakness will fall while walking or relying on wheelchair or other assisted mobility
    4 if able to move legs but cannot walk nor go from seated to standing
    5 if unable to move lower extremity 28. Lumbosacral Lumbosacral Quality of Pain
    0 if none
    1 if dull & no analgesics needed
    2 if dull & analgesics are used for relief
    3 if sharp & no analgesics are used
    4 if sharp & analgesics are used for relief
    5 if uncontrolled with analgesics, either dull or sharp 29. Lumbosacral Lumbosacral Pain Relieving Factors
    0 if no lumbosacral pain
    1 if stopping aggravating activity relieves pain
    2 must sit to relieve the pain
    3 only laying down relieves pain
    4 must sit & forward flex to relieve pain
    5 unable to relieve pain with change in position 30. Lumbosacral Lumbosacral Pain Precipitating Factors
    0 if no lumbosacral pain
    1 if worse only after clearly overusing back
    2 if worse after activities which used to be tolerable
    3 if worse after standing or walking but not immediately
    4 if worse simply upon standing or walking, or worse after laying down
    5 constant uncomfortable pain 31. Lumbosacral Lumbosacral Trauma
    0 if no lumbosacral pain *Note: Known incident means a recalled activity leading to the pain
    1 gradual onset of pain without known incident
    2 if after known incident and client felt medical care was not necessary and no medical evaluation performed
    3 if after known incident and client sought medical care >24 hours after known incident
    4 if after known incident and client sought medical care <=24 hours after known incident
    5 if no trauma or precipitating event but sudden onset severe pain 32. Lumbosacral Lumbosacral Paresthesia
    0 if no lumbosacral pareshthesia
    1 if localized to area of pain
    2 if paresthetic in only one dermatome
    3 if paresthetic to two ipsilateral dermatomes
    4 if paresthetic in three ipsilateral dermatomes
    5 if contralateral lower extremity or bilateral lower extremity paresthesia 33. Thoracic Thoracic Quality of Pain
    0 if none
    1 if dull & no analgesics needed
    2 if dull & analgesics are used for relief
    3 if sharp & no analgesics are used
    4 if sharp & analgesics are used for relief
    5 if uncontrolled with analgesics, either dull or sharp 34. Thoracic Thoracic Pain Relieving Factors
    0 if no thoracic pain
    1 if stopping aggravating activity relieves pain immediately no positional change needed
    2 if stopping activity and a positional change, other than laying down relieves pain immediately
    3 if need to lie down to relieve pain and pain resolves within 3 minutes
    4 if laying down takes >=3 minutes to relieve pain
    5 unable to relieve pain with change in position 35. Thoracic Thoracic Pain Precipitating Factors
    0 if no thoracic pain
    1 if worse only after clearly overusing back
    2 if worse after activities which used to be tolerable
    3 if worse after standing or walking but not immediately
    4 if worse simply upon standing or walking, or worse after laying down
    5 constant uncomfortable pain 36. Thoracic Thoracic Trauma
    0 if no thoracic pain *Note: Known incident means a recalled activity leading to the pain
    1 gradual onset of pain without known incident
    2 if after known incident and client felt medical care was not necessary and no medical evaluation performed
    3 if after known incident and client sought medical care >24 hours after known incident
    4 if after known incident and client sought medical care <=24 hours after known incident
    5 if no trauma or precipitating event but sudden onset severe pain 37. Thoracic Thoracic Paresthesia
    0 if no thoracic paresthesia
    1 if localized to area of pain
    2 if paresthetic in only one dermatome
    3 if paresthetic to two ipsilateral dermatomes
    4 if paresthetic in three ipsilateral dermatomes
    5 if contralateral dermatome or bilateral paresthesia 38. Cervical Cervical Quality of Pain
    0 if none
    1 if dull & no analgesics needed
    2 if dull & analgesics are used for relief
    3 if sharp & no analgesics are used
    4 if sharp & analgesics are used for relief
    5 if uncontrolled with analgesics, either dull or sharp 39. Cervical Cervical Pain Relieving Factors
    0 if no cervical pain *Note: Examples of head support—resting head in hands, against reclining chair
    1 if stopping aggravating activity relieves pain immediately without need for head support
    2 if stopping activity with head support relieves pain immediately
    3 if stopping activity resolves pain not immediately but within 3 minutes with or without head support
    4 if stopping activity resolves pain after 3 minutes with or without head support
    5 if constant pain unable to relieve by stopping activity or head support 40. Cervical Cervical Pain Precipitating Factors
    0 if no cervical pain *Note: Specific cervical range of motion=flexion, extension or rotation
    1 if only worse with specific cervical range of motion easily reproduced
    2 if worse when sitting or standing without head support but not immediately
    3 if worse when sitting or standing without head support, occurs immediately
    4 if constant pain, no associated symptoms (nausea, photophobia, headache, fever)
    5 if constant pain plus another symptom (nausea, photophobia, headache, fever)

41. Cervical Cervical Trauma
    0 if no cervical pain *Note: Known incident means a recalled activity leading to the pain
    1 gradual onset of pain without known incident
    2 if after known incident and client felt medical care was not necessary and no medical evaluation performed
    3 if after known incident and client sought medical care >24 hours after known incident
    4 if after known incident and client sought medical care <=24 hours after known incident
    5 if no trauma or precipitating event but sudden onset severe pain 42. Cervical Cervical Paresthesia
    0 if no cervical paresthesia
    1 if localized to area of pain
    2 if paresthetic ipsilateral cervical spine but not in area of pain
    3 if paresthetic in one dermatome
    4 if paresthetic to two ipsilateral dermatomes
    5 if contralateral upper extremity or bilateral upper extremity paresthesia 43. Hip Hip Daytime Pain
    0 if none *Note: Responses 1-3 assume no analgesic medications are used
    1 if pain noted but none for >1 week
    2 if pain occurred <=1 week ago but lasts <½ of the day
    3 if pain occurred <=1 week ago but lasts >=½ of the day will resolve without analgesics
    4 if constant pain but resolves with analgesics
    5 constant pain, uncontrolled with analgesics 44. Hip Hip Nighttime Pain
    0 if no hip pain
    1 able to sleep entire night once a comfortable position is found
    2 pain awakens due to positional change, but able to fall back asleep
    3 awaken often without attributing to positional change, can fall back asleep
    4 constant if not for analgesics, able to sleep with medications
    5 constant unrelenting, uncontrolled by analgesics 45. Hip Hip Quality of Pain
   - 0 if none
   - 1 if dull & no analgesics needed
   - 2 if dull & analgesics are used for relief
   - 3 if sharp & no analgesics are used
   - 4 if sharp & analgesics are used for relief
   - 5 if sharp, uncontrolled with analgesics 46. Hip Hip Trauma
   - 0 if no hip pain *Note: Known incident means a recalled activity leading to the pain
   - 1 gradual onset of pain without known incident
   - 2 if after known incident and client felt medical care was not necessary and no medical evaluation performed
   - 3 if after known incident and client sought medical care >24 hours after known incident
   - 4 if after known incident and client sought medical care <=24 hours after known incident
   - 5 if no trauma or precipitating event but sudden onset severe pain 47. Hip Hip Contact Quality
   - 0 if no swelling nor erythema
   - 1 if swollen or erythematous <15 minutes once a month
   - 2 if swollen or erythematous >=15 minutes once a month but <15 minutes once a week
   - 3 if swollen or erythematous >=15 minutes once a week but <½ of the day
   - 4 if >=½ of the day swollen or erythematous, but not constant
   - 5 constantly swollen or erythematous 48. Knee Knee Quality of Pain
   - 0 if none
   - 1 if dull & no analgesics needed
   - 2 if dull & analgesics are used for relief
   - 3 if sharp & no analgesics are used
   - 4 if sharp & analgesics are used for relief
   - 5 if sharp, uncontrolled with analgesics 49. Knee Knee Trauma
   - 0 if no knee pain *Note: Known incident means a recalled activity leading to the pain
   - 1 gradual onset of pain without known incident
   - 2 if after known incident and client felt medical care was not necessary and no medical evaluation performed
   - 3 if after known incident and client sought medical care >24 hours after known incident
   - 4 if after known incident and client sought medical care <=24 hours after known incident
   - 5 if no trauma or precipitating event but sudden onset severe pain 50. Knee Knee Contact Quality
   - 0 if no swelling nor erythema
   - 1 if swollen or erythematous <15 minutes once a month
   - 2 if swollen or erythematous >=15 minutes once a month but <15 minutes once a week
   - 3 if swollen or erythematous >=15 minutes once a week but <½ of the day
   - 4 if >=½ of the day swollen or erythematous, but not constant
   - 5 constantly swollen or erythematous 51. Ankle and Foot Ankle and Foot Quality of Pain
   - 0 if none
   - 1 if dull & no analgesics needed
   - 2 if dull & analgesics are used for relief
   - 3 if sharp & no analgesics are used
   - 4 if sharp & analgesics are used for relief
   - 5 if sharp, uncontrolled with analgesics 52. Ankle and Foot Ankle and Foot Vascular Changes
   - 0 if none
   - 1 if cold occasionally no pain no ulcers & functional
   - 2 if ischemic pain, no ulcers & functional
   - 3 if one ulcer
   - 4 several ulcers or threatened digits
   - 5 previous auto-amputation or black necrotic digits 53. Ankle and Foot Ankle and Foot Contact Quality
   - 0 if no swelling nor erythema
   - 1 if swollen or erythematous <15 minutes once a month
   - 2 if swollen or erythematous >=15 minutes once a month but <15 minutes once a week
   - 3 if swollen or erythematous >=15 minutes once a week but <½ of the day
   - 4 if >=½ of the day swollen or erythematous, but not constant
   - 5 constantly swollen or erythematous 54. Ankle and Foot Ankle and Foot Trauma
   - 0 if no ankle or foot pain *Note: Known incident means a recalled activity leading to the pain
   - 1 gradual onset of pain without known incident
   - 2 if after known incident and client felt medical care was not necessary and no medical evaluation performed
   - 3 if after known incident and client sought medical care >24 hours after known incident
   - 4 if after known incident and client sought medical care <=24 hours after known incident
   - 5 if no trauma or precipitating event but sudden onset severe pain 55. Rheumatological Joint Swelling
   - 0 if not having joint swelling
   - 1 if only one joint swells not greater than once a week
   - 2 if multiple joints swell not greater than once a week
   - 3 if one or more joints swell >once a week but not daily
   - 4 if one or more joints swell daily but not constantly
   - 5 if constant daily swelling of one or more joints 56. Rheumatological Joint Stiffness
   - 0 if not having joint stiffness
   - 1 if only one joint is stiff but not greater than once a week
   - 2 if multiple joints become stiff not greater than once a week
   - 3 if one or more joints become stiff >once a week but not daily
   - 4 if one or more joints become stiff daily but not constantly
   - 5 if constant daily stiffness of one or more joints Applicants' poor gait algorithm further comprises the following Referral Criteria, i.e. scoring guide. As those skilled in the art will appreciate, therapists need to use clinical experience and professional judgment when deciding the need for referral. The ability and timeframe to contact and discuss clients with physicians may also impact the therapist's referral pattern. In some medical communities, physicians are available to discuss possible pathology or concerns within 30 minutes. In other areas, physicians may be difficult to contact and communicate with in a short time frame. Attempts should always be made to contact a referring physician to discuss the care of shared clients. Pathology may have already been screened for and ruled out or in by the attending physician. Depending on the clients past medical history, some symptoms may be an expected result of pathology that is being treated in according with an applicable standard of care.

Referral Criteria

In certain embodiments of Applicants' method, if the individual scored a 5 on any of the following factors, consider transfer to emergency medical care:

| | | | | | | | | | | | | | | | | | | | | | |
|---|---|---|---|---|---|---|---|---|---|---|---|---|---|---|---|---|---|---|---|---|---|
| 1 | 3 | 8 | 9 | 10 | 11 | 12 | 13 | 14 | 16 | 17 | 20 | 21 | 24 | 27 | 31 | 36 | 40 | 41 | 43 | 44 | 46 | 52 |

In certain embodiments of Applicants' method, if the individual scores a 5 on 3 or more of the following Evaluation Factors, refer to a physician immediately or emergency room.

| | | | | | | | | | | | | | | | | |
|---|---|---|---|---|---|---|---|---|---|---|---|---|---|---|---|---|
| 19 | 28 | 29 | 30 | 32 | 33 | 34 | 37 | 38 | 39 | 42 | 45 | 47 | 48 | 49 | 50 | 53 |

In certain embodiments of Applicants' method, if the individual scored a 3 or higher on any of the following Evaluation Factors, refer to a physician with consult within 48 hours.

| | | | | | | | | | | | | | | | | | | |
|---|---|---|---|---|---|---|---|---|---|---|---|---|---|---|---|---|---|---|
| 1 | 3 | 4 | 10 | 11 | 12 | 13 | 14 | 15 | 16 | 17 | 19 | 24 | 27 | 43 | 51 | 52 | 53 | 54 | 55 | 56 |

In certain embodiments of Applicants' method, if the individual scores a 3 or higher on 3 or more of the Evaluation Factors, refer to a Physician Consult within 48 hours.

| | | | | | | | | | | | | | | | | | | | | | | |
|---|---|---|---|---|---|---|---|---|---|---|---|---|---|---|---|---|---|---|---|---|---|---|
| 2 | 5 | 8 | 9 | 18 | 20 | 21 | 22 | 23 | 25 | 26 | 29 | 30 | 32 | 34 | 35 | 39 | 40 | 42 | 44 | 45 | 47 | 50 | 57 | 58 |

While the preferred embodiments of the present invention have been illustrated in detail, it should be apparent that modifications and adaptations to those embodiments may occur to one skilled in the art without departing from the scope of the present invention as set forth in the following claims.

We claim:

1. A method to evaluate a client by a physical therapist, comprising the steps of:
    providing a plurality of evaluation factors, wherein each evaluation factor comprises point ratings from 0 to 5, wherein a higher point rating indicates a higher likelihood that a client should be referred to emergency care;
    providing a plurality of evaluation algorithms, wherein each of said evaluation algorithms comprises two or more of said evaluation factors;
    determining if a client is experiencing distress;
    operative if a client is experiencing distress, selecting an evaluation algorithm responsive to said distress, wherein said selected evaluation algorithm comprises (N) evaluation factors, wherein (N) is greater than 1;
    determining if any of said (N) evaluation factors is designated an Emergency Referral evaluation factor;
    operative if any of said (N) evaluation factors is designated an Emergency Referral evaluation factor, determining if the client's reported distress corresponds to a point rating of "5" for any of the Emergency Referral evaluation factors;
    operative if the client's reported pain corresponds to a point rating of "5" for any of the Emergency Referral evaluation factors, referring the patent for immediate emergency care.

2. The method of claim 1, further comprising the steps of:
    operative if none of said (N) evaluation factors is designated an Emergency Referral evaluation factor:
    setting (i) to 1, wherein (i) is greater than or equal to 1 and less than or equal to (N);
    selecting the (i)th evaluation factor;
    assigning the (i)th point rating using evaluation criteria recited in the (i)th evaluation factor;
    determining if (i) equals (N);
    operative if (i) is less than (N), incrementing (i) by unity and repeating said selecting step, said assigning step, said determining step, and said incrementing step;
    operative if (i) equals (N), determining whether to refer said client to emergency care based upon the (N) point ratings.

3. The method of claim 2, further comprising the step of determining whether to refer said client to a physician consult based upon the (N) point ratings.

4. The method of claim 1, further comprising the steps of:
    operative if the client's reported pain does not correspond to a point rating of "5" for any of the Emergency Referral factors comprising said selected evaluation algorithm:

setting (i) to 1, wherein (i) is greater than or equal to 1 and less than or equal to (N);

selecting the (i)th evaluation factor;

assigning the (i)th point rating using evaluation criteria recited in the (i)th evaluation factor;

determining if (i) equals (N);

operative if (i) is less than (N), incrementing (i) by unity and repeating said selecting step, said assigning step, said determining step, and said incrementing step;

operative if (i) equals (N), determining whether to refer said client to emergency care based upon the (N) point ratings.

5. The method of claim 4, further comprising the step of determining whether to refer said client to a physician consult based upon the (N) point ratings.

6. The method of claim 1, wherein said providing a plurality of evaluation algorithms step comprises providing an Emergency Medical Algorithm, an Ankle and Foot Algorithm, a Cervical Spine Algorithm, an Elbow Algorithm, a Hand And Wrist Algorithm, a Headache Algorithm, a Hip Algorithm, a Knee Algorithm, a Lumbar Spine Algorithm, a Pelvic And Sacrum Algorithm, a Shoulder Algorithm, a Thoracic Spine Algorithm, a Poor Gait, and a Vertigo Algorithm.

7. The method of claim 6, wherein said providing a plurality of evaluation factors step comprises providing a Fever evaluation factor, Weight loss evaluation factor, Night sweats evaluation factor, Day sweats evaluation factor, Sleep pattern evaluation factor, Fatigue evaluation factor, Medical compliance self assessment evaluation factor, Diabetes mellitus evaluation factor, Cough evaluation factor, Oxygen usage evaluation factor, Short of breath evaluation factor, Respiratory chest wall or shoulder pain evaluation factor, Nausea evaluation factor, Vomiting evaluation factor, Heartburn evaluation factor, Stool color evaluation factor, Swallowing completeness evaluation factor, Stool volume evaluation factor, Stool consistency evaluation factor, Control of, bowels evaluation factor, Constipation evaluation factor, Blood in urine evaluation factor, Control of urine evaluation factor, Urinary frequency evaluation factor, Palpitations evaluation factor, Angina evaluation factor, Relief of presenting symptom evaluation factor, Exercise impact on presenting symptom evaluation factor, Visual loss evaluation factor, Visual disturbance evaluation factor, Diplopia evaluation factor, Photophobia evaluation factor, Hearing loss evaluation factor, Swallow coordination evaluation factor, Vertigo evaluation factor, Headache evaluation factor, Frequency of upper extremity change in sensation evaluation factor, Frequency of upper extremity weakness evaluation factor, Extent of upper extremity weakness evaluation factor, Frequency of lower extremity change in sensation evaluation factor, Frequency of lower extremity weakness evaluation factor, Extent of lower extremity weakness evaluation factor, Lumbosacral daytime pain, valuation factor, Lumbosacral nighttime pain evaluation factor, Lumbosacral extent of pain referral evaluation factor, Lumbosacral quality of pain evaluation factor, Lumbosacral pain relieving factors evaluation factor, Lumbosacral pain precipitating factors evaluation factor, Lumbosacral trauma evaluation factor, Lumbosacral, aresthesia evaluation factor, Thoracic daytime pain evaluation factor, Thoracic nighttime pain evaluation factor, Thoracic extent of pain referral evaluation factor, Thoracic quality of pain evaluation factor, Thoracic pain relieving factors evaluation factor, Thoracic pain precipitating factors evaluation factor, Thoracic trauma, valuation factor, Thoracic paresthesia evaluation factor, Cervical daytime pain evaluation factor, Cervical nighttime pain evaluation factor, Cervical extent of pain referral evaluation factor, Cervical quality of pain evaluation factor, Cervical pain relieving factors evaluation factor, Cervical pain precipitating factors evaluation, actor, Cervical trauma evaluation factor, Cervical paresthesia evaluation factor, Shoulder daytime pain evaluation factor, Shoulder nighttime pain evaluation factor, Shoulder quality of pain evaluation factor, Shoulder pain relieving factors evaluation factor, Shoulder pain precipitating factors evaluation factor, Shoulder trauma evaluation factor, Shoulder contact quality evaluation factor, Elbow daytime pain evaluation factor, Elbow nighttime pain evaluation factor, Elbow quality of pain evaluation factor, Elbow trauma evaluation factor, Elbow contact quality evaluation factor, Hip daytime pain evaluation factor, Hip nighttime pain evaluation factor, Hip quality of pain evaluation factor, Hip trauma evaluation factor, Hip contact quality evaluation factor, Knee daytime pain evaluation factor, Knee nighttime pain evaluation factor, Knee quality of pain evaluation factor, Knee trauma evaluation factor, Knee contact quality evaluation factor, Wrist and hand daytime pain, valuation factor, Wrist and hand nighttime pain evaluation factor, Wrist and hand quality of pain evaluation factor, Wrist and hand contact quality evaluation factor, Wrist and hand vascular changes evaluation factor, Wrist and hand trauma evaluation factor, Wrist and hand non bony deformities evaluation factor, Wrist and hand bony deformities evaluation factor, Ankle and foot daytime pain evaluation factor, Ankle and foot nighttime pain evaluation factor, Ankle and foot quality of pain evaluation factor, Ankle and foot vascular changes evaluation factor, Ankle and foot contact quality evaluation factor, Ankle and foot trauma evaluation factor, Joint welling evaluation factor, Joint stiffness evaluation factor, Systemic Lupus Erythematosis evaluation factor, Rheumatoid Arthritis evaluation factor, Skin morphology evaluation factor, Sunlight effect on skin evaluation factor, Anemia evaluation factor, Immune suppression evaluation factor, Bleeding tendency evaluation factor.

8. The method of claim 7, wherein the following evaluation factors comprise Emergency Referral evaluation factors:

Fever, Night sweats, Cough, Short of breath, Respiratory chest wall or shoulder pain, Vomiting, Stool color, Control of bowels, Blood in urine, Control of urine, Urinary frequency, Palpitations, Angina, Relief of presenting symptom, Exercise impact on presenting symptom, Visual loss, Diplopia, Photophobia, Vertigo, Headache, Extent of upper extremity weakness, Extent of lower extremity weakness, Lumbosacral nighttime pain, Lumbosacral trauma, Thoracic nighttime pain, Thoracic trauma, Cervical nighttime pain, Cervical pain precipitating factors, Cervical trauma, Hip daytime pain, Hip nighttime pain, Hip trauma, Wrist and hand vascular changes, Ankle and foot vascular changes, Bleeding tendency.

9. An article of manufacture comprising a processor and a computer readable medium, a plurality of evaluation factors encoded in said computer readable medium, wherein each evaluation factor comprises point ratings from 0 to 5, wherein a higher point rating indicates a higher likelihood that a client should be referred to emergency care, a plurality of evaluation algorithms encoded in said computer readable medium, wherein each of said evaluation algorithms comprises two or more of said evaluation factors, and computer readable program code to evaluate a client presenting to a physical therapist encoded in said computer readable medium, the computer readable program code comprising a series of computer readable program steps to effect:

determining if a client is experiencing pain;

operative if a client is experiencing pain, selecting an evaluation algorithm responsive to said pain, wherein said selected evaluation algorithm comprises (N) evaluation factors, wherein (N) is greater than 1;

determining if any of said (N) evaluation factors is designated an Emergency Referral evaluation factor;

operative if any of said (N) evaluation factors is designated an Emergency Referral evaluation factor, determining if the client's reported pain corresponds to a point rating of "5" for any of the Emergency Referral evaluation factors;

operative if the client's reported pain corresponds to a point rating of "5" for any of the Emergency Referral evaluation factors, generating a message recommending that the physical therapist refer the client for immediate emergency care.

10. The article of manufacture of claim 9, said computer readable program code further comprising a series of computer readable program steps to effect:

operative if none of said (N) evaluation factors is designated an Emergency Referral evaluation factor:

setting (i) to 1, wherein (i) is greater than or equal to 1 and less than or equal to (N);

selecting the (i)th evaluation factor;

assigning the (i)th point rating using evaluation criteria recited in the (i)th evaluation factor;

determining if (i) equals (N);

operative if (i) is less than (N), incrementing (i) by unity and repeating said selecting step, said assigning step, said determining step, and said incrementing step;

operative if (i) equals (N), determining whether to generate a message recommending the physical therapist refer said client to emergency care based upon the (N) point ratings.

11. The article of manufacture of claim 10, said computer readable program code further comprising a series of computer readable program steps to effect determining whether to generate a message recommending the physical therapist refer said client to a physician consult based upon the (N) point ratings.

12. The article of manufacture of claim 9, said computer readable program code further comprising a series of computer readable program steps to effect:

operative if the client's reported pain does not correspond to a point rating of "5" for any of the Emergency Referral factors comprising said selected evaluation algorithm:

setting (i) to 1, wherein (i) is greater than or equal to 1 and less than or equal to (N);

selecting the (i)th evaluation factor;

assigning the (i)th point rating using evaluation criteria recited in the (i)th evaluation factor;

determining if (i) equals (N);

operative if (i) is less than (N), incrementing (i) by unity and repeating said selecting step, said assigning step, said determining step, and said incrementing step;

operative if (i) equals (N), determining whether to generate a message recommending the physical therapist refer said client to emergency care based upon the (N) point ratings.

13. The article of manufacture of claim 12, said computer readable program code further comprising a series of computer readable program steps to effect determining whether to generate a message recommending the physical therapist refer said client to a physician consult based upon the (N) point ratings.

14. The article of manufacture of claim 9, wherein said plurality of evaluation algorithms comprise an Emergency Medical Algorithm, an Ankle and Foot Algorithm, a Cervical Spine Algorithm, an Elbow Algorithm, a Hand And Wrist Algorithm, a Headache Algorithm, a Hip Algorithm, a Knee Algorithm, a Lumbar Spine Algorithm, a Pelvic And Sacrum Algorithm, a Shoulder Algorithm, a Thoracic Spine Algorithm, a Poor Gait, and a Vertigo Algorithm.

15. The article of manufacture of claim 14, wherein said plurality of evaluation factors comprise a Fever evaluation factor, Weight loss evaluation factor, Night sweats evaluation factor, Day sweats evaluation factor, Sleep pattern evaluation factor, Fatigue evaluation factor, Medical compliance self assessment evaluation factor, Diabetes mellitus evaluation factor, Cough evaluation factor, Oxygen usage evaluation factor, Short of breath evaluation factor, Respiratory chest wall or shoulder pain evaluation factor, Nausea evaluation factor, Vomiting evaluation factor, Heartburn evaluation factor, Stool color evaluation factor, Swallowing completeness evaluation factor, Stool volume evaluation factor, Stool consistency evaluation factor, Control of, bowels evaluation factor, Constipation evaluation factor, Blood in urine evaluation factor, Control of urine evaluation factor, Urinary frequency evaluation factor, Palpitations evaluation factor, Angina evaluation factor, Relief of presenting symptom evaluation factor, Exercise impact on presenting symptom evaluation factor, Visual loss evaluation factor, Visual disturbance evaluation factor, Diplopia evaluation factor, Photophobia evaluation factor, Hearing loss evaluation factor, Swallow coordination evaluation factor, Vertigo evaluation factor, Headache evaluation factor, Frequency of upper extremity change in sensation evaluation factor, Frequency of upper extremity weakness evaluation factor, Extent of upper extremity weakness evaluation factor, Frequency of lower extremity change in sensation evaluation factor, Frequency of lower extremity weakness evaluation factor, Extent of lower extremity weakness evaluation factor, Lumbosacral daytime pain, valuation factor, Lumbosacral nighttime pain evaluation factor, Lumbosacral extent of pain referral evaluation factor, Lumbosacral quality of pain evaluation factor, Lumbosacral pain relieving factors evaluation factor, Lumbosacral pain precipitating factors evaluation factor, Lumbosacral trauma evaluation factor, Lumbosacral, aresthesia evaluation factor, Thoracic daytime pain evaluation factor, Thoracic nighttime pain evaluation factor, Thoracic extent of pain referral evaluation factor, Thoracic quality of pain evaluation factor, Thoracic pain relieving factors evaluation factor, Thoracic pain precipitating factors evaluation factor, Thoracic trauma, valuation factor, Thoracic paresthesia evaluation factor, Cervical daytime pain evaluation factor, Cervical nighttime pain evaluation factor, Cervical extent of pain referral evaluation factor, Cervical quality of pain evaluation factor, Cervical pain relieving factors evaluation factor, Cervical pain precipitating factors evaluation, actor, Cervical trauma evaluation factor, Cervical paresthesia evaluation factor, Shoulder daytime pain evaluation factor, Shoulder nighttime pain evaluation factor, Shoulder quality of pain evaluation factor, Shoulder pain relieving factors evaluation factor, Shoulder pain precipitating factors evaluation factor, Shoulder trauma evaluation factor, Shoulder contact quality evaluation factor, Elbow daytime pain evaluation factor, Elbow nighttime pain evaluation factor, Elbow quality of pain evaluation factor, Elbow trauma evaluation factor, Elbow contact quality evaluation factor, Hip daytime pain evaluation factor, Hip nighttime pain evaluation factor, Hip quality of pain evaluation factor, Hip trauma evaluation factor, Hip contact quality evaluation factor, Knee daytime pain evaluation factor, Knee nighttime pain evaluation factor, Knee quality of pain evaluation factor, Knee trauma evaluation factor, Knee contact quality evaluation factor, Wrist and hand daytime pain, valuation factor, Wrist and hand nighttime pain evaluation factor, Wrist and hand quality of pain evaluation factor, Wrist and hand contact quality evaluation factor, Wrist and hand vascular changes evaluation factor, Wrist and hand trauma evaluation factor, Wrist and hand non bony deformities evaluation factor, Wrist and hand bony deformities evaluation factor, Ankle and foot daytime pain evaluation factor, Ankle and foot nighttime pain evaluation factor, Ankle and foot quality of pain evaluation factor, Ankle and foot vascular changes evaluation factor, Ankle and foot contact quality evaluation factor, Ankle and foot trauma evaluation factor, Joint welling evaluation factor, Joint stiffness evaluation factor, Systemic Lupus Erythematosis evaluation factor, Rheumatoid Arthritis evaluation factor, Skin morphology evaluation factor, Sunlight effect on skin evaluation factor, Anemia evaluation factor, Immune suppression evaluation factor, Bleeding tendency evaluation factor.

16. The article of manufacture of claim 15, wherein the following evaluation factors comprise Emergency Referral evaluation factors:

Fever, Night sweats, Cough, Short of breath, Respiratory chest wall or shoulder pain, Vomiting, Stool color, Control of bowels, Blood in urine, Control of urine, Urinary frequency, Palpitations, Angina, Relief of presenting symptom, Exercise impact on presenting symptom, Visual loss, Diplopia, Photophobia, Vertigo, Headache, Extent of upper extremity weakness, Extent of lower extremity weakness, Lumbosacral nighttime pain, Lumbosacral trauma, Thoracic nighttime pain, Thoracic trauma, Cervical nighttime pain, Cervical pain precipitating factors, Cervical trauma, Hip daytime pain, Hip nighttime pain, Hip trauma, Wrist and hand vascular changes, Ankle and foot vascular changes, Bleeding tendency.

17. The computer program product of claim 9, further comprising:
  computer readable program code which causes said programmable computer processor to operative if none of said (N) evaluation factors is designated an Emergency Referral evaluation factor:
  computer readable program code which causes said programmable computer processor to setting (i) to 1, wherein (i) is greater than or equal to 1 and less than or equal to (N);
  computer readable program code which causes said programmable computer processor to selecting the (i)th evaluation factor;
  computer readable program code which causes said programmable computer processor to assigning the (i)th point rating using evaluation criteria recited in the (i)th evaluation factor;
  computer readable program code which causes said programmable computer processor to determining if (i) equals (N);
  computer readable program code which causes said programmable computer processor to operative if (i) is less than (N), incrementing (i) by unity and repeating said selecting step, said assigning step, said determining step, and said incrementing step;
  computer readable program code which causes said programmable computer processor to operative if (i) equals (N), determining whether to generate a message recommending the physical therapist refer said client to emergency care based upon the (N) point ratings.

18. The computer program product of claim 17, further comprising computer readable program code which causes said programmable computer processor to determine whether to generate a message recommending the physical therapist refer said client to a physician consult based upon the (N) point ratings.

19. A computer program product encoded in a computer readable medium, said computer program product comprising a plurality of evaluation factors wherein each evaluation factor comprises point ratings from 0 to 5, wherein a higher point rating indicates a higher likelihood that a client should be referred to emergency care, a plurality of evaluation algorithms, wherein each of said evaluation algorithms comprises two or more of said evaluation factors, said computer program product being useable with a processor to evaluate a client presenting to a physical therapist, comprising: computer readable program code which causes said programmable computer processor to determining if a client is experiencing pain;
  computer readable program code which causes said programmable computer processor to operative if a client is experiencing pain, selecting an evaluation algorithm responsive to said pain, wherein said selected evaluation algorithm comprises (N) evaluation factors, wherein (N) is greater than 1;
  computer readable program code which causes said programmable computer processor to determining if any of said (N) evaluation factors is designated an Emergency Referral evaluation factor;
  computer readable program code which causes said programmable computer processor to operative if any of said (N) evaluation factors is designated an Emergency Referral evaluation factor, determining if the client's reported pain corresponds to a point rating of "5" for any of the Emergency Referral evaluation factors;
  computer readable program code which causes said programmable computer processor to operative if the client's reported pain corresponds to a point rating of "5" for any of the Emergency Referral evaluation factors, generating a message recommending that the physical therapist refer the client for immediate emergency care.

20. The computer program product of claim 19, further comprising:
  computer readable program code which causes said programmable computer processor to operative if the client's reported pain does not correspond to a point rating of "5" for any of the Emergency Referral factors comprising said selected evaluation algorithm:
  computer readable program code which causes said programmable computer processor to setting (i) to 1, wherein (i) is greater than or equal to 1 and less than or equal to (N);
  computer readable program code which causes said programmable computer processor to selecting the (i)th evaluation factor;
  computer readable program code which causes said programmable computer processor to assigning the (i)th point rating using evaluation criteria recited in the (i)th evaluation factor;
  computer readable program code which causes said programmable computer processor to determining if (i) equals (N);
  computer readable program code which causes said programmable computer processor to operative if (i) is less than (N), incrementing (i) by unity and repeating said selecting step, said assigning step, said determining step, and said incrementing step;
  computer readable program code which causes said programmable computer processor to operative if (i) equals (N), determining whether to generate a message recommending the physical therapist refer said client to emergency care based upon the (N) point ratings.

21. The computer program product of claim 20, further comprising computer readable program code which causes said programmable computer processor to determine whether to generate a message recommending the physical therapist refer said client to a physician consult based upon the (N) point ratings.

22. The article of manufacture of claim 19, wherein said plurality of evaluation algorithms comprise an Emergency Medical Algorithm, an Ankle and Foot Algorithm, a Cervical Spine Algorithm, an Elbow Algorithm, a Hand And Wrist Algorithm, a Headache Algorithm, a Hip Algorithm, a Knee Algorithm, a Lumbar Spine Algorithm, a Pelvic And Sacrum Algorithm, a Shoulder Algorithm, a Thoracic Spine Algorithm, a Poor Gait, and a Vertigo Algorithm.

23. The computer program product of claim 22, wherein said plurality of evaluation factors comprise a Fever evaluation factor, Weight loss evaluation factor, Night sweats evaluation factor, Day sweats evaluation factor, Sleep pattern evaluation factor, Fatigue evaluation factor, Medical compliance self assessment evaluation factor, Diabetes mellitus evaluation factor, Cough evaluation factor, Oxygen usage evaluation factor, Short of breath evaluation factor, Respiratory chest wall or shoulder pain evaluation factor, Nausea evaluation factor, Vomiting evaluation factor, Heartburn evaluation factor, Stool color evaluation factor, Swallowing completeness evaluation factor, Stool volume evaluation factor, Stool consistency evaluation factor, Control of, bowels evaluation factor, Constipation evaluation factor, Blood in urine evaluation factor, Control of urine evaluation factor, Urinary frequency evaluation factor, Palpitations evaluation factor, Angina evaluation factor, Relief of presenting symptom evaluation factor, Exercise impact on presenting symptom evaluation factor, Visual loss evaluation factor, Visual disturbance evaluation factor, Diplopia evaluation factor, Photophobia evaluation factor, Hearing loss evaluation factor, Swallow coordination evaluation factor, Vertigo evaluation factor, Headache evaluation factor, Frequency of upper extremity change in sensation evaluation factor, Frequency of upper extremity weakness evaluation factor, Extent of upper extremity weakness evaluation factor, Frequency of lower extremity change in sensation evaluation factor, Frequency of lower extremity weakness evaluation factor, Extent of lower extremity weakness evaluation factor, Lumbosacral daytime pain, valuation factor, Lumbosacral nighttime pain evaluation factor, Lumbosacral extent of pain referral evaluation factor, Lumbosacral quality of pain evaluation factor, Lumbosacral pain relieving factors evaluation factor, Lumbosacral pain precipitating factors evaluation factor, Lumbosacral trauma evaluation factor, Lumbosacral, aresthesia evaluation factor, Thoracic daytime pain evaluation factor, Thoracic nighttime pain evaluation factor, Thoracic extent of pain referral evaluation factor, Thoracic quality of pain evaluation factor, Thoracic pain relieving factors evaluation factor, Thoracic pain precipitating factors evaluation factor, Thoracic trauma, valuation factor, Thoracic paresthesia evaluation factor, Cervical daytime pain evaluation factor, Cervical nighttime pain evaluation factor, Cervical extent of pain referral evaluation factor, Cervical quality of pain evaluation factor, Cervical pain relieving factors evaluation factor, Cervical pain precipitating factors evaluation, actor, Cervical trauma evaluation factor, Cervical paresthesia evaluation factor, Shoulder daytime pain evaluation factor, Shoulder nighttime pain evaluation factor, Shoulder quality of pain evaluation factor, Shoulder pain relieving factors evaluation factor, Shoulder pain precipitating factors evaluation factor, Shoulder trauma evaluation factor, Shoulder contact quality evaluation factor, Elbow daytime pain evaluation factor, Elbow nighttime pain evaluation factor, Elbow quality of pain evaluation factor, Elbow trauma evaluation factor, Elbow contact quality evaluation factor, Hip daytime pain evaluation factor, Hip nighttime pain evaluation factor, Hip quality of pain evaluation factor, Hip trauma evaluation factor, Hip contact quality evaluation factor, Knee daytime pain evaluation factor, Knee nighttime pain evaluation factor, Knee quality of pain evaluation factor, Knee trauma evaluation factor, Knee contact quality evaluation factor, Wrist and hand daytime pain, valuation factor, Wrist and hand nighttime pain evaluation factor, Wrist and hand quality of pain evaluation factor, Wrist and hand contact quality evaluation factor, Wrist and hand vascular changes evaluation factor, Wrist and hand trauma evaluation factor, Wrist and hand non bony deformities evaluation factor, Wrist and hand bony deformities evaluation factor, Ankle and foot daytime pain evaluation factor, Ankle and foot nighttime pain evaluation factor, Ankle and foot quality of pain evaluation factor, Ankle and foot vascular changes evaluation factor, Ankle and foot contact quality evaluation factor, Ankle and foot trauma evaluation factor, Joint welling evaluation factor, Joint stiffness evaluation factor, Systemic Lupus Erythematosis evaluation factor, Rheumatoid Arthritis evaluation factor, Skin morphology evaluation factor, Sunlight effect on skin evaluation factor, Anemia evaluation factor, Immune suppression evaluation factor, Bleeding tendency evaluation factor.

24. The computer program product of claim 23, wherein the following evaluation factors comprise Emergency Referral evaluation factors:

Fever, Night sweats, Cough, Short of breath, Respiratory chest wall or shoulder pain, Vomiting, Stool color, Control of bowels, Blood in urine, Control of urine, Urinary frequency, Palpitations, Angina, Relief of presenting symptom, Exercise impact on presenting symptom, Visual loss, Diplopia, Photophobia, Vertigo, Headache, Extent of upper extremity weakness, Extent of lower extremity weakness, Lumbosacral nighttime pain, Lumbosacral trauma, Thoracic nighttime pain, Thoracic trauma, Cervical nighttime pain, Cervical pain precipitating factors, Cervical trauma, Hip daytime pain, Hip nighttime pain, Hip trauma, Wrist and hand vascular changes, Ankle and foot vascular changes, Bleeding tendency.

* * * * *